United States Patent [19]

Senoo et al.

[11] Patent Number: 5,750,371
[45] Date of Patent: May 12, 1998

[54] WATER-SOLUBLE MUTEIN OF FGF RECEPTOR, DNA AND PRODUCTION THEREOF

[76] Inventors: Masaharu Senoo, B-212, 744-1, Nishi-izumigaoka 2-chome, Toyonaka-shi, Osaka, Japan, 560; Tatsuya Watanabe, 50-1, Yamadaminami, Suita-shi, Osaka, Japan, 565; Koichi Igarashi, 66-3, Shimogamo-miyazakicho, Sakyo-ku, Kyoto-shi, Kyoto, Japan, 606

[21] Appl. No.: 471,570

[22] Filed: Jun. 6, 1995

Related U.S. Application Data

[63] Continuation of Ser. No. 149,664, Nov. 9, 1993, abandoned, which is a continuation of Ser. No. 743,369, filed as PCT/JP91/00557 Apr. 25, 1991, abandoned.

[51] Int. Cl.$^6$ .................. C07K 14/71; C07H 21/00; C12N 15/12; C12N 15/63
[52] U.S. Cl. .................. 435/69.1; 435/172.3; 435/361; 435/252.33; 435/320.1; 530/350; 536/23.5; 935/10; 935/73
[58] Field of Search .................. 435/69.1, 320.1, 435/240.1, 252.3, 252.33, 172.3, 361; 530/350, 387, 388.23; 536/23.1, 23.5; 935/10, 73

[56] References Cited

U.S. PATENT DOCUMENTS

| | | | |
|---|---|---|---|
| 5,057,417 | 10/1991 | Hammonds et al. | 435/69.1 |
| 5,110,730 | 5/1992 | Edgington et al. | 435/69.6 |
| 5,185,441 | 2/1993 | Wallner et al. | 536/23.5 |
| 5,229,501 | 7/1993 | Kiefer et al. | 530/399 |
| 5,288,855 | 2/1994 | Bergonzoni et al. | 530/399 |

FOREIGN PATENT DOCUMENTS

89/02922  4/1989  WIPO.

OTHER PUBLICATIONS

Kornbluth et al., *Mol. Cell. Biol.*, 8(12):5541–5544, Dec. 1988.
Pasquale et al. *Natl. Acad. Sci. USA*, 86:5449–5453, Jul. 1989.
Seno et al., *Biochimica et Biophysica Acta*, 1089:244–246, 1991.
Dionne et al., *The EMBO Journal*, 9(9):2685–2692 (1990).
Hattori et al., *Proc. Natl. Acad. Sci USA*, 87(15):5983–5987, Aug. 1990.

*Primary Examiner*—Lorraine M. Spector
*Attorney, Agent, or Firm*—David G. Conlin; Ernest V. Linek

[57] ABSTRACT

Disclosed are (1) a water-soluble mutein of an animal protein having activity as a receptor for a fibroblast growth factor (FGF) protein, (2) a recombinant DNA having a nucleotide sequence coding for the above water-soluble mutein, (3) a vector containing the above recombinant DNA, (4) a transformant transformed with the above vector, and (5) a process for producing the water-soluble mutein which comprises cultivating the above transformant in a culture medium, the mutein being useful as therapeutic agents or to enhance cell proliferation activity.

7 Claims, 36 Drawing Sheets

FIG. 1A

```
         10         20         30         40         50         60
CACCCCGCTGGTGAGGATAACAACACGCCTCTCTTCAACGGCAGACACCCCATGCTGGC
 T  P  L  V  R  I  T  T  R  L  S  S  T  A  D  T  P  M  L  A 70         80         90        100        110        120
AGGGGTCTCCGAGTATGAACTTCCAGAGGACCCAAAATGGGAGTTTCCAAGAGATAAGCT
 G  V  S  E  Y  E  L  P  E  D  P  K  W  E  F  P  R  D  K  L 130        140        150        160        170        180
GACACTGGGCAAGCCCCTGGGGAGAAGGTTGCTTTGGGCAAGTGGTCATGGCGGAAGCAGT
 T  L  G  K  P  L  G  E  G  C  F  G  Q  V  V  M  A  E  A  V 190        200        210        220        230        240
GGGAATTGACAAAGACAAGCCCAAGGAGGCGGTCACCGTGGCCGTGAAGATGTTGAAAGA
 G  I  D  K  D  K  P  K  E  A  V  T  V  A  V  K  M  L  K  D 250        260        270        280        290        300
TGATGCCACAGAGAAAGACCTTTCTGATCTGGTGTCAGAGATGGAGATGATGAAGATGAT
 D  A  T  E  K  D  L  S  D  L  V  S  E  M  E  M  M  K  M  I
```

FIG. 1B

```
         310         320         330         340         350         360
TGGGAAACACAAGAATATCATAAATCTTCTTGGAGCCTGCACACAGGATGGGCCTCTA
 G  K  H  K  N  I  I  N  L  L  G  A  C  T  Q  D  G  P  L  Y 370         380         390         400         410         420
TGTCATAGTTGAGTATGCCTCTCTAAAGGCAACCCTCCGAGAATACCTCCGAGCCCGAGGCC
 V  I  V  E  Y  A  S  K  G  N  L  R  E  Y  L  R  A  R  R  P 430         440         450         460         470         480
ACCCGGGATGCAGTACTCCTATGACATTAACCCTGTGTTCCTGAGGAGCAGATGACCTTCAA
 P  G  M  Q  Y  S  Y  D  I  N  R  V  P  E  E  Q  M  T  F  K 490         500         510         520         530         540
GGACTTGGTGTCATGCACCTACCAGCTGGCCAGAGGCATGGAGTACTTGGCTTCCCAAAA
 D  L  V  S  C  T  Y  Q  L  A  R  G  M  E  Y  L  A  S  Q  K 550         560         570         580         590         600
ATGTATTCATCGAGATTTAGCAGCCAGAAATGTTTGGTAACAGAAAACAATGTGATGAA
 C  I  H  R  D  L  A  A  R  N  V  L  V  T  E  N  N  V  M  K

AATAG
 I
```

FIG. 3A

```
         10         20         30         40         50         60         70
GGACCCGGGGATTGGTACCGTAACCATGGTCAGCTGGGGTCGTTTCATCTGCCTGGTCGTCACCATGG
                              M  V  S  W  G  R  F  I  C  L  V  V  T  M 80         90        100        110        120        130        140
CAACCTTGTCCCTGGCCCGGCCCTCCTTCAGTTTAGTTGAGGATACCACATTAGAGCCAGAAGGAGCACC
 A  T  L  S  L  A  R  P  S  F  S  L  V  E  D  T  T  L  E  P  E  G  A  P 150        160        170        180        190        200        210
ATACTGGACCAACACAGAAAAGATGGAAAAGCGGCTCCATGCTGTGCCTGCGGCCAACACTGTCAAGTTT
 Y  W  T  N  T  E  K  M  E  K  R  L  H  A  V  P  A  A  N  T  V  K  F 220        230        240        250        260        270        280
CGCTGCCCAGCCGGGGGAACCCAATGCCAACCCAATGCCGGTGGCTGAAAACGGAAGGAGTTTAAGCAGG
 R  C  P  A  G  G  N  P  M  P  T  M  R  W  L  K  N  G  K  E  F  K  Q 290        300        310        320        330        340        350
AGCATCGCATTGGAGGCTACAAGGTACGAGAAACCACTGGAGCCTCATTATGGAAAGTGTGGTCCCATC
 E  H  R  I  G  G  Y  K  V  R  N  Q  H  W  S  L  I  M  E  S  V  V  P  S 360        370        380        390        400        410        420
TGACAAGGGAAATTATACCTGTGTGGTGGAGAATGAATACGGGTCCATCAATCACACGTACCACCTGGAT
 D  K  G  N  Y  T  C  V  V  E  N  E  Y  G  S  I  N  H  T  Y  H  L  D
```

FIG. 3B

```
         430        440        450        460        470        480        490
GTTGTGTGGAGCGATCGCCTCACCGGCCCATCCTCCAAGCCGGACTGCCGGCAAATGCCTCCACAGTGGTCG
 V  V  E  R  S  P  H  R  P  I  L  Q  A  G  L  P  A  N  A  S  T  V  V 500        510        520        530        540        550        560
GAGGAGACGTAGAGTTTGTCTGCAAGGTTTACAGTGATGCCCAGCCCCACATCCAGTGGATCAAGCACGT
 G  G  D  V  E  F  V  C  K  V  Y  S  D  A  Q  P  H  I  Q  W  I  K  H  V 570        580        590        600        610        620        630
GGAAAAGAACGGGCAGTAAATACGGGCCCGACGGGCTGCCCTACCTCAAGGTTCTCAAGCACTCGGGGATA
 E  K  N  G  S  K  Y  G  P  D  G  L  P  Y  L  K  V  L  K  H  S  G  I 640        650        660        670        680        690        700
AATAGTTCCAATGCAGAAGTGCTGGCTCTGTTCAATGTGACCGAGGCGGATGCTGGGGAATATATGTA
 N  S  S  N  A  E  V  L  A  L  F  N  V  T  E  A  D  A  G  E  Y  I  C 710        720        730        740        750        760        770
AGGTCTCCAATTATATAGGGCAGGCCAACCAGTCTGCCTGGCTCACTGTCCTGCCAAAAACAGCAAGCGCC
 K  V  S  N  Y  I  G  Q  A  N  Q  S  A  W  L  T  V  L  P  K  Q  Q  A  P 780        790        800        810        820        830        840
TGGAAGAGAAAGGAGATTACAGCTTCCCCAGACTACCTGGAGATAGCCATTTACTGCATAGGGGTCTTC
 G  R  E  K  E  I  T  A  S  P  D  Y  L  E  I  A  I  Y  C  I  G  V  F 850        860        870        880        890        900        910
TTAATCGCCTGTATGGTGGTAACAGTCATCCTGTGCCGAATGAAGAACACGACCAAGAAGCCAGACTTCA
 L  I  A  C  M  V  V  T  V  I  L  C  R  M  K  N  T  T  K  K  P  D  F
```

FIG. 3C

```
      920        930        940        950        960        970        980
GCAGCCAGCCGGCTCTGTGCACAAGCTGACCAAACGTATCCCCCTGCGGAGACAGGTTTCGGCTGAGTCCAG
 S  S  Q  P  A  V  H  K  L  T  K  R  I  P  L  R  R  Q  V  S  A  E  S  S 990       1000       1010       1020       1030       1040       1050
CTCCTCCATGAACTCCAACACCCCGCTGGTGAGGATAACACACCGCCTCTCTTCAACGGCAGACACCCCC
 S  S  M  N  S  N  T  P  L  V  R  I  T  T  R  L  S  S  T  A  D  T  P 1060       1070       1080       1090       1100       1110       1120
ATGCTGGCAGGGGTCTCCGAGTATGAACTTCCAGAGGACCCAAAATGGGAGTTCCAAGAGATAAGCTGA
 M  L  A  G  V  S  E  Y  E  L  P  E  D  P  K  W  E  F  P  R  D  K  L 1130       1140       1150       1160       1170       1180       1190
CACTGGGCAAGCCCCTGGGAGAAGGTTGCTTTGGGCAACTGGTCATGGCGAAGCAGTGGGAATTGACAA
 T  L  G  K  P  L  G  E  G  C  F  G  Q  V  V  M  A  E  A  V  G  I  D  K 1200       1210       1220       1230       1240       1250       1260
AGACAAGCCCAAGGAGGCGGTCACCGTGGCCGTGAAGATGTTGAAAGATGATGCCACAGAGAAAGACCTT
 D  K  P  K  E  A  V  T  V  A  V  K  M  L  K  D  D  A  T  E  K  D  L 1270       1280       1290       1300       1310       1320       1330
TCTGATCTGGTGTCAGAGATGGAGATGATGAAGATGATTGGGAAAACAAGAATATCATAAATCTTCTTG
 S  D  L  V  S  E  M  E  M  M  K  M  I  G  K  H  K  N  I  I  N  L  L
```

FIG. 3D

```
          1340        1350        1360        1370        1380        1390        1400
GAGCCTGCACACAGGATGGGCCTCTCTATGTCATAGTTGAGTATGCCTCTAAAGGCAACCTCCGAGAATA
 G  A  C  T  Q  D  G  P  L  Y  V  I  V  E  Y  A  S  K  G  N  L  R  E  Y 1410        1420        1430        1440        1450        1460        1470
CCTCCGAGCCCGGAGGCCACCCGGGATGGAGTACTCCTATGACATTAACCGTGTTCCTGAGGAGCAGATG
 L  R  A  R  R  P  P  G  M  E  Y  S  Y  D  I  N  R  V  P  E  E  Q  M 1480        1490        1500        1510        1520        1530        1540
ACCTTCAAGGACTTGGTGTCATGCACCTACCAGCTGGCCAGAGGCATGGAGTACTTGGCTTCCCAAAAT
 T  F  K  D  L  V  S  C  T  Y  Q  L  A  R  G  M  E  Y  L  A  S  Q  K 1550        1560        1570        1580        1590        1600
GTATTCATCGAGATTAGCAGCCAGCCAGAAATGTTTTGGTAACAGAAAACAATGTGATGAAAATAG
 C  I  H  R  D  L  A  A  R  N  V  L  V  T  E  N  N  V  M  K  I
```

FIG. 4A

```
         10         20         30         40         50         60         70
GGACCGGGGATTGGTACCGTAACCATGGTCAGCTGGGGTCGTTTCATCTGCCTGGTCGTTGTCACCATGG
                         M  V  S  W  G  R  F  I  C  L  V  V  V  T  M 80         90        100        110        120        130        140
CAACCCTTGTCCCTGGCCCGGCCCCTCCTTCAGTTTAGTTGAGGATACCACATTAGAGCCAGAAGAGCCACC
 A  T  L  S  L  A  R  P  S  F  S  L  V  E  D  T  T  L  E  P  E  E  P  P 150        160        170        180        190        200        210
AACCAAATACCAAATCTCTCAACCAGAAGTGTACGTGGCTGCCCAGGGAGTCGCTAGAGGTGCGCTGC
 T  K  Y  Q  I  S  Q  P  E  V  Y  V  V  A  A  P  G  E  S  L  E  V  R  C 220        230        240        250        260        270        280
CTGTTGAAAGATGCCGCCGTGATCAGTTGGACTAAGGATGGGGTGCACTTGGGGCCAACAATAGGACAG
 L  L  K  D  A  A  V  I  S  W  T  K  D  G  V  H  L  G  P  N  N  R  T 290        300        310        320        330        340        350
TGCTTATTGGGAGTACTTGCAGATATAAAGGGCGCCACGCCTAGAGACTCCGGCCTCTATGCTTGTACTGC
 V  L  I  G  E  Y  L  Q  I  K  G  A  T  P  R  D  S  G  L  Y  A  C  T  A 360        370        380        390        400        410        420
CAGTAGGACTGTAGACAGTGAAACTTGGTACTTCATGGTGAATGTCACAGATGCCATCTCATCCGGAGAT
 S  R  T  V  D  S  E  T  W  Y  F  M  V  N  V  T  D  A  I  S  S  G  D 430        440        450        460        470        480        490
GATGAGGATGACACCGATGGTGCGGAAGATTTTGTCAGTGAGAACAGTAACAACAAGAGACCATACT
 D  E  D  D  T  D  G  A  E  D  F  V  S  E  N  S  N  N  K  R  A  P  Y
```

FIG. 4B

```
        500       510       520       530       540       550       560
GGACCAACACAGAAAAAGATGGAAAAAGCGGCTCCATGCTGTGCCTGCGGCCAACACTGTCAAGTTTCGCTG
  W  T  N  T  E  K  M  E  K  R  L  H  A  V  P  A  A  N  T  V  K  F  R  C 570       580       590       600       610       620       630
CCCAGCCGGGGGAACCCATGCCAACCATGCGGTGCTGGCTGAAAAACGGGAAGGAGTTTAAGCAGGAGCAT
  P  A  G  G  N  P  M  P  T  M  R  W  L  K  N  G  K  E  F  K  Q  E  H 640       650       660       670       680       690       700
CGCATTGGAGGCTACAAGGTACGAAACCAGCACCTGAGCCTCATTATGGAAAGTGTGTCCCATCTGACA
  R  I  G  G  Y  K  V  R  N  Q  H  W  S  L  I  M  E  S  V  V  P  S  D 710       720       730       740       750       760       770
AGGGAAATTATACCTGTGTGGTGGAGAATGAATACGGGTCCATCAATCACACGTACCACCTGGATGTTGT
  K  G  N  Y  T  C  V  V  E  N  E  Y  G  S  I  N  H  T  Y  H  L  D  V  V 780       790       800       810       820       830       840
GGAGCGGATCGCCTCACCGGCCCATCCTCCAAGCCGGACTGCCGGCAAATGCCTCCACAGTGGTCGGAGGA
  E  R  S  P  H  R  P  I  L  Q  A  G  L  P  A  N  A  S  T  V  V  G  G 850       860       870       880       890       900       910
GACGTAGAGTTTGTCTGCAAGGTTTACAGTGATGCCCAGCCCCACATCCAGTGGATCAAGCACGTGGAAA
  D  V  E  F  V  C  K  V  Y  S  D  A  Q  P  H  I  Q  W  I  K  H  V  E 920       930       940       950       960       970       980
AGAACGGCAGTAAATACGGGCCCGACGGGCTGCCCTACCTTCAAGGTTCTCAAGCACTCGGGGATAAATAG
  K  N  G  S  K  Y  G  P  D  G  L  P  Y  L  K  V  L  K  H  S  G  I  N  S 990      1000      1010      1020      1030      1040      1050
TTCCAATGCAGAAGTGCTGGCTCTGTTCAATGTGACCGAGGCGGATGCGGGGGAATATATATGTAAGGTC
  S  N  A  E  V  L  A  L  F  N  V  T  E  A  D  A  G  E  Y  I  C  K  V
```

FIG. 4C

```
      1060       1070       1080       1090       1100       1110       1120
TCCAATTATATAGGGCAGGCAGGCCAACCAGTCTGCCTGGCTCACTGTCCTGCCAAAACAGCAAGCGCCTGGAA
 S  N  Y  I  G  Q  A  N  Q  S  A  W  L  T  V  L  P  K  Q  Q  A  P  G 1130       1140       1150       1160       1170       1180       1190
GAGAAAAGGAGATTACAGCTTCCCCAGAGACTACCTGGAGATAGCCATTTACTGCATAGGGGTCTTTCTTAAT
 R  E  K  E  I  T  A  S  P  D  Y  L  E  I  A  I  Y  C  I  G  V  F  L  I 1200       1210       1220       1230       1240       1250       1260
CGGCCTGTATGGTGGTAACAGTCATCCTCCTGTGCCGAATGAAGAACCGACCAAGAAGAACACTTCAGCAGC
 A  C  M  V  V  T  V  I  L  C  R  M  K  N  T  T  K  K  P  D  F  S  S 1270       1280       1290       1300       1310       1320       1330
CAGCCCGGCTGTGCACAAGCTGACCAAACGTATCCCCCTGCGGAGACAGGTAACAGTTTCGGCTGAGTCCA
 Q  P  A  V  H  K  L  T  K  R  I  P  L  R  R  Q  V  T  V  S  A  E  S 1340       1350       1360       1370       1380       1390       1400
GCTCCTCCATGAACTCCAACACACCCCTGGTGAGGATAACAACACGCCTCTCTTCAACGGCAGACACCCC
 S  S  S  M  N  S  N  T  P  L  V  R  I  T  T  R  L  S  S  T  A  D  T  P 1410       1420       1430       1440       1450       1460       1470
CATGCTGGCAGGGGTCTCCGAGTATGAACTTCCAGAGGACCCAAAATGGGAGTTTCCAAGAGATAAGCTG
 M  L  A  G  V  S  E  Y  E  L  P  E  D  P  K  W  E  F  P  R  D  K  L 1480       1490       1500       1510       1520       1530       1540
ACACTGGGCAAGCCCCCTGGGAGAAGGTTGCTTTGGGCAAGTGGTCATGGTGGTCGAAGCAGTGGGAATTGGACA
 T  L  G  K  P  L  G  E  G  C  F  G  Q  V  V  M  A  E  A  V  G  I  D
```

FIG. 4D

```
          1550       1560       1570       1580       1590       1600       1610
      AAGACAAGCCCAAGGAGGCGGTCACCGTGGCCGTGAAAGATGTTGAAAGATGATGCCACAGAGAAAGACCT
       K  D  K  P  K  E  A  V  T  V  A  V  K  M  L  K  D  D  A  T  E  K  D  L 1620       1630       1640       1650       1660       1670       1680
      TTCTGATCTGGTGTGTCAGAGATGGAGATGATGAAGATGGGAAACACAAGAATATCATAAATCTTCTT
       S  D  L  V  S  E  M  E  M  M  K  M  I  G  K  H  K  N  I  I  N  L  L 1690       1700       1710       1720       1730       1740       1750
      GGAGCCTGCACACAGGATGGGCCCTCTCTCTATGTCATAGTTGAGTATGCCTCTAAAGGCAACCTCCGAGAAT
       G  A  C  T  Q  D  G  P  L  Y  V  I  V  E  Y  A  S  K  G  N  L  R  E 1760       1770       1780       1790       1800       1810       1820
      ACCTCCGAGCCCGGAGGCCACCCGGGATGGAGTACTCCTATGACATTAACCGTGTTCCTGAGGAGCAGAT
       Y  L  R  A  R  R  P  P  G  M  E  Y  S  Y  D  I  N  R  V  P  E  E  Q  M 1830       1840       1850       1860       1870       1880       1890
      GACCTTCAAGGACTTGGTGTGTCATGCACCTACCAGCTGGCCAGAGGCATGGAGTACTTGGCTTCCCAAAAA
       T  F  K  D  L  V  S  C  T  Y  Q  L  A  R  G  M  E  Y  L  A  S  Q  K 1900       1910       1920       1930       1940       1950
      TGTATTCATCGAGATTTAGCAGCCAGAAATGTTTTGGTAACAGAAAAACAATGTGATGAAAATAG
       C  I  H  R  D  L  A  A  R  N  V  L  V  T  E  N  N  V  M  K  I
```

FIG. 7A

```
           10                  20                  30                  40                  50                  60                  70
GGACCGGGGATTGGTACCGTAACCATGGTCAGCTGGGTCGTTTCATCTGCCTGGTCGTGGTCACCATGG
                            M   V   S   W   G   R   F   I   C   L   V   V   V   T   M 80                  90                 100                 110                 120                 130                 140
CAACCTTGTCCCTGGCCCGGCCCTCTTCAGTTTAGTTGAGGATACCACATTAGAGCCAGAAGAGCCACC
 A   T   L   S   L   A   R   P   S   F   S   L   V   E   D   T   T   L   E   P   E   E   P   P 150                 160                 170                 180                 190                 200                 210
AACCAAATACCAAATCTCTCAACCAGAAGTGTACGTGGCTGCGCCAGGGAGTCGCTAGAGGTGCGCTGC
 T   K   Y   Q   I   S   Q   P   E   V   Y   V   A   A   P   G   E   S   L   E   V   R   C 220                 230                 240                 250                 260                 270                 280
CTGTTGAAAGATGCCGCCGTGATCAGTTGGACTAAGGATGGGGTGCACTTGGGGCCCAACAATAGGACAG
 L   L   K   D   A   A   V   I   S   W   T   K   D   G   V   H   L   G   P   N   N   R   T 290                 300                 310                 320                 330                 340                 350
TGCTTATTGGGGAGTACTTGCAGATAAAGGGCGCCACGCCTAGAGACTCCGGCCTCTATGCTTGTACTGC
 V   L   I   G   E   Y   L   Q   I   K   G   A   T   P   R   D   S   G   L   Y   A   C   T   A 360                 370                 380                 390                 400                 410                 420
CAGTAGGACTGTAGACAGTGAAACTTGGTACTTCATGGTGAATGTCACAGATGCCATCTCATCCGGAGAT
 S   R   T   V   D   S   E   T   W   Y   F   M   V   N   V   T   D   A   I   S   S   G   D 430                 440                 450                 460                 470                 480                 490
GATGAGGATGACACCGATGGTGCGGAAGATTTTGTCAGTGAGAACAGTAACAACAAGAGAGCACCATACT
 D   E   D   D   T   D   G   A   E   D   F   V   S   E   N   S   N   N   K   R   A   P   Y
```

FIG. 7B

```
       500        510        520        530        540        550        560
GGACCAACACAGAAAAAGATGGAAAAGCGGCTCCATGCTGTGCCTGCGGCCAACACTGTCAAGTTTCGCTG
 W  T  N  T  E  K  M  E  K  R  L  H  A  V  P  A  A  N  T  V  K  F  R  C 570        580        590        600        610        620        630
CCCAGCCGGGGGAACCCAATGCCAACCATGCGGTGGCTGAAAACGGAAGGAGTTAAGCAGGAGCAT
 P  A  G  G  N  P  M  P  T  M  R  W  L  K  N  G  K  E  F  K  Q  E  H 640        650        660        670        680        690        700
CGCATTGGAGGCTACAAGGTACGAAACCAGCACTGGAGCCTCATTATGGAAAGTGTGGTCCCATCTGACA
 R  I  G  G  Y  K  V  R  N  Q  H  W  S  L  I  M  E  S  V  V  P  S  D 710        720        730        740        750        760        770
AGGGAAATTATACCTGTGTGGTGGAGAATGAATACGGGTCCATCAATCACACGTACCACCTGGATGTTGT
 K  G  N  Y  T  C  V  V  E  N  E  Y  G  S  I  N  H  T  Y  H  L  D  V  V 780        790        800        810        820        830        840
GGAGCGGATCGCCTCACCGGCCCATCCTCCAAGCCCGGACTGCCGGCAAATGCCTCCACAGTGGTCGGAGGA
 E  R  S  P  H  R  P  I  L  Q  A  G  L  P  A  N  A  S  T  V  V  G  G 850        860        870        880        890        900        910
GACGTAGAGTTTGTCTGCAAGGTTTACAGTGATGCCCAGCCCCACATCCAGTGGATCAAGCACGTGGAAA
 D  V  E  F  V  C  K  V  Y  S  D  A  Q  P  H  I  Q  W  I  K  H  V  E
```

FIG. 7C

```
       920        930        940        950        960        970        980
AGAACGGGCAGTAAATACGGGCCCGACGGGCTGCCCTACCTCAAGGTTCTCAAGCACTCGGGGATAAATAG
 K  N  G  S  K  Y  G  P  D  G  L  P  Y  L  K  V  L  K  H  S  G  I  N  S 990       1000       1010       1020       1030       1040       1050
TTCCAATGCAGAAGTGCTGGCTCTGTTCAATGTGACCGAGGGGATGCGGGGAATATATATGTAAGGTC
 S  N  A  E  V  L  A  L  F  N  V  T  E  A  D  A  G  E  Y  I  C  K  V 1060       1070       1080       1090       1100       1110       1120
TCCAATTATATAGGGCAGGCCAACCAGTCTGCCTGGCTCACTGTCCTGCCAAAACAGCAAGCCCTGGAA
 S  N  Y  I  G  Q  A  N  Q  S  A  W  L  T  V  L  P  K  Q  Q  A  P  G 1130       1140       1150       1160       1170       1180       1190
GAGAAAAGGAGATTACAGCTTCCCCAGACTACCTGGAGATAGCCATTTACTGCATAGGGGTCTTCTTAAT
 R  E  K  E  I  T  A  S  P  D  Y  L  E  I  A  I  Y  C  I  G  V  F  L  I 1200       1210       1220       1230       1240       1250       1260
CGCCTGTATGGTGTAACAGTCATCCTCCTGTGCCGAATGAAGAACACGACCAAGAAGCCAGACTTCAGCAGC
 A  C  M  V  V  T  V  I  L  C  R  M  K  N  T  T  K  K  P  D  F  S  S 1270       1280       1290       1300       1310       1320       1330
CAGCCGGCTGTGCACAAGCTGACCAAACGTATCCCCCTGCGGAGACAGGTAACAGTTTCGGCTGAGTCCA
 Q  P  A  V  H  K  L  T  K  R  I  P  L  R  R  Q  V  T  V  S  A  E  S 1340       1350       1360       1370       1380       1390       1400
GCTCCTCCATGAACTCCAACACCCCGCTGGTGAGGATAACAACACGCCTCTCTTCAACGGCAGACACCCC
 S  S  S  M  N  S  N  T  P  L  V  R  I  T  T  R  L  S  S  T  A  D  T  P
```

FIG. 7D

```
     1410      1420      1430      1440      1450      1460      1470
CATGCTGGCAGGGGTCTCCGAGTATGAACTTCCAGAGGACCCAAAATGGGAGTTTCCAAGAGATAAGCTG
 M  L  A  G  V  S  E  Y  E  L  P  E  D  P  K  W  E  F  P  R  D  K  L 1480      1490      1500      1510      1520      1530      1540
ACACTGGGCAAGCCCCTGGGAGAAGGTTGCTTTGGGCAAGTGGTCATGGCGGAAGCAGTGGGAATTGACA
 T  L  G  K  P  L  G  E  G  C  F  G  Q  V  V  M  A  E  A  V  G  I  D 1550      1560      1570      1580      1590      1600      1610
AAGACAAGCCCAAGGAGGCGGTCACCGTGGCCCGTGAAGATGTTGAAAGATGATGCCACAGAGAAAGACCT
 K  D  K  P  K  E  A  V  T  V  A  V  K  M  L  K  D  D  A  T  E  K  D  L 1620      1630      1640      1650      1660      1670      1680
TTCTGATCTGGTGTCAGAGATGGAGATGATGAAGATGATTGGGAAACACAAGAATATCATAAATCTTCTT
 S  D  L  V  S  E  M  E  M  M  K  M  I  G  K  H  K  N  I  I  N  L  L 1690      1700      1710      1720      1730      1740      1750
GGAGCCTGCACACAGGATGGGCCCTCTCTATGTCATAGTTGAGTATGCCTCTAAAGGCAACCTCCGAGAAT
 G  A  C  T  Q  D  G  P  L  Y  V  I  V  E  Y  A  S  K  G  N  L  R  E 1760      1770      1780      1790      1800      1810      1820
ACCTCCGAGCCCGGAGGCCACCCGGGATGGAGTACTCCTATGACATTAACCGTGTCCTGAGGAGCAGAT
 Y  L  R  A  R  R  P  P  G  M  E  Y  S  Y  D  I  N  R  V  P  E  E  Q  N 1830      1840      1850      1860      1870      1880      1890
GACCTTCAAGGACTTGGTGTCATGCACCTACCAGCTGGCCAGAGGCATGGAGTACTTGGCTTCCCAAAAA
 T  F  K  D  L  V  S  C  T  Y  Q  L  A  R  G  M  E  Y  L  A  S  Q  K
```

FIG. 7E

```
         1900       1910       1920       1930       1940       1950       1960
TGTATTCATCGAGATTTAGCAGCCAGAAACAATGTTTGGTAACAGAAAACAATGTGATGAAAATAGCAGACT
 C  I  H  R  D  L  A  A  R  N  V  L  V  T  E  N  N  V  M  K  I  A  D 1970       1980       1990       2000       2010       2020       2030
TTGGACTCGCCAGAGATCTTCAACATATAGACTATTACAAAAAGACCACTAATGGGCGCTTCCAGTCAA
 F  G  L  A  R  D  I  N  N  I  D  Y  Y  K  T  T  N  G  R  L  P  V  K 2040       2050       2060       2070       2080       2090       2100
GTGGATGGCTCCAGAAGCCCTGTTTGATAGAGTATACACTCATCAGAGTGATGTCTGGTCCTTCGGGGTG
 V  M  A  P  E  A  L  F  D  R  V  Y  T  H  Q  S  D  V  W  S  F  G  V 2110       2120       2130       2140       2150       2160       2170
TTAATGTGGGAGATCTTCACTTTAGGGGGCTCGCCCTACCCAGGATTCCCGTGGAGAACTTTTTAAGC
 L  M  W  E  I  F  T  L  G  G  S  P  Y  P  G  I  P  V  E  E  L  F  K 2180       2190       2200       2210       2220       2230       2240
TGCTGAAGGAAGGACACAGAATGGGATAAGCCAGCCAACTGCACCAACGTATACATGATGAGGGA
 L  L  K  E  G  H  R  M  D  K  P  A  N  C  T  N  E  L  Y  M  M  R  D 2250       2260       2270       2280       2290       2300       2310
CTGTTGGCATGCAGTGCCCTCCCAGAGACCAACGTTCAAGCAGTTGGTAGAAGACTTGGATCGAATTCTC
 C  W  H  A  V  P  S  Q  R  P  T  F  K  Q  L  V  E  D  L  D  R  I  L
```

FIG. 7F

```
     2320       2330       2340       2350       2360       2370       2380
ACTCTCACAACCAATGAGATCTGAAAGTTTATGGCTTCATTGAGAAACTGGAAAAGTTGGTCAGGCCA
 T  L  T  T  N  E  I 2390       2400       2410       2420       2430       2440       2450
GTGGCTCATGCCTGTAATCCCAGCACTTTGGGAGGCCGAGGCAGGCGGATCATGAGGTCAGGAGTTCCAG 2460       2470       2480       2490       2500       2510       2520
ACCAGCCTGGCCAACATGGTGAAACCCTGTCTCTACTAAAGATACAAAAATTAGCCGGGCCGTGTTGGTG 2530       2540       2550       2560       2570       2580       2590
TGCGCCTGTAATCCCAGCTACTCCGGGAGGCTGAGGCAGGAGAGTCACTTGAACCCGGGAGGCGGAGGTT 2600       2610       2620       2630       2640       2650       2660
ACAGTGAGCCGAGATCATGCCATTGCCATTCCAGCCCTTGGGCGACAGAGCGAGACTCCATCTAAAAAAAA

2670
AAAAAAAAAAAAA
```

FIG. 8A

```
         10        20        30        40        50        60        70
GGACCGGGGATTGGTACCCGTAACCATGGTCAGCTGGGGTCGTTTCATCTGCCTGGTCGTGGTCACCATGG
                          M  V  S  W  G  R  F  I  C  L  V  V  V  T  M 80        90       100       110       120       130       140
CAACCCTGTCTGCCCTGCGCCCGGCCCTCCTTCAGTTTAGTTGAGGATACCACATTAGAGCCAGAAGGAGCACC
 A  T  L  S  L  A  R  P  S  F  S  L  V  E  D  T  L  E  P  E  G  A  P 150       160       170       180       190       200       210
ATACTGGACCAACACAGAAAAGATGGAAAAGCGGCTCCATGCTGTGCCGGCCAACACTGTCAAGTTT
 Y  W  T  N  T  E  K  M  E  K  R  L  H  A  V  P  A  A  N  T  V  K  F 220       230       240       250       260       270       280
CGCTGCCCAGCCGGGGGGAACCCAATGCCAACCAGCTGGCTGTGCTGAAAAACGGGAAGGAGTTTAAGCAGG
 R  C  P  A  G  G  N  P  M  P  T  M  R  W  L  K  N  G  K  E  F  K  Q 290       300       310       320       330       340       350
AGCATCGCATTGGAGGCTACAAGGTACGAAACCAGCACTGGAGCCTCATTATGGAAAGTGTGGTCCCATC
 E  H  R  I  G  G  Y  K  V  R  N  Q  H  W  S  L  I  M  E  S  V  V  P  S 360       370       380       390       400       410       420
TGACAAGGAAATTATACCTGTGTGTGTGTGGAGAATGAATACGGGTCCATCAATCACACGTACCACCTGGAT
 D  K  G  N  Y  T  C  V  V  E  N  E  Y  G  S  I  N  H  T  Y  H  L  D 430       440       450       460       470       480       490
GTTGTGGAGCGATCGCCTCACGGGGACCCATCCTCCAAGCCTCCGGCGGACTGCGGCAAATGCCTCCACAGTGGTCG
 V  V  E  R  S  P  H  R  P  I  L  Q  A  G  L  P  A  N  A  S  T  V  V
```

FIG. 8B

```
         500           510           520           530           540           550           560
GAGGAGACGTAGAGAGTTTGTCTGCAAGGTTTACAGTGATGCCCAGCCCCACATCCAGTGGATCAAGCACGT
 G  G  D  V  E  F  V  C  K  V  Y  S  D  A  Q  P  H  I  Q  W  I  K  H  V 570           580           590           600           610           620           630
GGAAAAGAACGGCAGTAAATACGGGGCCCGACGGGGCTGCCCTACCTCAAGGTTCTCAAGCACTCGGGATA
 E  K  N  G  S  K  Y  G  P  D  G  L  P  Y  L  K  V  L  K  H  S  G  I 640           650           660           670           680           690           700
AATAGTTCCAATGCAGAAGTGCTGGCTCTGTTCAATGTGACCGAGGCGGATGCTGGGGAATATATGTA
 N  S  S  N  A  E  V  L  A  L  F  N  V  T  E  A  D  A  G  E  Y  I  C 710           720           730           740           750           760           770
AGGTCTCCAATTATATAGGGCAGGCCAACCAGTCTCCTGGCTCACTGTCCTGCCAAACAGCAAGCGCC
 K  V  S  N  Y  I  G  Q  A  N  Q  S  A  W  L  T  V  L  P  K  Q  A  P 780           790           800           810           820           830           840
TGGAAGAGAAAAGGAGATTACAGCTTCCCCAGACTACCTGGAGATAGCCATTTACTGCAGGATGAAGAACACGACCAAGAAGCCAGACTTC
 G  R  E  K  E  I  T  A  S  P  D  Y  L  E  I  A  I  Y  C  R  M  K  N  T  T  K  P  D  F 850           860           870           880           890           900           910
TTAATCGCCTGTATGGTTAACAGTCATCCTCCTGTGCCGAATGAAGAAACGACCAAGAAGCCAGACTTCA
 L  I  A  C  M  V  V  T  V  I  L  C  R  M  K  N  T  T  K  P  D  F
```

FIG. 8C

```
       920        930        940        950        960        970        980
GCAGCCAGCCGGCTGTGCACAAGCTGACCAAGCGTATCCCCCTGCGGAGACAGGTTTCGGCTGAGTCCAG
 S  S  Q  P  A  V  H  K  L  T  K  R  I  P  L  R  R  Q  V  S  A  E  S  S 990       1000       1010       1020       1030       1040       1050
CTCCTCCATGAACTCCAACACCCCGCTGGTGAGATAACAACACGCCTCTCTTCAACGGCAGACACCCCC
 S  S  M  N  S  N  T  P  L  V  R  I  T  T  R  L  S  S  T  A  D  T  P 1060       1070       1080       1090       1100       1110       1120
ATGCTGGCAGGGGTCTCCGAGTATGAACTTCCAGAGGACCCAAAATGGGAGTTTCCAAGAGATAAGCTGA
 M  L  A  G  V  S  E  Y  E  L  P  E  D  P  K  W  E  F  P  R  D  K  L 1130       1140       1150       1160       1170       1180
CACTGGGCAAGCCCCTGGGAGAAGGTTGCTTTGGGCAAGTGGTCATGGCGGAAGCAGTGGGAATTGACAA
 T  L  G  K  P  L  G  E  G  C  F  G  Q  V  V  M  A  E  A  V  G  I  D  K 1190       1200       1210       1220       1230       1240       1250       1260
AGACAAGCCCAAGGAGGCGGTCACCGTGGCCCCTGTGAAAGATGTTGAAAGATGATGCCACAGAAAGACCTT
 D  K  P  K  E  A  V  T  V  A  V  K  M  L  K  D  D  A  T  E  K  D  L 1270       1280       1290       1300       1310       1320       1330
TCTGATCTGGTGTCAGAGATGGAGATGAAGATGAAAACAAGAATATCATAAATCTCTTG
 S  D  L  V  S  E  M  E  M  M  K  M  I  G  K  H  K  N  I  N  L  L 1340       1350       1360       1370       1380       1390       1400
GAGCCTGCACACAGGATGGGCCCTCTCTATGTCATAGTTGAGTATGCCTCTAAAGGCAACCTCCGAGAATA
 G  A  C  T  Q  D  G  P  L  Y  V  I  V  E  Y  A  S  K  G  N  L  R  E  Y
```

FIG. 8D

```
      1410        1420        1430        1440        1450        1460        1470
CCTCCGAGCCCGGAGGCCACCCGGGATGGAGTACTCCTATGACATTAACCGTGTTCCTGAGGAGCAGATG
 L  R  A  R  R  P  P  G  M  E  Y  S  Y  D  I  N  R  V  P  E  E  Q  M 1480        1490        1500        1510        1520        1530        1540
ACCTTCAAGGACTTGGTGTCATGCACCTACCAGTCTGGCCAGAGGCATGGAGTACTTGGCTTCCCAAAAT
 T  F  K  D  L  V  S  C  T  Y  Q  L  A  R  G  M  E  Y  L  A  S  Q  K 1550        1560        1570        1580        1590        1600        1610
GTATTCATCGAGATTTAGCAGCCAGAAATGTTTTGGTAACAGAAAACAATGTGATGAAAATAGCAGACTT
 C  I  H  R  D  L  A  A  R  N  V  L  V  T  E  N  N  V  M  K  I  A  D  F 1620        1630        1640        1650        1660        1670        1680
TGGACTCGCCAGAGATATCAACAACATATAGACTATTACAAAAAGACCACCAATGGGCGGCTTCCAGTCAAG
 G  L  A  R  D  I  N  N  I  D  Y  Y  K  K  T  T  N  G  R  L  P  V  K 1690        1700        1710        1720        1730        1740        1750
TGGATGGCTCCAGAAGCCCTGTTTGATAGAGTATACACTCATCAGAGTGATGTCTGTTCCTTCGGGGTGT
 W  M  A  P  E  A  L  F  D  R  V  Y  T  H  Q  S  D  V  W  S  F  G  V 1760        1770        1780        1790        1800        1810        1820
TAATGTGGGAGATCTTCACTTTAGGGGGCTCCCCTACCCAGGGATTCCCGTGGAGAACTTTTAAGCT
 L  M  W  E  I  F  T  L  G  G  S  P  Y  P  G  I  P  V  E  E  L  F  K  L 1830        1840        1850        1860        1870        1880        1890
GCTGAAGGAGGACACAGAATGGATAAGCCAGCCAACTGCACCAACGAACTGTACATGATGATGAGGGAC
 L  K  E  G  H  R  M  D  K  P  A  N  C  T  N  E  L  Y  M  M  M  R  D
```

FIG. 8E

```
       1900       1910       1920       1930       1940       1950       1960
TGTTGGCATGCAGTGCCTCCCAGAGACCAACGTTCAAGCAGTTGGTAGAAGACTTGGATCGAATTCTCA
 C  W  H  A  V  P  S  Q  R  P  T  F  K  Q  L  V  E  D  L  D  R  I  L 1970       1980       1990       2000       2010       2020       2030
CTCTCACAACCAATGAGATCTGAAAGTTTATGGCTTCATTGAGAAAAGTTGGGAAAAGTTGGTCAGGCGCAG
 T  L  T  T  N  E  I 2040       2050       2060       2070       2080       2090       2100
TGGCTCATGCCTGTAATCCCAGCACTTTGGGAGGCCGAGGCAGGCGGATCATGAGGTCAGGAGTTCCAGA 2110       2120       2130       2140       2150       2160       2170
CCAGCCTGGCCAACATGGTGAAACCCTGTCTCTACTAAAGATACAAAAATTAGCCGGGCGTGTGGTGT 2180       2190       2200       2210       2220       2230       2240
GCGCCTGTAATCCCAGCTACTCCGGGAGGCTGAGGCAGGAGAGTCACTTGAACCCGGGAGGCGGAGGTTA 2250       2260       2270       2280       2290       2300       2310
CAGTGAGCCGAGATCATGCCATTGCATTCCAGCCTTGGCGACAGAGCGAGACTCCATCTAAAAAAAAAA
```

FIG. 11A

```
         10         20         30         40         50         60         70
CATATGCGGCCCTCCTTCAGTTTAGTTGAGGATACCACATTAGAGCCAGAAGGAGCACCATACTGGACCA
 M   R   P   S   F   S   L   V   E   D   T   L   E   P   E   G   A   P   Y   W   T 80         90        100        110        120        130        140
ACACAGAAAAAGATGGAAAAGCGGCTCCATGCTGTGCCTGCGGGCCAACACTGTCAAGTTTCGCTGCCCAGC
 N   T   E   K   M   E   K   R   L   H   A   V   P   A   A   N   T   V   K   F   R   C   P   A 150        160        170        180        190        200        210
CGGGGGAACCCAATGCCAACCATGCGGTGGCTGAAAAACGGGAAGGAGTTTAAGCAGGAGCATCGCATT
 G   G   N   P   M   P   T   M   R   W   L   K   N   G   K   E   F   K   Q   E   H   R   I 220        230        240        250        260        270        280
CGGAGGCTACAAGGTACGAAACCAGCACTGGAGCCCTCATTATGGAAAGTGTGGTCCCATCCGACAAGGGAA
 G   G   Y   K   V   R   N   Q   H   W   S   L   I   M   E   S   V   V   P   S   D   K   G 290        300        310        320        330        340        350
ATTATACCTGTGTGGTGGTGGAGAATGAATACGGGTCCATCAATCACACGTACCACCTGGATGTTGTGGAGCG
 N   Y   T   C   V   V   E   N   E   Y   G   S   I   N   H   T   Y   H   L   D   V   V   E   R 360        370        380        390        400        410        420
ATCGCCTCACCGGCCCATCCTCCAAGCCGGACTGCCGGCAAATGCCTCCACAGTGGTCGGAGGAGACGTA
 S   P   H   R   P   I   L   Q   A   G   L   P   A   N   A   S   T   V   V   G   G   D   V
```

FIG. 11B

```
     430       440       450       460       470       480       490
GAGTTTGTCTGCAAGGTTTACAGTGATGCCCAGCCCCACATCCAGTGGATCAAGCACGTGGAAAAGAACG
 E   F   V   C   K   V   Y   S   D   A   Q   P   H   I   Q   W   I   K   H   V   E   K   N 500       510       520       530       540       550       560
GCAGTAAATACGGGCCCGACGGGCTGCCCTACCTCAAGGTTCTCAAGCACTCGGGGATAAATAGTTCCAA
 G   S   K   Y   G   P   D   G   L   P   Y   L   K   V   L   K   H   S   G   I   N   S   N 570       580       590       600       610       620       630
TGCAGAAGTGCTGGCTCTGTTCAATGTGACCGAGGCGGATGCTGGGGAATATATATGTAAGGTCTCCAAT
 A   E   V   L   A   L   F   N   V   T   E   A   D   A   G   E   Y   I   C   K   V   S   N 640       650       660       670       680       690       700
TATATAGGGCAGGCCAACCAGTCTGCCTGGCTCACTGTCCTGCCAAAACAAGCAAGCCCTGGAAGAGAAA
 Y   I   G   Q   A   N   Q   S   A   W   L   T   V   L   P   K   Q   Q   A   P   G   R   E 710       720       730
AGGAGATTACAGCTTCCCCAGACTAACTGGATCC
 K   E   I   T   A   S   P   D
```

FIG. 12A

```
         10         20         30         40         50         60         70
CATATGCGGCCCTCCTTCAGTTTAGTTGAGGATACCACATTAGAGCCAGAGAGCCACCAACCAAATACC
  M   R   P   S   F   S   L   V   E   D   T   T   L   E   P   E   E   P   P   T   K   Y 80         90        100        110        120        130        140
AAATCTCTCAACCAGAAGTGTACGTGGCTGCCCCAGGGGAGTCGCTAGAGGTGCGCTGCCTGTTGAAAGA
  Q   I   S   Q   P   E   V   Y   V   A   A   P   G   E   S   L   E   V   R   C   L   L   K   D 150        160        170        180        190        200        210
TGCCCCGGTGATCAGTTGGACTAAGGATGGGGTGCACTTGGGGCCCAACAATAGGACGTGCTTATTGGG
  A   A   V   I   S   W   T   K   D   G   V   H   L   G   P   N   N   R   T   V   L   I   G 220        230        240        250        260        270        280
GAGTACTTGCAGATAAAGGGGCCACGCCTAGAGACTCCGGCCTTCTATGCTTGTGCCAGTAGGACTG
  E   Y   L   Q   I   K   G   A   T   P   R   D   S   G   L   Y   A   C   T   A   S   R   T 290        300        310        320        330        340        350
TAGACAGTGAAACTTGGTACTTCATGGTGAATGTCACAGATGCCATCTCATCCGGAGATGATGAGGATGA
  V   D   S   E   T   W   Y   F   M   V   N   V   T   D   A   I   S   S   G   D   D   E   D   D 360        370        380        390        400        410        420
CACCGGATGGTGCCGGAAGATTTTGTCAGTGAGAACAGTAACAACAAGAGACCATACTGGACCAACACA
  T   D   G   A   E   D   F   V   S   E   N   S   N   N   K   R   A   P   Y   W   T   N   T
```

FIG. 12B

```
       430          440         450         460         470         480         490
GAAAAGATGGAAAAAGCGGCTCCATGCTGTGCCTGCGGCCAACACTGTCAAGTTTCGCTGCCCAGCCGGGG
 E  K  M  E  K  R  L  H  A  V  P  A  A  N  T  V  K  F  R  C  P  A  G 500          510         520         530         540         550         560
GGAACCCAATGCCAACCATGCGGGTGGCTGAAAAACGGGAAGGAGTTTAAGCAGGAGCATCGCATTGGAGG
 G  N  P  M  P  T  M  R  W  L  K  N  G  K  E  F  K  Q  E  H  R  I  G  G 570          580         590         600         610         620         630
CTACAAGGTACGAAACCAGCACTGGAGCCTCATTATGGAAAGTGTGGTCCCATCTGACAAGGAAATTAT
 Y  K  V  R  N  Q  H  W  S  L  I  M  E  S  V  V  P  S  D  K  G  N  Y 640          650         660         670         680         690         700
ACCTGTGTGGTGGAGAATGAATACGGGTCCATCAATCACACGTACCACCTGGATGTGTGGAGGATCGC
 T  C  V  V  E  N  E  Y  G  S  I  N  H  T  Y  H  L  D  V  V  E  R  S 710          720         730         740         750         760         770
CTCACCGGCCCATCCTCCAAGCCGGACTGCCTCCACAGTGGTCGGAGAGACGTAGAGTT
 P  H  R  P  I  L  Q  A  G  L  P  A  N  A  S  T  V  V  G  G  D  V  E  F 780          790         800         810         820         830         840
TGTCTGCAAGGTTTACAGTGATGCCCAGCCCACATCCAGTGGATCAAGCACGTGGAAAAGAACGGCAGT
 V  C  K  V  Y  S  D  A  Q  P  H  I  Q  W  I  K  H  V  E  K  N  G  S 850          860         870         880         890         900         910
AAATACGGGCCCGACGGGCTGCCCTACCTCAAGGTTCTCAAGCACTCGGGGATAAATAGTTCCAATGCAG
 K  Y  G  P  D  G  L  P  Y  L  K  V  L  K  H  S  G  I  N  S  S  N  A
```

FIG. 12C

```
      920         930         940         950         960         970         980
AAGTGCTGGCTCTGTTCAATGTGACCGAGGCGGATCCGGGGGAATATATGTAAGGTCTCCAATTATAT
 E  V  L  A  L  F  N  V  T  E  A  D  A  G  E  Y  I  C  K  V  S  N  Y  I 990        1000        1010        1020        1030        1040        1050
AGGGCAGGCCAACCAGTCTGCTGGCTCTCACTGTCCTGCCAAAACAGCAAGGCCTGGAAGAGAAAGGAG
 G  Q  A  N  Q  S  A  W  L  T  V  L  P  K  Q  Q  A  P  G  R  E  K  E 1060        1070
ATTACAGCTTCCCCAGACTAACTGGATCC
 I  T  A  S  P  D
```

5,750,371

SEQUENCE LISTING ( 1 ) GENERAL INFORMATION:

( i i i ) NUMBER OF SEQUENCES: 18

( 2 ) INFORMATION FOR SEQ ID NO:1:

( i ) SEQUENCE CHARACTERISTICS:
( A ) LENGTH: 605 base pairs
( B ) TYPE: nucleic acid
( C ) STRANDEDNESS: double
( D ) TOPOLOGY: linear ( i i ) MOLECULE TYPE: cDNA ( i x ) FEATURE:
( A ) NAME/KEY: CDS
( B ) LOCATION: 2..604

( x i ) SEQUENCE DESCRIPTION: SEQ ID NO:1:

```
C ACC CCG CTG GTG AGG ATA ACA ACA CGC CTC TCT TCA ACG GCA GAC        46
  Thr Pro Leu Val Arg Ile Thr Thr Arg Leu Ser Ser Thr Ala Asp
  1               5                  10                  15

ACC CCC ATG CTG GCA GGG GTC TCC GAG TAT GAA CTT CCA GAG GAC CCA      94
Thr Pro Met Leu Ala Gly Val Ser Glu Tyr Glu Leu Pro Glu Asp Pro
                20                  25                  30

AAA TGG GAG TTT CCA AGA GAT AAG CTG ACA CTG GGC AAG CCC CTG GGA     142
Lys Trp Glu Phe Pro Arg Asp Lys Leu Thr Leu Gly Lys Pro Leu Gly
            35                  40                  45

GAA GGT TGC TTT GGG CAA GTG GTC ATG GCG GAA GCA GTG GGA ATT GAC     190
Glu Gly Cys Phe Gly Gln Val Val Met Ala Glu Ala Val Gly Ile Asp
```

|     |     |     |     | 50  |     |     |     |     | 55  |     |     |     |     | 60  |     |     |
| --- | --- | --- | --- | --- | --- | --- | --- | --- | --- | --- | --- | --- | --- | --- | --- | --- |
| AAA | GAC | AAG | CCC | AAG | GAG | GCG | GTC | ACC | GTG | GCC | GTG | AAG | ATG | TTG | AAA | 238 |
| Lys | Asp | Lys | Pro | Lys | Glu | Ala | Val | Thr | Val | Ala | Val | Lys | Met | Leu | Lys |     |
|     |     | 65  |     |     |     |     | 70  |     |     |     |     | 75  |     |     |     |     |
| GAT | GAT | GCC | ACA | GAG | AAA | GAC | CTT | TCT | GAT | CTG | GTG | TCA | GAG | ATG | GAG | 286 |
| Asp | Asp | Ala | Thr | Glu | Lys | Asp | Leu | Ser | Asp | Leu | Val | Ser | Glu | Met | Glu |     |
| 80  |     |     |     |     | 85  |     |     |     |     | 90  |     |     |     |     | 95  |     |
| ATG | ATG | AAG | ATG | ATT | GGG | AAA | CAC | AAG | AAT | ATC | ATA | AAT | CTT | CTT | GGA | 334 |
| Met | Met | Lys | Met | Ile | Gly | Lys | His | Lys | Asn | Ile | Ile | Asn | Leu | Leu | Gly |     |
|     |     |     |     | 100 |     |     |     |     | 105 |     |     |     |     | 110 |     |     |
| GCC | TGC | ACA | CAG | GAT | GGG | CCT | CTC | TAT | GTC | ATA | GTT | GAG | TAT | GCC | TCT | 382 |
| Ala | Cys | Thr | Gln | Asp | Gly | Pro | Leu | Tyr | Val | Ile | Val | Glu | Tyr | Ala | Ser |     |
|     |     |     | 115 |     |     |     |     | 120 |     |     |     |     | 125 |     |     |     |
| AAA | GGC | AAC | CTC | CGA | GAA | TAC | CTC | CGA | GCC | CGG | AGG | CCA | CCC | GGG | ATG | 430 |
| Lys | Gly | Asn | Leu | Arg | Glu | Tyr | Leu | Arg | Ala | Arg | Arg | Pro | Pro | Gly | Met |     |
|     |     | 130 |     |     |     |     | 135 |     |     |     |     | 140 |     |     |     |     |
| CAG | TAC | TCC | TAT | GAC | ATT | AAC | CGT | GTT | CCT | GAG | GAG | CAG | ATG | ACC | TTC | 478 |
| Gln | Tyr | Ser | Tyr | Asp | Ile | Asn | Arg | Val | Pro | Glu | Glu | Gln | Met | Thr | Phe |     |
|     |     | 145 |     |     |     |     | 150 |     |     |     |     | 155 |     |     |     |     |
| AAG | GAC | TTG | GTG | TCA | TGC | ACC | TAC | CAG | CTG | GCC | AGA | GGC | ATG | GAG | TAC | 526 |
| Lys | Asp | Leu | Val | Ser | Cys | Thr | Tyr | Gln | Leu | Ala | Arg | Gly | Met | Glu | Tyr |     |
| 160 |     |     |     |     | 165 |     |     |     |     | 170 |     |     |     |     | 175 |     |
| TTG | GCT | TCC | CAA | AAA | TGT | ATT | CAT | CGA | GAT | TTA | GCA | GCC | AGA | AAT | GTT | 574 |
| Leu | Ala | Ser | Gln | Lys | Cys | Ile | His | Arg | Asp | Leu | Ala | Ala | Arg | Asn | Val |     |
|     |     |     |     | 180 |     |     |     |     | 185 |     |     |     |     | 190 |     |     |
| TTG | GTA | ACA | GAA | AAC | AAT | GTG | ATG | AAA | ATA | G   |     |     |     |     |     | 605 |
| Leu | Val | Thr | Glu | Asn | Asn | Val | Met | Lys | Ile |     |     |     |     |     |     |     |
|     |     |     |     | 195 |     |     |     |     | 200 |     |     |     |     |     |     |     |

( 2 ) INFORMATION FOR SEQ ID NO:2:

( i ) SEQUENCE CHARACTERISTICS:
        ( A ) LENGTH: 201 amino acids
        ( B ) TYPE: amino acid
        ( D ) TOPOLOGY: linear ( i i ) MOLECULE TYPE: protein ( x i ) SEQUENCE DESCRIPTION: SEQ ID NO:2:

| Thr | Pro | Leu | Val | Arg | Ile | Thr | Thr | Arg | Leu | Ser | Ser | Thr | Ala | Asp | Thr |
| --- | --- | --- | --- | --- | --- | --- | --- | --- | --- | --- | --- | --- | --- | --- | --- |
| 1   |     |     |     | 5   |     |     |     |     | 10  |     |     |     |     | 15  |     |
| Pro | Met | Leu | Ala | Gly | Val | Ser | Glu | Tyr | Glu | Leu | Pro | Glu | Asp | Pro | Lys |
|     |     |     | 20  |     |     |     |     | 25  |     |     |     |     | 30  |     |     |
| Trp | Glu | Phe | Pro | Arg | Asp | Lys | Leu | Thr | Leu | Gly | Lys | Pro | Leu | Gly | Glu |
|     |     | 35  |     |     |     |     | 40  |     |     |     |     | 45  |     |     |     |
| Gly | Cys | Phe | Gly | Gln | Val | Val | Met | Ala | Glu | Ala | Val | Gly | Ile | Asp | Lys |
|     | 50  |     |     |     |     | 55  |     |     |     |     | 60  |     |     |     |     |
| Asp | Lys | Pro | Lys | Glu | Ala | Val | Thr | Val | Ala | Val | Lys | Met | Leu | Lys | Asp |
| 65  |     |     |     |     | 70  |     |     |     |     | 75  |     |     |     |     | 80  |
| Asp | Ala | Thr | Glu | Lys | Asp | Leu | Ser | Asp | Leu | Val | Ser | Glu | Met | Glu | Met |
|     |     |     |     | 85  |     |     |     |     | 90  |     |     |     |     | 95  |     |
| Met | Lys | Met | Ile | Gly | Lys | His | Lys | Asn | Ile | Ile | Asn | Leu | Leu | Gly | Ala |
|     |     |     | 100 |     |     |     |     | 105 |     |     |     |     | 110 |     |     |
| Cys | Thr | Gln | Asp | Gly | Pro | Leu | Tyr | Val | Ile | Val | Glu | Tyr | Ala | Ser | Lys |
|     |     | 115 |     |     |     |     | 120 |     |     |     |     | 125 |     |     |     |
| Gly | Asn | Leu | Arg | Glu | Tyr | Leu | Arg | Ala | Arg | Arg | Pro | Pro | Gly | Met | Gln |
|     | 130 |     |     |     |     | 135 |     |     |     |     | 140 |     |     |     |     |
| Tyr | Ser | Tyr | Asp | Ile | Asn | Arg | Val | Pro | Glu | Glu | Gln | Met | Thr | Phe | Lys |
| 145 |     |     |     |     | 150 |     |     |     |     | 155 |     |     |     |     | 160 |

```
Asp Leu Val Ser Cys Thr Tyr Gln Leu Ala Arg Gly Met Glu Tyr Leu
            165                 170                 175

Ala Ser Gln Lys Cys Ile His Arg Asp Leu Ala Ala Arg Asn Val Leu
            180                 185                 190

Val Thr Glu Asn Asn Val Met Lys Ile
            195                 200
```

( 2 ) INFORMATION FOR SEQ ID NO:3:

( i ) SEQUENCE CHARACTERISTICS:
        ( A ) LENGTH: 1603 base pairs
        ( B ) TYPE: nucleic acid
        ( C ) STRANDEDNESS: double
        ( D ) TOPOLOGY: linear ( i i ) MOLECULE TYPE: cDNA ( i x ) FEATURE:
        ( A ) NAME/KEY: CDS
        ( B ) LOCATION: 25..1602

( x i ) SEQUENCE DESCRIPTION: SEQ ID NO:3:

```
GGACCGGGGA TTGGTACCGT AACC ATG GTC AGC TGG GGT CGT TTC ATC TGC       51
                           Met Val Ser Trp Gly Arg Phe Ile Cys
                            1               5

CTG GTC GTG GTC ACC ATG GCA ACC TTG TCC CTG GCC CGG CCC TCC TTC      99
Leu Val Val Val Thr Met Ala Thr Leu Ser Leu Ala Arg Pro Ser Phe
 10              15                  20                  25

AGT TTA GTT GAG GAT ACC ACA TTA GAG CCA GAA GGA GCA CCA TAC TGG     147
Ser Leu Val Glu Asp Thr Thr Leu Glu Pro Glu Gly Ala Pro Tyr Trp
             30                  35                  40

ACC AAC ACA GAA AAG ATG GAA AAG CGG CTC CAT GCT GTG CCT GCG GCC     195
Thr Asn Thr Glu Lys Met Glu Lys Arg Leu His Ala Val Pro Ala Ala
                 45                  50                  55

AAC ACT GTC AAG TTT CGC TGC CCA GCC GGG GGG AAC CCA ATG CCA ACC     243
Asn Thr Val Lys Phe Arg Cys Pro Ala Gly Gly Asn Pro Met Pro Thr
             60                  65                  70

ATG CGG TGG CTG AAA AAC GGG AAG GAG TTT AAG CAG GAG CAT CGC ATT     291
Met Arg Trp Leu Lys Asn Gly Lys Glu Phe Lys Gln Glu His Arg Ile
         75                  80                  85

GGA GGC TAC AAG GTA CGA AAC CAG CAC TGG AGC CTC ATT ATG GAA AGT     339
Gly Gly Tyr Lys Val Arg Asn Gln His Trp Ser Leu Ile Met Glu Ser
 90                  95                 100                 105

GTG GTC CCA TCT GAC AAG GGA AAT TAT ACC TGT GTG GTG GAG AAT GAA     387
Val Val Pro Ser Asp Lys Gly Asn Tyr Thr Cys Val Val Glu Asn Glu
             110                 115                 120

TAC GGG TCC ATC AAT CAC ACG TAC CAC CTG GAT GTT GTG GAG CGA TCG     435
Tyr Gly Ser Ile Asn His Thr Tyr His Leu Asp Val Val Glu Arg Ser
                 125                 130                 135

CCT CAC CGG CCC ATC CTC CAA GCC GGA CTG CCG GCA AAT GCC TCC ACA     483
Pro His Arg Pro Ile Leu Gln Ala Gly Leu Pro Ala Asn Ala Ser Thr
             140                 145                 150

GTG GTC GGA GGA GAC GTA GAG TTT GTC TGC AAG GTT TAC AGT GAT GCC     531
Val Val Gly Gly Asp Val Glu Phe Val Cys Lys Val Tyr Ser Asp Ala
 155                 160                 165

CAG CCC CAC ATC CAG TGG ATC AAG CAC GTG GAA AAG AAC GGC AGT AAA     579
Gln Pro His Ile Gln Trp Ile Lys His Val Glu Lys Asn Gly Ser Lys
170                 175                 180                 185

TAC GGG CCC GAC GGG CTG CCC TAC CTC AAG GTT CTC AAG CAC TCG GGG     627
Tyr Gly Pro Asp Gly Leu Pro Tyr Leu Lys Val Leu Lys His Ser Gly
             190                 195                 200

ATA AAT AGT TCC AAT GCA GAA GTG CTG GCT CTG TTC AAT GTG ACC GAG     675
Ile Asn Ser Ser Asn Ala Glu Val Leu Ala Leu Phe Asn Val Thr Glu
```

|     |     |     |     |     |     |     |     |     |     |     |     |     |     |     |     |
| --- | --- | --- | --- | --- | --- | --- | --- | --- | --- | --- | --- | --- | --- | --- | --- |
|     |     | 205 |     |     |     |     | 210 |     |     |     |     | 215 |     |     |     |
| GCG | GAT | GCT | GGG | GAA | TAT | ATA | TGT | AAG | GTC | TCC | AAT | TAT | ATA | GGG | CAG | 723 |
| Ala | Asp | Ala | Gly | Glu | Tyr | Ile | Cys | Lys | Val | Ser | Asn | Tyr | Ile | Gly | Gln |
|     |     | 220 |     |     |     |     | 225 |     |     |     |     | 230 |     |     |     |
| GCC | AAC | CAG | TCT | GCC | TGG | CTC | ACT | GTC | CTG | CCA | AAA | CAG | CAA | GCG | CCT | 771 |
| Ala | Asn | Gln | Ser | Ala | Trp | Leu | Thr | Val | Leu | Pro | Lys | Gln | Gln | Ala | Pro |
|     |     | 235 |     |     |     |     | 240 |     |     |     |     | 245 |     |     |     |
| GGA | AGA | GAA | AAG | GAG | ATT | ACA | GCT | TCC | CCA | GAC | TAC | CTG | GAG | ATA | GCC | 819 |
| Gly | Arg | Glu | Lys | Glu | Ile | Thr | Ala | Ser | Pro | Asp | Tyr | Leu | Glu | Ile | Ala |
| 250 |     |     |     |     | 255 |     |     |     |     | 260 |     |     |     |     | 265 |
| ATT | TAC | TGC | ATA | GGG | GTC | TTC | TTA | ATC | GCC | TGT | ATG | GTG | GTA | ACA | GTC | 867 |
| Ile | Tyr | Cys | Ile | Gly | Val | Phe | Leu | Ile | Ala | Cys | Met | Val | Val | Thr | Val |
|     |     |     |     | 270 |     |     |     |     | 275 |     |     |     |     | 280 |     |
| ATC | CTG | TGC | CGA | ATG | AAG | AAC | ACG | ACC | AAG | AAG | CCA | GAC | TTC | AGC | AGC | 915 |
| Ile | Leu | Cys | Arg | Met | Lys | Asn | Thr | Thr | Lys | Lys | Pro | Asp | Phe | Ser | Ser |
|     |     |     | 285 |     |     |     |     | 290 |     |     |     |     | 295 |     |     |
| CAG | CCG | GCT | GTG | CAC | AAG | CTG | ACC | AAA | CGT | ATC | CCC | CTG | CGG | AGA | CAG | 963 |
| Gln | Pro | Ala | Val | His | Lys | Leu | Thr | Lys | Arg | Ile | Pro | Leu | Arg | Arg | Gln |
|     |     | 300 |     |     |     |     | 305 |     |     |     |     | 310 |     |     |     |
| GTT | TCG | GCT | GAG | TCC | AGC | TCC | TCC | ATG | AAC | TCC | AAC | ACC | CCG | CTG | GTG | 1011 |
| Val | Ser | Ala | Glu | Ser | Ser | Ser | Ser | Met | Asn | Ser | Asn | Thr | Pro | Leu | Val |
|     | 315 |     |     |     |     | 320 |     |     |     |     | 325 |     |     |     |     |
| AGG | ATA | ACA | ACA | CGC | CTC | TCT | TCA | ACG | GCA | GAC | ACC | CCC | ATG | CTG | GCA | 1059 |
| Arg | Ile | Thr | Thr | Arg | Leu | Ser | Ser | Thr | Ala | Asp | Thr | Pro | Met | Leu | Ala |
| 330 |     |     |     |     | 335 |     |     |     |     | 340 |     |     |     |     | 345 |
| GGG | GTC | TCC | GAG | TAT | GAA | CTT | CCA | GAG | GAC | CCA | AAA | TGG | GAG | TTT | CCA | 1107 |
| Gly | Val | Ser | Glu | Tyr | Glu | Leu | Pro | Glu | Asp | Pro | Lys | Trp | Glu | Phe | Pro |
|     |     |     |     | 350 |     |     |     |     | 355 |     |     |     |     | 360 |     |
| AGA | GAT | AAG | CTG | ACA | CTG | GGC | AAG | CCC | CTG | GGA | GAA | GGT | TGC | TTT | GGG | 1155 |
| Arg | Asp | Lys | Leu | Thr | Leu | Gly | Lys | Pro | Leu | Gly | Glu | Gly | Cys | Phe | Gly |
|     |     |     | 365 |     |     |     |     | 370 |     |     |     |     | 375 |     |     |
| CAA | GTG | GTC | ATG | GCG | GAA | GCA | GTG | GGA | ATT | GAC | AAA | GAC | AAG | CCC | AAG | 1203 |
| Gln | Val | Val | Met | Ala | Glu | Ala | Val | Gly | Ile | Asp | Lys | Asp | Lys | Pro | Lys |
|     |     | 380 |     |     |     |     | 385 |     |     |     |     | 390 |     |     |     |
| GAG | GCG | GTC | ACC | GTG | GCC | GTG | AAG | ATG | TTG | AAA | GAT | GAT | GCC | ACA | GAG | 1251 |
| Glu | Ala | Val | Thr | Val | Ala | Val | Lys | Met | Leu | Lys | Asp | Asp | Ala | Thr | Glu |
|     | 395 |     |     |     |     | 400 |     |     |     |     | 405 |     |     |     |     |
| AAA | GAC | CTT | TCT | GAT | CTG | GTG | TCA | GAG | ATG | GAG | ATG | ATG | AAG | ATG | ATT | 1299 |
| Lys | Asp | Leu | Ser | Asp | Leu | Val | Ser | Glu | Met | Glu | Met | Met | Lys | Met | Ile |
| 410 |     |     |     |     | 415 |     |     |     |     | 420 |     |     |     |     | 425 |
| GGG | AAA | CAC | AAG | AAT | ATC | ATA | AAT | CTT | CTT | GGA | GCC | TGC | ACA | CAG | GAT | 1347 |
| Gly | Lys | His | Lys | Asn | Ile | Ile | Asn | Leu | Leu | Gly | Ala | Cys | Thr | Gln | Asp |
|     |     |     |     | 430 |     |     |     |     | 435 |     |     |     |     | 440 |     |
| GGG | CCT | CTC | TAT | GTC | ATA | GTT | GAG | TAT | GCC | TCT | AAA | GGC | AAC | CTC | CGA | 1395 |
| Gly | Pro | Leu | Tyr | Val | Ile | Val | Glu | Tyr | Ala | Ser | Lys | Gly | Asn | Leu | Arg |
|     |     |     | 445 |     |     |     |     | 450 |     |     |     |     | 455 |     |     |
| GAA | TAC | CTC | CGA | GCC | CGG | AGG | CCA | CCC | GGG | ATG | GAG | TAC | TCC | TAT | GAC | 1443 |
| Glu | Tyr | Leu | Arg | Ala | Arg | Arg | Pro | Pro | Gly | Met | Glu | Tyr | Ser | Tyr | Asp |
|     |     | 460 |     |     |     |     | 465 |     |     |     |     | 470 |     |     |     |
| ATT | AAC | CGT | GTT | CCT | GAG | GAG | CAG | ATG | ACC | TTC | AAG | GAC | TTG | GTG | TCA | 1491 |
| Ile | Asn | Arg | Val | Pro | Glu | Glu | Gln | Met | Thr | Phe | Lys | Asp | Leu | Val | Ser |
|     |     | 475 |     |     |     |     | 480 |     |     |     |     | 485 |     |     |     |
| TGC | ACC | TAC | CAG | CTG | GCC | AGA | GGC | ATG | GAG | TAC | TTG | GCT | TCC | CAA | AAA | 1539 |
| Cys | Thr | Tyr | Gln | Leu | Ala | Arg | Gly | Met | Glu | Tyr | Leu | Ala | Ser | Gln | Lys |
| 490 |     |     |     |     | 495 |     |     |     |     | 500 |     |     |     |     | 505 |
| TGT | ATT | CAT | CGA | GAT | TTA | GCA | GCC | AGA | AAT | GTT | TTG | GTA | ACA | GAA | AAC | 1587 |
| Cys | Ile | His | Arg | Asp | Leu | Ala | Ala | Arg | Asn | Val | Leu | Val | Thr | Glu | Asn |
|     |     |     |     | 510 |     |     |     |     | 515 |     |     |     |     | 520 |     |
| AAT | GTG | ATG | AAA | ATA | G   |     |     |     |     |     |     |     |     |     |     | 1603 |
| Asn | Val | Met | Lys | Ile |     |     |     |     |     |     |     |     |     |     |     |

525

( 2 ) INFORMATION FOR SEQ ID NO:4:

( i ) SEQUENCE CHARACTERISTICS:
　　　　( A ) LENGTH: 526 amino acids
　　　　( B ) TYPE: amino acid
　　　　( D ) TOPOLOGY: linear ( i i ) MOLECULE TYPE: protein ( x i ) SEQUENCE DESCRIPTION: SEQ ID NO:4:

| Met | Val | Ser | Trp | Gly | Arg | Phe | Ile | Cys | Leu | Val | Val | Thr | Met | Ala |
|---|---|---|---|---|---|---|---|---|---|---|---|---|---|---|
| 1 | | | | 5 | | | | | 10 | | | | | 15 |
| Thr | Leu | Ser | Leu | Ala | Arg | Pro | Ser | Phe | Ser | Leu | Val | Glu | Asp | Thr | Thr |
| | | | 20 | | | | | 25 | | | | | 30 | | |
| Leu | Glu | Pro | Glu | Gly | Ala | Pro | Tyr | Trp | Thr | Asn | Thr | Glu | Lys | Met | Glu |
| | | 35 | | | | | 40 | | | | | 45 | | | |
| Lys | Arg | Leu | His | Ala | Val | Pro | Ala | Ala | Asn | Thr | Val | Lys | Phe | Arg | Cys |
| | 50 | | | | | 55 | | | | | 60 | | | | |
| Pro | Ala | Gly | Gly | Asn | Pro | Met | Pro | Thr | Met | Arg | Trp | Leu | Lys | Asn | Gly |
| 65 | | | | | 70 | | | | | 75 | | | | | 80 |
| Lys | Glu | Phe | Lys | Gln | Glu | His | Arg | Ile | Gly | Gly | Tyr | Lys | Val | Arg | Asn |
| | | | | 85 | | | | | 90 | | | | | 95 | |
| Gln | His | Trp | Ser | Leu | Ile | Met | Glu | Ser | Val | Val | Pro | Ser | Asp | Lys | Gly |
| | | | | 100 | | | | | 105 | | | | | 110 | |
| Asn | Tyr | Thr | Cys | Val | Val | Glu | Asn | Glu | Tyr | Gly | Ser | Ile | Asn | His | Thr |
| | | | 115 | | | | | 120 | | | | | 125 | | |
| Tyr | His | Leu | Asp | Val | Val | Glu | Arg | Ser | Pro | His | Arg | Pro | Ile | Leu | Gln |
| | 130 | | | | | 135 | | | | | 140 | | | | |
| Ala | Gly | Leu | Pro | Ala | Asn | Ala | Ser | Thr | Val | Val | Gly | Gly | Asp | Val | Glu |
| 145 | | | | | 150 | | | | | 155 | | | | | 160 |
| Phe | Val | Cys | Lys | Val | Tyr | Ser | Asp | Ala | Gln | Pro | His | Ile | Gln | Trp | Ile |
| | | | | 165 | | | | | 170 | | | | | 175 | |
| Lys | His | Val | Glu | Lys | Asn | Gly | Ser | Lys | Tyr | Gly | Pro | Asp | Gly | Leu | Pro |
| | | | | 180 | | | | | 185 | | | | | 190 | |
| Tyr | Leu | Lys | Val | Leu | Lys | His | Ser | Gly | Ile | Asn | Ser | Ser | Asn | Ala | Glu |
| | | | 195 | | | | | 200 | | | | | 205 | | |
| Val | Leu | Ala | Leu | Phe | Asn | Val | Thr | Glu | Ala | Asp | Ala | Gly | Glu | Tyr | Ile |
| | | 210 | | | | | 215 | | | | | 220 | | | |
| Cys | Lys | Val | Ser | Asn | Tyr | Ile | Gly | Gln | Ala | Asn | Gln | Ser | Ala | Trp | Leu |
| 225 | | | | | 230 | | | | | 235 | | | | | 240 |
| Thr | Val | Leu | Pro | Lys | Gln | Gln | Ala | Pro | Gly | Arg | Glu | Lys | Glu | Ile | Thr |
| | | | | 245 | | | | | 250 | | | | | 255 | |
| Ala | Ser | Pro | Asp | Tyr | Leu | Glu | Ile | Ala | Ile | Tyr | Cys | Ile | Gly | Val | Phe |
| | | | 260 | | | | | 265 | | | | | 270 | | |
| Leu | Ile | Ala | Cys | Met | Val | Val | Thr | Val | Ile | Leu | Cys | Arg | Met | Lys | Asn |
| | | | 275 | | | | | 280 | | | | | 285 | | |
| Thr | Thr | Lys | Lys | Pro | Asp | Phe | Ser | Ser | Gln | Pro | Ala | Val | His | Lys | Leu |
| | 290 | | | | | 295 | | | | | 300 | | | | |
| Thr | Lys | Arg | Ile | Pro | Leu | Arg | Arg | Gln | Val | Ser | Ala | Glu | Ser | Ser | Ser |
| 305 | | | | | 310 | | | | | 315 | | | | | 320 |
| Ser | Met | Asn | Ser | Asn | Thr | Pro | Leu | Val | Arg | Ile | Thr | Thr | Arg | Leu | Ser |
| | | | | 325 | | | | | 330 | | | | | 335 | |
| Ser | Thr | Ala | Asp | Thr | Pro | Met | Leu | Ala | Gly | Val | Ser | Glu | Tyr | Glu | Leu |
| | | | 340 | | | | | 345 | | | | | 350 | | |

```
Pro  Glu  Asp  Pro  Lys  Trp  Glu  Phe  Pro  Arg  Asp  Lys  Leu  Thr  Leu  Gly
          355                      360                 365

Lys  Pro  Leu  Gly  Glu  Gly  Cys  Phe  Gly  Gln  Val  Val  Met  Ala  Glu  Ala
     370                      375                 380

Val  Gly  Ile  Asp  Lys  Asp  Lys  Pro  Lys  Glu  Ala  Val  Thr  Val  Ala  Val
385                      390                 395                           400

Lys  Met  Leu  Lys  Asp  Asp  Ala  Thr  Glu  Lys  Asp  Leu  Ser  Asp  Leu  Val
               405                      410                 415

Ser  Glu  Met  Glu  Met  Met  Lys  Met  Ile  Gly  Lys  His  Lys  Asn  Ile  Ile
               420                      425                 430

Asn  Leu  Leu  Gly  Ala  Cys  Thr  Gln  Asp  Gly  Pro  Leu  Tyr  Val  Ile  Val
          435                      440                 445

Glu  Tyr  Ala  Ser  Lys  Gly  Asn  Leu  Arg  Glu  Tyr  Leu  Arg  Ala  Arg  Arg
     450                      455                 460

Pro  Pro  Gly  Met  Glu  Tyr  Ser  Tyr  Asp  Ile  Asn  Arg  Val  Pro  Glu  Glu
465                      470                 475                           480

Gln  Met  Thr  Phe  Lys  Asp  Leu  Val  Ser  Cys  Thr  Tyr  Gln  Leu  Ala  Arg
               485                      490                 495

Gly  Met  Glu  Tyr  Leu  Ala  Ser  Gln  Lys  Cys  Ile  His  Arg  Asp  Leu  Ala
               500                      505                 510

Ala  Arg  Asn  Val  Leu  Val  Thr  Glu  Asn  Asn  Val  Met  Lys  Ile
          515                      520                 525
```

(2) INFORMATION FOR SEQ ID NO:5:

(i) SEQUENCE CHARACTERISTICS:
        (A) LENGTH: 1954 base pairs
        (B) TYPE: nucleic acid
        (C) STRANDEDNESS: double
        (D) TOPOLOGY: linear (ii) MOLECULE TYPE: cDNA (ix) FEATURE:
        (A) NAME/KEY: CDS
        (B) LOCATION: 25..1953

(xi) SEQUENCE DESCRIPTION: SEQ ID NO:5:

```
GGACCGGGGA TTGGTACCGT AACC ATG GTC AGC TGG GGT CGT TTC ATC TGC         51
                          Met Val Ser Trp Gly Arg Phe Ile Cys
                            1               5

CTG GTC GTG GTC ACC ATG GCA ACC TTG TCC CTG GCC CGG CCC TCC TTC        99
Leu Val Val Val Thr Met Ala Thr Leu Ser Leu Ala Arg Pro Ser Phe
 10              15                  20                      25

AGT TTA GTT GAG GAT ACC ACA TTA GAG CCA GAA GAG CCA CCA ACC AAA       147
Ser Leu Val Glu Asp Thr Thr Leu Glu Pro Glu Glu Pro Pro Thr Lys
                 30              35                  40

TAC CAA ATC TCT CAA CCA GAA GTG TAC GTG GCT GCG CCA GGG GAG TCG       195
Tyr Gln Ile Ser Gln Pro Glu Val Tyr Val Ala Ala Pro Gly Glu Ser
             45              50                  55

CTA GAG GTG CGC TGC CTG TTG AAA GAT GCC GCC GTG ATC AGT TGG ACT       243
Leu Glu Val Arg Cys Leu Leu Lys Asp Ala Ala Val Ile Ser Trp Thr
         60              65                  70

AAG GAT GGG GTG CAC TTG GGG CCC AAC AAT AGG ACA GTG CTT ATT GGG       291
Lys Asp Gly Val His Leu Gly Pro Asn Asn Arg Thr Val Leu Ile Gly
     75              80                  85

GAG TAC TTG CAG ATA AAG GGC GCC ACG CCT AGA GAC TCC GGC CTC TAT       339
Glu Tyr Leu Gln Ile Lys Gly Ala Thr Pro Arg Asp Ser Gly Leu Tyr
 90              95                 100                     105

GCT TGT ACT GCC AGT AGG ACT GTA GAC AGT GAA ACT TGG TAC TTC ATG       387
Ala Cys Thr Ala Ser Arg Thr Val Asp Ser Glu Thr Trp Tyr Phe Met
```

|  | 110 |  |  |  | 115 |  |  |  | 120 |  |  |  |  |
|---|---|---|---|---|---|---|---|---|---|---|---|---|---|

```
GTG  AAT  GTC  ACA  GAT  GCC  ATC  TCA  TCC  GGA  GAT  GAT  GAG  GAT  GAC  ACC       435
Val  Asn  Val  Thr  Asp  Ala  Ile  Ser  Ser  Gly  Asp  Asp  Glu  Asp  Asp  Thr
               125                130                     135

GAT  GGT  GCG  GAA  GAT  TTT  GTC  AGT  GAG  AAC  AGT  AAC  AAC  AAG  AGA  GCA       483
Asp  Gly  Ala  Glu  Asp  Phe  Val  Ser  Glu  Asn  Ser  Asn  Asn  Lys  Arg  Ala
               140                145                     150

CCA  TAC  TGG  ACC  AAC  ACA  GAA  AAG  ATG  GAA  AAG  CGG  CTC  CAT  GCT  GTG       531
Pro  Tyr  Trp  Thr  Asn  Thr  Glu  Lys  Met  Glu  Lys  Arg  Leu  His  Ala  Val
          155                     160                     165

CCT  GCG  GCC  AAC  ACT  GTC  AAG  TTT  CGC  TGC  CCA  GCC  GGG  GGG  AAC  CCA       579
Pro  Ala  Ala  Asn  Thr  Val  Lys  Phe  Arg  Cys  Pro  Ala  Gly  Gly  Asn  Pro
170                      175                     180                          185

ATG  CCA  ACC  ATG  CGG  TGG  CTG  AAA  AAC  GGG  AAG  GAG  TTT  AAG  CAG  GAG       627
Met  Pro  Thr  Met  Arg  Trp  Leu  Lys  Asn  Gly  Lys  Glu  Phe  Lys  Gln  Glu
                    190                     195                          200

CAT  CGC  ATT  GGA  GGC  TAC  AAG  GTA  CGA  AAC  CAG  CAC  TGG  AGC  CTC  ATT       675
His  Arg  Ile  Gly  Gly  Tyr  Lys  Val  Arg  Asn  Gln  His  Trp  Ser  Leu  Ile
                    205                     210                          215

ATG  GAA  AGT  GTG  GTC  CCA  TCT  GAC  AAG  GGA  AAT  TAT  ACC  TGT  GTG  GTG       723
Met  Glu  Ser  Val  Val  Pro  Ser  Asp  Lys  Gly  Asn  Tyr  Thr  Cys  Val  Val
               220                     225                     230

GAG  AAT  GAA  TAC  GGG  TCC  ATC  AAT  CAC  ACG  TAC  CAC  CTG  GAT  GTT  GTG       771
Glu  Asn  Glu  Tyr  Gly  Ser  Ile  Asn  His  Thr  Tyr  His  Leu  Asp  Val  Val
          235                     240                     245

GAG  CGA  TCG  CCT  CAC  CGG  CCC  ATC  CTC  CAA  GCC  GGA  CTG  CCG  GCA  AAT       819
Glu  Arg  Ser  Pro  His  Arg  Pro  Ile  Leu  Gln  Ala  Gly  Leu  Pro  Ala  Asn
250                      255                     260                          265

GCC  TCC  ACA  GTG  GTC  GGA  GGA  GAC  GTA  GAG  TTT  GTC  TGC  AAG  GTT  TAC       867
Ala  Ser  Thr  Val  Val  Gly  Gly  Asp  Val  Glu  Phe  Val  Cys  Lys  Val  Tyr
                    270                     275                          280

AGT  GAT  GCC  CAG  CCC  CAC  ATC  CAG  TGG  ATC  AAG  CAC  GTG  GAA  AAG  AAC       915
Ser  Asp  Ala  Gln  Pro  His  Ile  Gln  Trp  Ile  Lys  His  Val  Glu  Lys  Asn
               285                     290                     295

GGC  AGT  AAA  TAC  GGG  CCC  GAC  GGG  CTG  CCC  TAC  CTC  AAG  GTT  CTC  AAG       963
Gly  Ser  Lys  Tyr  Gly  Pro  Asp  Gly  Leu  Pro  Tyr  Leu  Lys  Val  Leu  Lys
          300                     305                     310

CAC  TCG  GGG  ATA  AAT  AGT  TCC  AAT  GCA  GAA  GTG  CTG  GCT  CTG  TTC  AAT      1011
His  Ser  Gly  Ile  Asn  Ser  Ser  Asn  Ala  Glu  Val  Leu  Ala  Leu  Phe  Asn
315                      320                     325

GTG  ACC  GAG  GCG  GAT  GCG  GGG  GAA  TAT  ATA  TGT  AAG  GTC  TCC  AAT  TAT      1059
Val  Thr  Glu  Ala  Asp  Ala  Gly  Glu  Tyr  Ile  Cys  Lys  Val  Ser  Asn  Tyr
330                      335                     340                          345

ATA  GGG  CAG  GCC  AAC  CAG  TCT  GCC  TGG  CTC  ACT  GTC  CTG  CCA  AAA  CAG      1107
Ile  Gly  Gln  Ala  Asn  Gln  Ser  Ala  Trp  Leu  Thr  Val  Leu  Pro  Lys  Gln
               350                     355                     360

CAA  GCG  CCT  GGA  AGA  GAA  AAG  GAG  ATT  ACA  GCT  TCC  CCA  GAC  TAC  CTG      1155
Gln  Ala  Pro  Gly  Arg  Glu  Lys  Glu  Ile  Thr  Ala  Ser  Pro  Asp  Tyr  Leu
          365                     370                     375

GAG  ATA  GCC  ATT  TAC  TGC  ATA  GGG  GTC  TTC  TTA  ATC  GCC  TGT  ATG  GTG      1203
Glu  Ile  Ala  Ile  Tyr  Cys  Ile  Gly  Val  Phe  Leu  Ile  Ala  Cys  Met  Val
               380                     385                     390

GTA  ACA  GTC  ATC  CTG  TGC  CGA  ATG  AAG  AAC  ACG  ACC  AAG  AAG  CCA  GAC      1251
Val  Thr  Val  Ile  Leu  Cys  Arg  Met  Lys  Asn  Thr  Thr  Lys  Lys  Pro  Asp
          395                     400                     405

TTC  AGC  AGC  CAG  CCG  GCT  GTG  CAC  AAG  CTG  ACC  AAA  CGT  ATC  CCC  CTG      1299
Phe  Ser  Ser  Gln  Pro  Ala  Val  His  Lys  Leu  Thr  Lys  Arg  Ile  Pro  Leu
410                      415                     420                          425

CGG  AGA  CAG  GTA  ACA  GTT  TCG  GCT  GAG  TCC  AGC  TCC  TCC  ATG  AAC  TCC      1347
Arg  Arg  Gln  Val  Thr  Val  Ser  Ala  Glu  Ser  Ser  Ser  Ser  Met  Asn  Ser
```

|     |     |     |     |     |     |     |     |     |     |     |     |     |     |     |     |      |
|-----|-----|-----|-----|-----|-----|-----|-----|-----|-----|-----|-----|-----|-----|-----|-----|------|
|     |     |     |     |     |     | 430 |     |     |     |     |     | 435 |     |     |     |      |
| AAC | ACC | CCG | CTG | GTG | AGG | ATA | ACA | ACA | CGC | CTC | TCT | TCA | ACG | GCA | GAC | 1395 |
| Asn | Thr | Pro | Leu | Val | Arg | Ile | Thr | Thr | Arg | Leu | Ser | Ser | Thr | Ala | Asp |      |
|     |     |     | 445 |     |     |     |     | 450 |     |     |     |     | 455 |     |     |      |
| ACC | CCC | ATG | CTG | GCA | GGG | GTC | TCC | GAG | TAT | GAA | CTT | CCA | GAG | GAC | CCA | 1443 |
| Thr | Pro | Met | Leu | Ala | Gly | Val | Ser | Glu | Tyr | Glu | Leu | Pro | Glu | Asp | Pro |      |
|     |     | 460 |     |     |     |     | 465 |     |     |     |     | 470 |     |     |     |      |
| AAA | TGG | GAG | TTT | CCA | AGA | GAT | AAG | CTG | ACA | CTG | GGC | AAG | CCC | CTG | GGA | 1491 |
| Lys | Trp | Glu | Phe | Pro | Arg | Asp | Lys | Leu | Thr | Leu | Gly | Lys | Pro | Leu | Gly |      |
|     | 475 |     |     |     |     | 480 |     |     |     |     | 485 |     |     |     |     |      |
| GAA | GGT | TGC | TTT | GGG | CAA | GTG | GTC | ATG | GCG | GAA | GCA | GTG | GGA | ATT | GAC | 1539 |
| Glu | Gly | Cys | Phe | Gly | Gln | Val | Val | Met | Ala | Glu | Ala | Val | Gly | Ile | Asp |      |
| 490 |     |     |     |     | 495 |     |     |     |     | 500 |     |     |     |     | 505 |      |
| AAA | GAC | AAG | CCC | AAG | GAG | GCG | GTC | ACC | GTG | GCC | GTG | AAG | ATG | TTG | AAA | 1587 |
| Lys | Asp | Lys | Pro | Lys | Glu | Ala | Val | Thr | Val | Ala | Val | Lys | Met | Leu | Lys |      |
|     |     |     |     | 510 |     |     |     |     | 515 |     |     |     |     | 520 |     |      |
| GAT | GAT | GCC | ACA | GAG | AAA | GAC | CTT | TCT | GAT | CTG | GTG | TCA | GAG | ATG | GAG | 1635 |
| Asp | Asp | Ala | Thr | Glu | Lys | Asp | Leu | Ser | Asp | Leu | Val | Ser | Glu | Met | Glu |      |
|     |     |     | 525 |     |     |     |     | 530 |     |     |     |     | 535 |     |     |      |
| ATG | ATG | AAG | ATG | ATT | GGG | AAA | CAC | AAG | AAT | ATC | ATA | AAT | CTT | CTT | GGA | 1683 |
| Met | Met | Lys | Met | Ile | Gly | Lys | His | Lys | Asn | Ile | Ile | Asn | Leu | Leu | Gly |      |
|     |     | 540 |     |     |     |     | 545 |     |     |     |     | 550 |     |     |     |      |
| GCC | TGC | ACA | CAG | GAT | GGG | CCT | CTC | TAT | GTC | ATA | GTT | GAG | TAT | GCC | TCT | 1731 |
| Ala | Cys | Thr | Gln | Asp | Gly | Pro | Leu | Tyr | Val | Ile | Val | Glu | Tyr | Ala | Ser |      |
|     | 555 |     |     |     |     | 560 |     |     |     |     | 565 |     |     |     |     |      |
| AAA | GGC | AAC | CTC | CGA | GAA | TAC | CTC | CGA | GCC | CGG | AGG | CCA | CCC | GGG | ATG | 1779 |
| Lys | Gly | Asn | Leu | Arg | Glu | Tyr | Leu | Arg | Ala | Arg | Arg | Pro | Pro | Gly | Met |      |
| 570 |     |     |     |     | 575 |     |     |     |     | 580 |     |     |     |     | 585 |      |
| GAG | TAC | TCC | TAT | GAC | ATT | AAC | CGT | GTT | CCT | GAG | GAG | CAG | ATG | ACC | TTC | 1827 |
| Glu | Tyr | Ser | Tyr | Asp | Ile | Asn | Arg | Val | Pro | Glu | Glu | Gln | Met | Thr | Phe |      |
|     |     |     |     | 590 |     |     |     |     | 595 |     |     |     |     | 600 |     |      |
| AAG | GAC | TTG | GTG | TCA | TGC | ACC | TAC | CAG | CTG | GCC | AGA | GGC | ATG | GAG | TAC | 1875 |
| Lys | Asp | Leu | Val | Ser | Cys | Thr | Tyr | Gln | Leu | Ala | Arg | Gly | Met | Glu | Tyr |      |
|     |     |     | 605 |     |     |     |     | 610 |     |     |     |     | 615 |     |     |      |
| TTG | GCT | TCC | CAA | AAA | TGT | ATT | CAT | CGA | GAT | TTA | GCA | GCC | AGA | AAT | GTT | 1923 |
| Leu | Ala | Ser | Gln | Lys | Cys | Ile | His | Arg | Asp | Leu | Ala | Ala | Arg | Asn | Val |      |
|     |     | 620 |     |     |     |     | 625 |     |     |     |     | 630 |     |     |     |      |
| TTG | GTA | ACA | GAA | AAC | AAT | GTG | ATG | AAA | ATA | G   |     |     |     |     |     | 1954 |
| Leu | Val | Thr | Glu | Asn | Asn | Val | Met | Lys | Ile |     |     |     |     |     |     |      |
|     | 635 |     |     |     |     | 640 |     |     |     |     |     |     |     |     |     |      |

( 2 ) INFORMATION FOR SEQ ID NO:6:

( i ) SEQUENCE CHARACTERISTICS:
        ( A ) LENGTH: 643 amino acids
        ( B ) TYPE: amino acid
        ( D ) TOPOLOGY: linear ( i i ) MOLECULE TYPE: protein ( x i ) SEQUENCE DESCRIPTION: SEQ ID NO:6:

| Met | Val | Ser | Trp | Gly | Arg | Phe | Ile | Cys | Leu | Val | Val | Thr | Met | Ala |
|-----|-----|-----|-----|-----|-----|-----|-----|-----|-----|-----|-----|-----|-----|-----|
| 1   |     |     |     | 5   |     |     |     |     | 10  |     |     |     |     | 15  |
| Thr | Leu | Ser | Leu | Ala | Arg | Pro | Ser | Phe | Ser | Leu | Val | Glu | Asp | Thr | Thr |
|     |     |     | 20  |     |     |     |     | 25  |     |     |     |     | 30  |     |     |
| Leu | Glu | Pro | Glu | Glu | Pro | Pro | Thr | Lys | Tyr | Gln | Ile | Ser | Gln | Pro | Glu |
|     |     | 35  |     |     |     |     | 40  |     |     |     |     | 45  |     |     |     |
| Val | Tyr | Val | Ala | Ala | Pro | Gly | Glu | Ser | Leu | Glu | Val | Arg | Cys | Leu | Leu |
|     | 50  |     |     |     |     | 55  |     |     |     |     | 60  |     |     |     |     |
| Lys | Asp | Ala | Ala | Val | Ile | Ser | Trp | Thr | Lys | Asp | Gly | Val | His | Leu | Gly |
| 65  |     |     |     |     | 70  |     |     |     |     | 75  |     |     |     |     | 80  |

| | | | | | | | | | | | | | | |
|---|---|---|---|---|---|---|---|---|---|---|---|---|---|---|
| Pro | Asn | Asn | Arg | Thr 85 | Val | Leu | Ile | Gly | Glu 90 | Tyr | Leu | Gln | Ile | Lys 95 | Gly |
| Ala | Thr | Pro | Arg 100 | Asp | Ser | Gly | Leu | Tyr 105 | Ala | Cys | Thr | Ala | Ser 110 | Arg | Thr |
| Val | Asp | Ser 115 | Glu | Thr | Trp | Tyr | Phe 120 | Met | Val | Asn | Val | Thr 125 | Asp | Ala | Ile |
| Ser | Ser 130 | Gly | Asp | Asp | Glu | Asp 135 | Thr | Asp | Gly | Ala 140 | Glu | Asp | Phe | Val |
| Ser 145 | Glu | Asn | Ser | Asn | Asn 150 | Lys | Arg | Ala | Pro | Tyr 155 | Trp | Thr | Asn | Thr | Glu 160 |
| Lys | Met | Glu | Lys | Arg 165 | Leu | His | Ala | Val | Pro 170 | Ala | Ala | Asn | Thr | Val 175 | Lys |
| Phe | Arg | Cys | Pro 180 | Ala | Gly | Gly | Asn | Pro 185 | Met | Pro | Thr | Met | Arg 190 | Trp | Leu |
| Lys | Asn | Gly 195 | Lys | Glu | Phe | Lys | Gln 200 | Glu | His | Arg | Ile | Gly 205 | Gly | Tyr | Lys |
| Val | Arg 210 | Asn | Gln | His | Trp | Ser 215 | Leu | Ile | Met | Glu | Ser 220 | Val | Val | Pro | Ser |
| Asp 225 | Lys | Gly | Asn | Tyr | Thr 230 | Cys | Val | Val | Glu | Asn 235 | Glu | Tyr | Gly | Ser | Ile 240 |
| Asn | His | Thr | Tyr | His 245 | Leu | Asp | Val | Val | Glu 250 | Arg | Ser | Pro | His 255 | Arg | Pro |
| Ile | Leu | Gln | Ala 260 | Gly | Leu | Pro | Ala | Asn 265 | Ala | Ser | Thr | Val 270 | Val | Gly | Gly |
| Asp | Val | Glu 275 | Phe | Val | Cys | Lys | Val 280 | Tyr | Ser | Asp | Ala | Gln 285 | Pro | His | Ile |
| Gln | Trp 290 | Ile | Lys | His | Val | Glu 295 | Lys | Asn | Gly | Ser | Lys 300 | Tyr | Gly | Pro | Asp |
| Gly 305 | Leu | Pro | Tyr | Leu | Lys 310 | Val | Leu | Lys | His | Ser 315 | Gly | Ile | Asn | Ser | Ser 320 |
| Asn | Ala | Glu | Val | Leu 325 | Ala | Leu | Phe | Asn | Val 330 | Thr | Glu | Ala | Asp | Ala 335 | Gly |
| Glu | Tyr | Ile | Cys 340 | Lys | Val | Ser | Asn | Tyr 345 | Ile | Gly | Gln | Ala | Asn 350 | Gln | Ser |
| Ala | Trp | Leu 355 | Thr | Val | Leu | Pro | Lys 360 | Gln | Gln | Ala | Pro | Gly 365 | Arg | Glu | Lys |
| Glu | Ile 370 | Thr | Ala | Ser | Pro | Asp 375 | Tyr | Leu | Glu | Ile | Ala 380 | Ile | Tyr | Cys | Ile |
| Gly 385 | Val | Phe | Leu | Ile | Ala 390 | Cys | Met | Val | Val | Thr 395 | Val | Ile | Leu | Cys | Arg 400 |
| Met | Lys | Asn | Thr | Thr 405 | Lys | Lys | Pro | Asp | Phe 410 | Ser | Ser | Gln | Pro | Ala 415 | Val |
| His | Lys | Leu | Thr 420 | Lys | Arg | Ile | Pro | Leu 425 | Arg | Arg | Gln | Val | Thr 430 | Val | Ser |
| Ala | Glu | Ser 435 | Ser | Ser | Ser | Met | Asn 440 | Ser | Asn | Thr | Pro | Leu 445 | Val | Arg | Ile |
| Thr | Thr 450 | Arg | Leu | Ser | Ser | Thr 455 | Ala | Asp | Thr | Pro | Met 460 | Leu | Ala | Gly | Val |
| Ser 465 | Glu | Tyr | Glu | Leu | Pro 470 | Glu | Asp | Pro | Lys | Trp 475 | Glu | Phe | Pro | Arg | Asp 480 |
| Lys | Leu | Thr | Leu | Gly 485 | Lys | Pro | Leu | Gly | Glu 490 | Gly | Cys | Phe | Gly 495 | Gln | Val |
| Val | Met | Ala | Glu | Ala | Val | Gly | Ile | Asp | Lys | Asp | Lys | Pro | Lys | Glu | Ala |

```
                   500                      505                       510
Val  Thr  Val  Ala  Val  Lys  Met  Leu  Lys  Asp  Asp  Ala  Thr  Glu  Lys  Asp
          515                      520                      525

Leu  Ser  Asp  Leu  Val  Ser  Glu  Met  Glu  Met  Met  Lys  Met  Ile  Gly  Lys
          530                      535                      540

His  Lys  Asn  Ile  Ile  Asn  Leu  Leu  Gly  Ala  Cys  Thr  Gln  Asp  Gly  Pro
545                           550                      555                 560

Leu  Tyr  Val  Ile  Val  Glu  Tyr  Ala  Ser  Lys  Gly  Asn  Leu  Arg  Glu  Tyr
               565                      570                      575

Leu  Arg  Ala  Arg  Arg  Pro  Pro  Gly  Met  Glu  Tyr  Ser  Tyr  Asp  Ile  Asn
          580                      585                      590

Arg  Val  Pro  Glu  Glu  Gln  Met  Thr  Phe  Lys  Asp  Leu  Val  Ser  Cys  Thr
          595                      600                      605

Tyr  Gln  Leu  Ala  Arg  Gly  Met  Glu  Tyr  Leu  Ala  Ser  Gln  Lys  Cys  Ile
          610                      615                      620

His  Arg  Asp  Leu  Ala  Ala  Arg  Asn  Val  Leu  Val  Thr  Glu  Asn  Asn  Val
625                           630                      635                 640

Met  Lys  Ile
```

( 2 ) INFORMATION FOR SEQ ID NO:7:

( i ) SEQUENCE CHARACTERISTICS:
        ( A ) LENGTH: 2676 base pairs
        ( B ) TYPE: nucleic acid
        ( C ) STRANDEDNESS: double
        ( D ) TOPOLOGY: linear ( i i ) MOLECULE TYPE: cDNA ( i x ) FEATURE:
        ( A ) NAME/KEY: CDS
        ( B ) LOCATION: 25..2331

( x i ) SEQUENCE DESCRIPTION: SEQ ID NO:7:

```
GGACCGGGGA TTGGTACCGT AACC ATG GTC AGC TGG GGT CGT TTC ATC TGC          51
                           Met Val Ser Trp Gly Arg Phe Ile Cys
                            1               5

CTG GTC GTG GTC ACC ATG GCA ACC TTG TCC CTG GCC CGG CCC TCC TTC         99
Leu Val Val Val Thr Met Ala Thr Leu Ser Leu Ala Arg Pro Ser Phe
 10              15                  20                      25

AGT TTA GTT GAG GAT ACC ACA TTA GAG CCA GAA GAG CCA CCA ACC AAA        147
Ser Leu Val Glu Asp Thr Thr Leu Glu Pro Glu Glu Pro Pro Thr Lys
             30                  35                      40

TAC CAA ATC TCT CAA CCA GAA GTG TAC GTG GCT GCG CCA GGG GAG TCG        195
Tyr Gln Ile Ser Gln Pro Glu Val Tyr Val Ala Ala Pro Gly Glu Ser
                45                  50                  55

CTA GAG GTG CGC TGC CTG TTG AAA GAT GCC GCC GTG ATC AGT TGG ACT        243
Leu Glu Val Arg Cys Leu Leu Lys Asp Ala Ala Val Ile Ser Trp Thr
            60                  65                  70

AAG GAT GGG GTG CAC TTG GGG CCC AAC AAT AGG ACA GTG CTT ATT GGG        291
Lys Asp Gly Val His Leu Gly Pro Asn Asn Arg Thr Val Leu Ile Gly
     75                  80                  85

GAG TAC TTG CAG ATA AAG GGC GCC ACG CCT AGA GAC TCC GGC CTC TAT        339
Glu Tyr Leu Gln Ile Lys Gly Ala Thr Pro Arg Asp Ser Gly Leu Tyr
 90                  95                 100                 105

GCT TGT ACT GCC AGT AGG ACT GTA GAC AGT GAA ACT TGG TAC TTC ATG        387
Ala Cys Thr Ala Ser Arg Thr Val Asp Ser Glu Thr Trp Tyr Phe Met
                110                 115                 120

GTG AAT GTC ACA GAT GCC ATC TCA TCC GGA GAT GAT GAG GAT GAC ACC        435
Val Asn Val Thr Asp Ala Ile Ser Ser Gly Asp Asp Glu Asp Asp Thr
             125                 130                 135
```

| | | | | | | | | | | | | | | | | |
|---|---|---|---|---|---|---|---|---|---|---|---|---|---|---|---|---|
| GAT | GGT | GCG | GAA | GAT | TTT | GTC | AGT | GAG | AAC | AGT | AAC | AAC | AAG | AGA | GCA | 483 |
| Asp | Gly | Ala | Glu | Asp | Phe | Val | Ser | Glu | Asn | Ser | Asn | Asn | Lys | Arg | Ala | |
| | | 140 | | | | 145 | | | | | 150 | | | | | |
| CCA | TAC | TGG | ACC | AAC | ACA | GAA | AAG | ATG | GAA | AAG | CGG | CTC | CAT | GCT | GTG | 531 |
| Pro | Tyr | Trp | Thr | Asn | Thr | Glu | Lys | Met | Glu | Lys | Arg | Leu | His | Ala | Val | |
| | 155 | | | | | 160 | | | | | 165 | | | | | |
| CCT | GCG | GCC | AAC | ACT | GTC | AAG | TTT | CGC | TGC | CCA | GCC | GGG | GGG | AAC | CCA | 579 |
| Pro | Ala | Ala | Asn | Thr | Val | Lys | Phe | Arg | Cys | Pro | Ala | Gly | Gly | Asn | Pro | |
| 170 | | | | | 175 | | | | | 180 | | | | | 185 | |
| ATG | CCA | ACC | ATG | CGG | TGG | CTG | AAA | AAC | GGG | AAG | GAG | TTT | AAG | CAG | GAG | 627 |
| Met | Pro | Thr | Met | Arg | Trp | Leu | Lys | Asn | Gly | Lys | Glu | Phe | Lys | Gln | Glu | |
| | | | | 190 | | | | | 195 | | | | | 200 | | |
| CAT | CGC | ATT | GGA | GGC | TAC | AAG | GTA | CGA | AAC | CAG | CAC | TGG | AGC | CTC | ATT | 675 |
| His | Arg | Ile | Gly | Gly | Tyr | Lys | Val | Arg | Asn | Gln | His | Trp | Ser | Leu | Ile | |
| | | | 205 | | | | | 210 | | | | | 215 | | | |
| ATG | GAA | AGT | GTG | GTC | CCA | TCT | GAC | AAG | GGA | AAT | TAT | ACC | TGT | GTG | GTG | 723 |
| Met | Glu | Ser | Val | Val | Pro | Ser | Asp | Lys | Gly | Asn | Tyr | Thr | Cys | Val | Val | |
| | | | 220 | | | | 225 | | | | | 230 | | | | |
| GAG | AAT | GAA | TAC | GGG | TCC | ATC | AAT | CAC | ACG | TAC | CAC | CTG | GAT | GTT | GTG | 771 |
| Glu | Asn | Glu | Tyr | Gly | Ser | Ile | Asn | His | Thr | Tyr | His | Leu | Asp | Val | Val | |
| | 235 | | | | | 240 | | | | | 245 | | | | | |
| GAG | CGA | TCG | CCT | CAC | CGG | CCC | ATC | CTC | CAA | GCC | GGA | CTG | CCG | GCA | AAT | 819 |
| Glu | Arg | Ser | Pro | His | Arg | Pro | Ile | Leu | Gln | Ala | Gly | Leu | Pro | Ala | Asn | |
| 250 | | | | | 255 | | | | | 260 | | | | | 265 | |
| GCC | TCC | ACA | GTG | GTC | GGA | GGA | GAC | GTA | GAG | TTT | GTC | TGC | AAG | GTT | TAC | 867 |
| Ala | Ser | Thr | Val | Val | Gly | Gly | Asp | Val | Glu | Phe | Val | Cys | Lys | Val | Tyr | |
| | | | | 270 | | | | 275 | | | | | 280 | | | |
| AGT | GAT | GCC | CAG | CCC | CAC | ATC | CAG | TGG | ATC | AAG | CAC | GTG | GAA | AAG | AAC | 915 |
| Ser | Asp | Ala | Gln | Pro | His | Ile | Gln | Trp | Ile | Lys | His | Val | Glu | Lys | Asn | |
| | | | 285 | | | | | 290 | | | | | 295 | | | |
| GGC | AGT | AAA | TAC | GGG | CCC | GAC | GGG | CTG | CCC | TAC | CTC | AAG | GTT | CTC | AAG | 963 |
| Gly | Ser | Lys | Tyr | Gly | Pro | Asp | Gly | Leu | Pro | Tyr | Leu | Lys | Val | Leu | Lys | |
| | | 300 | | | | | 305 | | | | | 310 | | | | |
| CAC | TCG | GGG | ATA | AAT | AGT | TCC | AAT | GCA | GAA | GTG | CTG | GCT | CTG | TTC | AAT | 1011 |
| His | Ser | Gly | Ile | Asn | Ser | Ser | Asn | Ala | Glu | Val | Leu | Ala | Leu | Phe | Asn | |
| | 315 | | | | | 320 | | | | | 325 | | | | | |
| GTG | ACC | GAG | GCG | GAT | GCG | GGG | GAA | TAT | ATA | TGT | AAG | GTC | TCC | AAT | TAT | 1059 |
| Val | Thr | Glu | Ala | Asp | Ala | Gly | Glu | Tyr | Ile | Cys | Lys | Val | Ser | Asn | Tyr | |
| 330 | | | | | 335 | | | | | 340 | | | | | 345 | |
| ATA | GGG | CAG | GCC | AAC | CAG | TCT | GCC | TGG | CTC | ACT | GTC | CTG | CCA | AAA | CAG | 1107 |
| Ile | Gly | Gln | Ala | Asn | Gln | Ser | Ala | Trp | Leu | Thr | Val | Leu | Pro | Lys | Gln | |
| | | | | 350 | | | | | 355 | | | | | 360 | | |
| CAA | GCG | CCT | GGA | AGA | GAA | AAG | GAG | ATT | ACA | GCT | TCC | CCA | GAC | TAC | CTG | 1155 |
| Gln | Ala | Pro | Gly | Arg | Glu | Lys | Glu | Ile | Thr | Ala | Ser | Pro | Asp | Tyr | Leu | |
| | | | 365 | | | | | 370 | | | | | 375 | | | |
| GAG | ATA | GCC | ATT | TAC | TGC | ATA | GGG | GTC | TTC | TTA | ATC | GCC | TGT | ATG | GTG | 1203 |
| Glu | Ile | Ala | Ile | Tyr | Cys | Ile | Gly | Val | Phe | Leu | Ile | Ala | Cys | Met | Val | |
| | | 380 | | | | | 385 | | | | | 390 | | | | |
| GTA | ACA | GTC | ATC | CTG | TGC | CGA | ATG | AAG | AAC | ACG | ACC | AAG | AAG | CCA | GAC | 1251 |
| Val | Thr | Val | Ile | Leu | Cys | Arg | Met | Lys | Asn | Thr | Thr | Lys | Lys | Pro | Asp | |
| | 395 | | | | | 400 | | | | | 405 | | | | | |
| TTC | AGC | AGC | CAG | CCG | GCT | GTG | CAC | AAG | CTG | ACC | AAA | CGT | ATC | CCC | CTG | 1299 |
| Phe | Ser | Ser | Gln | Pro | Ala | Val | His | Lys | Leu | Thr | Lys | Arg | Ile | Pro | Leu | |
| 410 | | | | | 415 | | | | | 420 | | | | | 425 | |
| CGG | AGA | CAG | GTA | ACA | GTT | TCG | GCT | GAG | TCC | AGC | TCC | TCC | ATG | AAC | TCC | 1347 |
| Arg | Arg | Gln | Val | Thr | Val | Ser | Ala | Glu | Ser | Ser | Ser | Ser | Met | Asn | Ser | |
| | | | | 430 | | | | | 435 | | | | | 440 | | |
| AAC | ACC | CCG | CTG | GTG | AGG | ATA | ACA | ACA | CGC | CTC | TCT | TCA | ACG | GCA | GAC | 1395 |
| Asn | Thr | Pro | Leu | Val | Arg | Ile | Thr | Thr | Arg | Leu | Ser | Ser | Thr | Ala | Asp | |
| | | | 445 | | | | | 450 | | | | | 455 | | | |

| | | | | | | | | | | | | | | | | |
|---|---|---|---|---|---|---|---|---|---|---|---|---|---|---|---|---|
| ACC | CCC | ATG | CTG | GCA | GGG | GTC | TCC | GAG | TAT | GAA | CTT | CCA | GAG | GAC | CCA | 1443 |
| Thr | Pro | Met | Leu | Ala | Gly | Val | Ser | Glu | Tyr | Glu | Leu | Pro | Glu | Asp | Pro | |
| | | 460 | | | | | 465 | | | | | 470 | | | | |
| AAA | TGG | GAG | TTT | CCA | AGA | GAT | AAG | CTG | ACA | CTG | GGC | AAG | CCC | CTG | GGA | 1491 |
| Lys | Trp | Glu | Phe | Pro | Arg | Asp | Lys | Leu | Thr | Leu | Gly | Lys | Pro | Leu | Gly | |
| | 475 | | | | | 480 | | | | | 485 | | | | | |
| GAA | GGT | TGC | TTT | GGG | CAA | GTG | GTC | ATG | GCG | GAA | GCA | GTG | GGA | ATT | GAC | 1539 |
| Glu | Gly | Cys | Phe | Gly | Gln | Val | Val | Met | Ala | Glu | Ala | Val | Gly | Ile | Asp | |
| 490 | | | | | 495 | | | | | 500 | | | | | 505 | |
| AAA | GAC | AAG | CCC | AAG | GAG | GCG | GTC | ACC | GTG | GCC | GTG | AAG | ATG | TTG | AAA | 1587 |
| Lys | Asp | Lys | Pro | Lys | Glu | Ala | Val | Thr | Val | Ala | Val | Lys | Met | Leu | Lys | |
| | | | | 510 | | | | | 515 | | | | | 520 | | |
| GAT | GAT | GCC | ACA | GAG | AAA | GAC | CTT | TCT | GAT | CTG | GTG | TCA | GAG | ATG | GAG | 1635 |
| Asp | Asp | Ala | Thr | Glu | Lys | Asp | Leu | Ser | Asp | Leu | Val | Ser | Glu | Met | Glu | |
| | | | 525 | | | | | 530 | | | | | 535 | | | |
| ATG | ATG | AAG | ATG | ATT | GGG | AAA | CAC | AAG | AAT | ATC | ATA | AAT | CTT | CTT | GGA | 1683 |
| Met | Met | Lys | Met | Ile | Gly | Lys | His | Lys | Asn | Ile | Ile | Asn | Leu | Leu | Gly | |
| | | 540 | | | | | 545 | | | | | 550 | | | | |
| GCC | TGC | ACA | CAG | GAT | GGG | CCT | CTC | TAT | GTC | ATA | GTT | GAG | TAT | GCC | TCT | 1731 |
| Ala | Cys | Thr | Gln | Asp | Gly | Pro | Leu | Tyr | Val | Ile | Val | Glu | Tyr | Ala | Ser | |
| 555 | | | | | 560 | | | | | 565 | | | | | | |
| AAA | GGC | AAC | CTC | CGA | GAA | TAC | CTC | CGA | GCC | CGG | AGG | CCA | CCC | GGG | ATG | 1779 |
| Lys | Gly | Asn | Leu | Arg | Glu | Tyr | Leu | Arg | Ala | Arg | Arg | Pro | Pro | Gly | Met | |
| 570 | | | | | 575 | | | | | 580 | | | | | 585 | |
| GAG | TAC | TCC | TAT | GAC | ATT | AAC | CGT | GTT | CCT | GAG | GAG | CAG | ATG | ACC | TTC | 1827 |
| Glu | Tyr | Ser | Tyr | Asp | Ile | Asn | Arg | Val | Pro | Glu | Glu | Gln | Met | Thr | Phe | |
| | | | | 590 | | | | | 595 | | | | | 600 | | |
| AAG | GAC | TTG | GTG | TCA | TGC | ACC | TAC | CAG | CTG | GCC | AGA | GGC | ATG | GAG | TAC | 1875 |
| Lys | Asp | Leu | Val | Ser | Cys | Thr | Tyr | Gln | Leu | Ala | Arg | Gly | Met | Glu | Tyr | |
| | | | 605 | | | | | 610 | | | | | 615 | | | |
| TTG | GCT | TCC | CAA | AAA | TGT | ATT | CAT | CGA | GAT | TTA | GCA | GCC | AGA | AAT | GTT | 1923 |
| Leu | Ala | Ser | Gln | Lys | Cys | Ile | His | Arg | Asp | Leu | Ala | Ala | Arg | Asn | Val | |
| | | 620 | | | | | 625 | | | | | 630 | | | | |
| TTG | GTA | ACA | GAA | AAC | AAT | GTG | ATG | AAA | ATA | GCA | GAC | TTT | GGA | CTC | GCC | 1971 |
| Leu | Val | Thr | Glu | Asn | Asn | Val | Met | Lys | Ile | Ala | Asp | Phe | Gly | Leu | Ala | |
| | 635 | | | | | 640 | | | | | 645 | | | | | |
| AGA | GAT | ATC | AAC | AAT | ATA | GAC | TAT | TAC | AAA | AAG | ACC | ACC | AAT | GGG | CGG | 2019 |
| Arg | Asp | Ile | Asn | Asn | Ile | Asp | Tyr | Tyr | Lys | Lys | Thr | Thr | Asn | Gly | Arg | |
| 650 | | | | | 655 | | | | | 660 | | | | | 665 | |
| CTT | CCA | GTC | AAG | TGG | ATG | GCT | CCA | GAA | GCC | CTG | TTT | GAT | AGA | GTA | TAC | 2067 |
| Leu | Pro | Val | Lys | Trp | Met | Ala | Pro | Glu | Ala | Leu | Phe | Asp | Arg | Val | Tyr | |
| | | | | 670 | | | | | 675 | | | | | 680 | | |
| ACT | CAT | CAG | AGT | GAT | GTC | TGG | TCC | TTC | GGG | GTG | TTA | ATG | TGG | GAG | ATC | 2115 |
| Thr | His | Gln | Ser | Asp | Val | Trp | Ser | Phe | Gly | Val | Leu | Met | Trp | Glu | Ile | |
| | | | 685 | | | | | 690 | | | | | 695 | | | |
| TTC | ACT | TTA | GGG | GGC | TCG | CCC | TAC | CCA | GGG | ATT | CCC | GTG | GAG | GAA | CTT | 2163 |
| Phe | Thr | Leu | Gly | Gly | Ser | Pro | Tyr | Pro | Gly | Ile | Pro | Val | Glu | Glu | Leu | |
| | | 700 | | | | | 705 | | | | | 710 | | | | |
| TTT | AAG | CTG | CTG | AAG | GAA | GGA | CAC | AGA | ATG | GAT | AAG | CCA | GCC | AAC | TGC | 2211 |
| Phe | Lys | Leu | Leu | Lys | Glu | Gly | His | Arg | Met | Asp | Lys | Pro | Ala | Asn | Cys | |
| 715 | | | | | 720 | | | | | 725 | | | | | | |
| ACC | AAC | GAA | CTG | TAC | ATG | ATG | ATG | AGG | GAC | TGT | TGG | CAT | GCA | GTG | CCC | 2259 |
| Thr | Asn | Glu | Leu | Tyr | Met | Met | Met | Arg | Asp | Cys | Trp | His | Ala | Val | Pro | |
| 730 | | | | | 735 | | | | | 740 | | | | | 745 | |
| TCC | CAG | AGA | CCA | ACG | TTC | AAG | CAG | TTG | GTA | GAA | GAC | TTG | GAT | CGA | ATT | 2307 |
| Ser | Gln | Arg | Pro | Thr | Phe | Lys | Gln | Leu | Val | Glu | Asp | Leu | Asp | Arg | Ile | |
| | | | | 750 | | | | | 755 | | | | | 760 | | |
| CTC | ACT | CTC | ACA | ACC | AAT | GAG | ATC | TGAAAGTTTA | TGGCTTCATT | GAGAAACTGG | | | | | | 2361 |
| Leu | Thr | Leu | Thr | Thr | Asn | Glu | Ile | | | | | | | | | |
| | | | 765 | | | | | | | | | | | | | |

```
GAAAAGTTGG TCAGGCGCAG TGGCTCATGC CTGTAATCCC AGCACTTTGG GAGGCCGAGG    2421

CAGGCGGATC ATGAGGTCAG GAGTTCCAGA CCAGCCTGGC CAACATGGTG AAACCCTGTC    2481

TCTACTAAAG ATACAAAAAA TTAGCCGGGC GTGTTGGTGT GCGCCTGTAA TCCCAGCTAC    2541

TCCGGGAGGC TGAGGCAGGA GAGTCACTTG AACCGGGGAG GCGGAGGTTA CAGTGAGCCG    2601

AGATCATGCC ATTGCATTCC AGCCTTGGCG ACAGAGCGAG ACTCCATCTA AAAAAAAAA    2661

AAAAAAAAA AAAAA                                                      2676
```

(2) INFORMATION FOR SEQ ID NO:8:

(i) SEQUENCE CHARACTERISTICS:
        (A) LENGTH: 769 amino acids
        (B) TYPE: amino acid
        (D) TOPOLOGY: linear (ii) MOLECULE TYPE: protein (xi) SEQUENCE DESCRIPTION: SEQ ID NO:8:

```
Met Val Ser Trp Gly Arg Phe Ile Cys Leu Val Val Thr Met Ala
 1               5                  10                  15

Thr Leu Ser Leu Ala Arg Pro Ser Phe Ser Leu Val Glu Asp Thr Thr
                20                  25                  30

Leu Glu Pro Glu Glu Pro Pro Thr Lys Tyr Gln Ile Ser Gln Pro Glu
                35                  40                  45

Val Tyr Val Ala Ala Pro Gly Glu Ser Leu Glu Val Arg Cys Leu Leu
    50                  55                  60

Lys Asp Ala Ala Val Ile Ser Trp Thr Lys Asp Gly Val His Leu Gly
 65                  70                  75                  80

Pro Asn Asn Arg Thr Val Leu Ile Gly Glu Tyr Leu Gln Ile Lys Gly
                85                  90                  95

Ala Thr Pro Arg Asp Ser Gly Leu Tyr Ala Cys Thr Ala Ser Arg Thr
                100                 105                 110

Val Asp Ser Glu Thr Trp Tyr Phe Met Val Asn Val Thr Asp Ala Ile
            115                 120                 125

Ser Ser Gly Asp Asp Glu Asp Asp Thr Asp Gly Ala Glu Asp Phe Val
    130                 135                 140

Ser Glu Asn Ser Asn Asn Lys Arg Ala Pro Tyr Trp Thr Asn Thr Glu
145                 150                 155                 160

Lys Met Glu Lys Arg Leu His Ala Val Pro Ala Ala Asn Thr Val Lys
                165                 170                 175

Phe Arg Cys Pro Ala Gly Gly Asn Pro Met Pro Thr Met Arg Trp Leu
            180                 185                 190

Lys Asn Gly Lys Glu Phe Lys Gln Glu His Arg Ile Gly Gly Tyr Lys
        195                 200                 205

Val Arg Asn Gln His Trp Ser Leu Ile Met Glu Ser Val Val Pro Ser
    210                 215                 220

Asp Lys Gly Asn Tyr Thr Cys Val Val Glu Asn Glu Tyr Gly Ser Ile
225                 230                 235                 240

Asn His Thr Tyr His Leu Asp Val Val Glu Arg Ser Pro His Arg Pro
                245                 250                 255

Ile Leu Gln Ala Gly Leu Pro Ala Asn Ala Ser Thr Val Val Gly Gly
            260                 265                 270

Asp Val Glu Phe Val Cys Lys Val Tyr Ser Asp Ala Gln Pro His Ile
            275                 280                 285

Gln Trp Ile Lys His Val Glu Lys Asn Gly Ser Lys Tyr Gly Pro Asp
```

-continued

|  | 290 |  |  |  | 295 |  |  |  | 300 |  |  |  |  |
|---|---|---|---|---|---|---|---|---|---|---|---|---|---|
| Gly 305 | Leu | Pro | Tyr | Leu 310 | Lys | Val | Leu | His 315 | Gly | Ile | Asn | Ser | Ser 320 |
| Asn | Ala | Glu | Val | Leu 325 | Ala | Leu | Phe | Asn | Val 330 | Thr | Glu | Ala | Asp | Ala | Gly 335 |
| Glu | Tyr | Ile | Cys 340 | Lys | Val | Ser | Asn | Tyr 345 | Ile | Gly | Gln | Ala | Asn | Gln 350 | Ser |
| Ala | Trp | Leu 355 | Thr | Val | Leu | Pro | Lys 360 | Gln | Gln | Ala | Pro | Gly 365 | Arg | Glu | Lys |
| Glu | Ile | Thr 370 | Ala | Ser | Pro | Asp 375 | Tyr | Leu | Glu | Ile | Ala 380 | Ile | Tyr | Cys | Ile |
| Gly 385 | Val | Phe | Leu | Ile | Ala 390 | Cys | Met | Val | Val | Thr 395 | Val | Ile | Leu | Cys | Arg 400 |
| Met | Lys | Asn | Thr | Thr 405 | Lys | Lys | Pro | Asp | Phe 410 | Ser | Ser | Gln | Pro | Ala 415 | Val |
| His | Lys | Leu | Thr 420 | Lys | Arg | Ile | Pro | Leu 425 | Arg | Arg | Gln | Val | Thr 430 | Val | Ser |
| Ala | Glu | Ser 435 | Ser | Ser | Ser | Met | Asn 440 | Ser | Asn | Thr | Pro | Leu 445 | Val | Arg | Ile |
| Thr | Thr 450 | Arg | Leu | Ser | Ser | Thr 455 | Ala | Asp | Thr | Pro | Met 460 | Leu | Ala | Gly | Val |
| Ser 465 | Glu | Tyr | Glu | Leu | Pro 470 | Glu | Asp | Pro | Lys | Trp 475 | Glu | Phe | Pro | Arg | Asp 480 |
| Lys | Leu | Thr | Leu | Gly 485 | Lys | Pro | Leu | Gly | Glu 490 | Gly | Cys | Phe | Gly | Gln 495 | Val |
| Val | Met | Ala | Glu 500 | Ala | Val | Gly | Ile | Asp 505 | Lys | Asp | Lys | Pro | Lys 510 | Glu | Ala |
| Val | Thr | Val 515 | Ala | Val | Lys | Met | Leu 520 | Lys | Asp | Asp | Ala | Thr 525 | Glu | Lys | Asp |
| Leu | Ser 530 | Asp | Leu | Val | Ser | Glu 535 | Met | Glu | Met | Met | Lys 540 | Met | Ile | Gly | Lys |
| His 545 | Lys | Asn | Ile | Ile | Asn 550 | Leu | Leu | Gly | Ala | Cys 555 | Thr | Gln | Asp | Gly | Pro 560 |
| Leu | Tyr | Val | Ile | Val 565 | Glu | Tyr | Ala | Ser | Lys 570 | Gly | Asn | Leu | Arg | Glu 575 | Tyr |
| Leu | Arg | Ala | Arg 580 | Arg | Pro | Pro | Gly | Met 585 | Glu | Tyr | Ser | Tyr | Asp 590 | Ile | Asn |
| Arg | Val | Pro 595 | Glu | Glu | Gln | Met | Thr 600 | Phe | Lys | Asp | Leu | Val 605 | Ser | Cys | Thr |
| Tyr | Gln 610 | Leu | Ala | Arg | Gly | Met 615 | Glu | Tyr | Leu | Ala | Ser 620 | Gln | Lys | Cys | Ile |
| His 625 | Arg | Asp | Leu | Ala | Ala 630 | Arg | Asn | Val | Leu | Val 635 | Thr | Glu | Asn | Asn | Val 640 |
| Met | Lys | Ile | Ala | Asp 645 | Phe | Gly | Leu | Ala | Arg 650 | Asp | Ile | Asn | Asn | Ile 655 | Asp |
| Tyr | Tyr | Lys | Lys 660 | Thr | Thr | Asn | Gly | Arg 665 | Leu | Pro | Val | Lys | Trp 670 | Met | Ala |
| Pro | Glu | Ala 675 | Leu | Phe | Asp | Arg | Val 680 | Tyr | Thr | His | Gln | Ser 685 | Asp | Val | Trp |
| Ser | Phe 690 | Gly | Val | Leu | Met | Trp 695 | Glu | Ile | Phe | Thr | Leu 700 | Gly | Gly | Ser | Pro |
| Tyr 705 | Pro | Gly | Ile | Pro | Val 710 | Glu | Glu | Leu | Phe | Lys 715 | Leu | Leu | Lys | Glu | Gly 720 |

5,750,371

-continued

| | | | | | | | | | | | | | | |
|---|---|---|---|---|---|---|---|---|---|---|---|---|---|---|
| His | Arg | Met | Asp | Lys | Pro | Ala | Asn | Cys | Thr | Asn | Glu | Leu | Tyr | Met | Met |
| | | | | 725 | | | | 730 | | | | | 735 | | |
| Met | Arg | Asp | Cys | Trp | His | Ala | Val | Pro | Ser | Gln | Arg | Pro | Thr | Phe | Lys |
| | | | 740 | | | | | 745 | | | | | 750 | | |
| Gln | Leu | Val | Glu | Asp | Leu | Asp | Arg | Ile | Leu | Thr | Leu | Thr | Thr | Asn | Glu |
| | | 755 | | | | | 760 | | | | | 765 | | | |
| Ile | | | | | | | | | | | | | | | |

( 2 ) INFORMATION FOR SEQ ID NO:9:

( i ) SEQUENCE CHARACTERISTICS:
        ( A ) LENGTH: 2310 base pairs
        ( B ) TYPE: nucleic acid
        ( C ) STRANDEDNESS: double
        ( D ) TOPOLOGY: linear ( i i ) MOLECULE TYPE: cDNA ( i x ) FEATURE:
        ( A ) NAME/KEY: CDS
        ( B ) LOCATION: 25..1980

( x i ) SEQUENCE DESCRIPTION: SEQ ID NO:9:

| | | | | | | | | | | | | | | | | |
|---|---|---|---|---|---|---|---|---|---|---|---|---|---|---|---|---|
| GGACCGGGGA | TTGGTACCGT | AACC | ATG | GTC | AGC | TGG | GGT | CGT | TTC | ATC | TGC | | | | | 51 |
| | | | Met | Val | Ser | Trp | Gly | Arg | Phe | Ile | Cys | | | | | |
| | | | 1 | | | | 5 | | | | | | | | | |
| CTG | GTC | GTG | GTC | ACC | ATG | GCA | ACC | TTG | TCC | CTG | GCC | CGG | CCC | TCC | TTC | 99 |
| Leu | Val | Val | Val | Thr | Met | Ala | Thr | Leu | Ser | Leu | Ala | Arg | Pro | Ser | Phe | |
| 10 | | | | 15 | | | | 20 | | | | | 25 | | | |
| AGT | TTA | GTT | GAG | GAT | ACC | ACA | TTA | GAG | CCA | GAA | GGA | GCA | CCA | TAC | TGG | 147 |
| Ser | Leu | Val | Glu | Asp | Thr | Thr | Leu | Glu | Pro | Glu | Gly | Ala | Pro | Tyr | Trp | |
| | | | 30 | | | | | 35 | | | | | 40 | | | |
| ACC | AAC | ACA | GAA | AAG | ATG | GAA | AAG | CGG | CTC | CAT | GCT | GTG | CCT | GCG | GCC | 195 |
| Thr | Asn | Thr | Glu | Lys | Met | Glu | Lys | Arg | Leu | His | Ala | Val | Pro | Ala | Ala | |
| | | | 45 | | | | 50 | | | | | 55 | | | | |
| AAC | ACT | GTC | AAG | TTT | CGC | TGC | CCA | GCC | GGG | GGG | AAC | CCA | ATG | CCA | ACC | 243 |
| Asn | Thr | Val | Lys | Phe | Arg | Cys | Pro | Ala | Gly | Gly | Asn | Pro | Met | Pro | Thr | |
| | | 60 | | | | 65 | | | | | 70 | | | | | |
| ATG | CGG | TGG | CTG | AAA | AAC | GGG | AAG | GAG | TTT | AAG | CAG | GAG | CAT | CGC | ATT | 291 |
| Met | Arg | Trp | Leu | Lys | Asn | Gly | Lys | Glu | Phe | Lys | Gln | Glu | His | Arg | Ile | |
| 75 | | | | | 80 | | | | | 85 | | | | | | |
| GGA | GGC | TAC | AAG | GTA | CGA | AAC | CAG | CAC | TGG | AGC | CTC | ATT | ATG | GAA | AGT | 339 |
| Gly | Gly | Tyr | Lys | Val | Arg | Asn | Gln | His | Trp | Ser | Leu | Ile | Met | Glu | Ser | |
| 90 | | | | 95 | | | | | 100 | | | | | 105 | | |
| GTG | GTC | CCA | TCT | GAC | AAG | GGA | AAT | TAT | ACC | TGT | GTG | GTG | GAG | AAT | GAA | 387 |
| Val | Val | Pro | Ser | Asp | Lys | Gly | Asn | Tyr | Thr | Cys | Val | Val | Glu | Asn | Glu | |
| | | | | 110 | | | | | 115 | | | | | 120 | | |
| TAC | GGG | TCC | ATC | AAT | CAC | ACG | TAC | CAC | CTG | GAT | GTT | GTG | GAG | CGA | TCG | 435 |
| Tyr | Gly | Ser | Ile | Asn | His | Thr | Tyr | His | Leu | Asp | Val | Val | Glu | Arg | Ser | |
| | | | 125 | | | | | 130 | | | | | 135 | | | |
| CCT | CAC | CGG | CCC | ATC | CTC | CAA | GCC | GGA | CTG | CCG | GCA | AAT | GCC | TCC | ACA | 483 |
| Pro | His | Arg | Pro | Ile | Leu | Gln | Ala | Gly | Leu | Pro | Ala | Asn | Ala | Ser | Thr | |
| | | 140 | | | | | 145 | | | | | 150 | | | | |
| GTG | GTC | GGA | GGA | GAC | GTA | GAG | TTT | GTC | TGC | AAG | GTT | TAC | AGT | GAT | GCC | 531 |
| Val | Val | Gly | Gly | Asp | Val | Glu | Phe | Val | Cys | Lys | Val | Tyr | Ser | Asp | Ala | |
| | | | 155 | | | | | 160 | | | | | 165 | | | |
| CAG | CCC | CAC | ATC | CAG | TGG | ATC | AAG | CAC | GTG | GAA | AAG | AAC | GGC | AGT | AAA | 579 |
| Gln | Pro | His | Ile | Gln | Trp | Ile | Lys | His | Val | Glu | Lys | Asn | Gly | Ser | Lys | |
| 170 | | | | | 175 | | | | | 180 | | | | | 185 | |
| TAC | GGG | CCC | GAC | GGG | CTG | CCC | TAC | CTC | AAG | GTT | CTC | AAG | CAC | TCG | GGG | 627 |
| Tyr | Gly | Pro | Asp | Gly | Leu | Pro | Tyr | Leu | Lys | Val | Leu | Lys | His | Ser | Gly | |
| | | | | 190 | | | | | 195 | | | | | 200 | | |

| | | | | | | | | | | | | | | | | |
|---|---|---|---|---|---|---|---|---|---|---|---|---|---|---|---|---|
| ATA | AAT | AGT | TCC | AAT | GCA | GAA | GTG | CTG | GCT | CTG | TTC | AAT | GTG | ACC | GAG | 675 |
| Ile | Asn | Ser | Ser | Asn | Ala | Glu | Val | Leu | Ala | Leu | Phe | Asn | Val | Thr | Glu | |
| | | | 205 | | | | 210 | | | | | 215 | | | | |
| GCG | GAT | GCT | GGG | GAA | TAT | ATA | TGT | AAG | GTC | TCC | AAT | TAT | ATA | GGG | CAG | 723 |
| Ala | Asp | Ala | Gly | Glu | Tyr | Ile | Cys | Lys | Val | Ser | Asn | Tyr | Ile | Gly | Gln | |
| | | 220 | | | | | 225 | | | | | 230 | | | | |
| GCC | AAC | CAG | TCT | GCC | TGG | CTC | ACT | GTC | CTG | CCA | AAA | CAG | CAA | GCG | CCT | 771 |
| Ala | Asn | Gln | Ser | Ala | Trp | Leu | Thr | Val | Leu | Pro | Lys | Gln | Gln | Ala | Pro | |
| | | 235 | | | | | 240 | | | | | 245 | | | | |
| GGA | AGA | GAA | AAG | GAG | ATT | ACA | GCT | TCC | CCA | GAC | TAC | CTG | GAG | ATA | GCC | 819 |
| Gly | Arg | Glu | Lys | Glu | Ile | Thr | Ala | Ser | Pro | Asp | Tyr | Leu | Glu | Ile | Ala | |
| 250 | | | | | 255 | | | | | 260 | | | | | 265 | |
| ATT | TAC | TGC | ATA | GGG | GTC | TTC | TTA | ATC | GCC | TGT | ATG | GTG | GTA | ACA | GTC | 867 |
| Ile | Tyr | Cys | Ile | Gly | Val | Phe | Leu | Ile | Ala | Cys | Met | Val | Val | Thr | Val | |
| | | | | 270 | | | | | 275 | | | | | 280 | | |
| ATC | CTG | TGC | CGA | ATG | AAG | AAC | ACG | ACC | AAG | AAG | CCA | GAC | TTC | AGC | AGC | 915 |
| Ile | Leu | Cys | Arg | Met | Lys | Asn | Thr | Thr | Lys | Lys | Pro | Asp | Phe | Ser | Ser | |
| | | | 285 | | | | | 290 | | | | | 295 | | | |
| CAG | CCG | GCT | GTG | CAC | AAG | CTG | ACC | AAA | CGT | ATC | CCC | CTG | CGG | AGA | CAG | 963 |
| Gln | Pro | Ala | Val | His | Lys | Leu | Thr | Lys | Arg | Ile | Pro | Leu | Arg | Arg | Gln | |
| | | 300 | | | | | 305 | | | | | 310 | | | | |
| GTT | TCG | GCT | GAG | TCC | AGC | TCC | TCC | ATG | AAC | TCC | AAC | ACC | CCG | CTG | GTG | 1011 |
| Val | Ser | Ala | Glu | Ser | Ser | Ser | Ser | Met | Asn | Ser | Asn | Thr | Pro | Leu | Val | |
| | | 315 | | | | | 320 | | | | | 325 | | | | |
| AGG | ATA | ACA | ACA | CGC | CTC | TCT | TCA | ACG | GCA | GAC | ACC | CCC | ATG | CTG | GCA | 1059 |
| Arg | Ile | Thr | Thr | Arg | Leu | Ser | Ser | Thr | Ala | Asp | Thr | Pro | Met | Leu | Ala | |
| 330 | | | | | 335 | | | | | 340 | | | | | 345 | |
| GGG | GTC | TCC | GAG | TAT | GAA | CTT | CCA | GAG | GAC | CCA | AAA | TGG | GAG | TTT | CCA | 1107 |
| Gly | Val | Ser | Glu | Tyr | Glu | Leu | Pro | Glu | Asp | Pro | Lys | Trp | Glu | Phe | Pro | |
| | | | | 350 | | | | | 355 | | | | | 360 | | |
| AGA | GAT | AAG | CTG | ACA | CTG | GGC | AAG | CCC | CTG | GGA | GAA | GGT | TGC | TTT | GGG | 1155 |
| Arg | Asp | Lys | Leu | Thr | Leu | Gly | Lys | Pro | Leu | Gly | Glu | Gly | Cys | Phe | Gly | |
| | | | 365 | | | | | 370 | | | | | 375 | | | |
| CAA | GTG | GTC | ATG | GCG | GAA | GCA | GTG | GGA | ATT | GAC | AAA | GAC | AAG | CCC | AAG | 1203 |
| Gln | Val | Val | Met | Ala | Glu | Ala | Val | Gly | Ile | Asp | Lys | Asp | Lys | Pro | Lys | |
| | | | 380 | | | | 385 | | | | | 390 | | | | |
| GAG | GCG | GTC | ACC | GTG | GCC | GTG | AAG | ATG | TTG | AAA | GAT | GAT | GCC | ACA | GAG | 1251 |
| Glu | Ala | Val | Thr | Val | Ala | Val | Lys | Met | Leu | Lys | Asp | Asp | Ala | Thr | Glu | |
| | | 395 | | | | | 400 | | | | | 405 | | | | |
| AAA | GAC | CTT | TCT | GAT | CTG | GTG | TCA | GAG | ATG | GAG | ATG | ATG | AAG | ATG | ATT | 1299 |
| Lys | Asp | Leu | Ser | Asp | Leu | Val | Ser | Glu | Met | Glu | Met | Met | Lys | Met | Ile | |
| 410 | | | | | 415 | | | | | 420 | | | | | 425 | |
| GGG | AAA | CAC | AAG | AAT | ATC | ATA | AAT | CTT | CTT | GGA | GCC | TGC | ACA | CAG | GAT | 1347 |
| Gly | Lys | His | Lys | Asn | Ile | Ile | Asn | Leu | Leu | Gly | Ala | Cys | Thr | Gln | Asp | |
| | | | | 430 | | | | | 435 | | | | | 440 | | |
| GGG | CCT | CTC | TAT | GTC | ATA | GTT | GAG | TAT | GCC | TCT | AAA | GGC | AAC | CTC | CGA | 1395 |
| Gly | Pro | Leu | Tyr | Val | Ile | Val | Glu | Tyr | Ala | Ser | Lys | Gly | Asn | Leu | Arg | |
| | | | | 445 | | | | | 450 | | | | | 455 | | |
| GAA | TAC | CTC | CGA | GCC | CGG | AGG | CCA | CCC | GGG | ATG | GAG | TAC | TCC | TAT | GAC | 1443 |
| Glu | Tyr | Leu | Arg | Ala | Arg | Arg | Pro | Pro | Gly | Met | Glu | Tyr | Ser | Tyr | Asp | |
| | | 460 | | | | | 465 | | | | | 470 | | | | |
| ATT | AAC | CGT | GTT | CCT | GAG | GAG | CAG | ATG | ACC | TTC | AAG | GAC | TTG | GTG | TCA | 1491 |
| Ile | Asn | Arg | Val | Pro | Glu | Glu | Gln | Met | Thr | Phe | Lys | Asp | Leu | Val | Ser | |
| | | 475 | | | | | 480 | | | | | 485 | | | | |
| TGC | ACC | TAC | CAG | CTG | GCC | AGA | GGC | ATG | GAG | TAC | TTG | GCT | TCC | CAA | AAA | 1539 |
| Cys | Thr | Tyr | Gln | Leu | Ala | Arg | Gly | Met | Glu | Tyr | Leu | Ala | Ser | Gln | Lys | |
| 490 | | | | | 495 | | | | | 500 | | | | | 505 | |
| TGT | ATT | CAT | CGA | GAT | TTA | GCA | GCC | AGA | AAT | GTT | TTG | GTA | ACA | GAA | AAC | 1587 |
| Cys | Ile | His | Arg | Asp | Leu | Ala | Ala | Arg | Asn | Val | Leu | Val | Thr | Glu | Asn | |
| | | | 510 | | | | | 515 | | | | | 520 | | | |

| | | | | | | | | | | | | | | | | |
|---|---|---|---|---|---|---|---|---|---|---|---|---|---|---|---|---|
| AAT | GTG | ATG | AAA | ATA | GCA | GAC | TTT | GGA | CTC | GCC | AGA | GAT | ATC | AAC | AAT | 1635 |
| Asn | Val | Met | Lys | Ile | Ala | Asp | Phe | Gly | Leu | Ala | Arg | Asp | Ile | Asn | Asn | |
| | | 525 | | | | | | 530 | | | | | 535 | | | |
| ATA | GAC | TAT | TAC | AAA | AAG | ACC | ACC | AAT | GGG | CGG | CTT | CCA | GTC | AAG | TGG | 1683 |
| Ile | Asp | Tyr | Tyr | Lys | Lys | Thr | Thr | Asn | Gly | Arg | Leu | Pro | Val | Lys | Trp | |
| | | | 540 | | | | | 545 | | | | 550 | | | | |
| ATG | GCT | CCA | GAA | GCC | CTG | TTT | GAT | AGA | GTA | TAC | ACT | CAT | CAG | AGT | GAT | 1731 |
| Met | Ala | Pro | Glu | Ala | Leu | Phe | Asp | Arg | Val | Tyr | Thr | His | Gln | Ser | Asp | |
| | 555 | | | | | 560 | | | | | 565 | | | | | |
| GTC | TGG | TCC | TTC | GGG | GTG | TTA | ATG | TGG | GAG | ATC | TTC | ACT | TTA | GGG | GGC | 1779 |
| Val | Trp | Ser | Phe | Gly | Val | Leu | Met | Trp | Glu | Ile | Phe | Thr | Leu | Gly | Gly | |
| 570 | | | | | 575 | | | | 580 | | | | | | 585 | |
| TCG | CCC | TAC | CCA | GGG | ATT | CCC | GTG | GAG | GAA | CTT | TTT | AAG | CTG | CTG | AAG | 1827 |
| Ser | Pro | Tyr | Pro | Gly | Ile | Pro | Val | Glu | Glu | Leu | Phe | Lys | Leu | Leu | Lys | |
| | | | | 590 | | | | | 595 | | | | | 600 | | |
| GAA | GGA | CAC | AGA | ATG | GAT | AAG | CCA | GCC | AAC | TGC | ACC | AAC | GAA | CTG | TAC | 1875 |
| Glu | Gly | His | Arg | Met | Asp | Lys | Pro | Ala | Asn | Cys | Thr | Asn | Glu | Leu | Tyr | |
| | | | 605 | | | | | 610 | | | | | 615 | | | |
| ATG | ATG | ATG | AGG | GAC | TGT | TGG | CAT | GCA | GTG | CCC | TCC | CAG | AGA | CCA | ACG | 1923 |
| Met | Met | Met | Arg | Asp | Cys | Trp | His | Ala | Val | Pro | Ser | Gln | Arg | Pro | Thr | |
| | | 620 | | | | | 625 | | | | | 630 | | | | |
| TTC | AAG | CAG | TTG | GTA | GAA | GAC | TTG | GAT | CGA | ATT | CTC | ACT | CTC | ACA | ACC | 1971 |
| Phe | Lys | Gln | Leu | Val | Glu | Asp | Leu | Asp | Arg | Ile | Leu | Thr | Leu | Thr | Thr | |
| | 635 | | | | | 640 | | | | | 645 | | | | | |
| AAT | GAG | ATC | TGAAAGTTTA | TGGCTTCATT | GAGAAACTGG | GAAAAGTTGG | | | | | | | | | | 2020 |
| Asn | Glu | Ile | | | | | | | | | | | | | | |
| 650 | | | | | | | | | | | | | | | | |

| | | | | | |
|---|---|---|---|---|---|
| TCAGGCGCAG | TGGCTCATGC | CTGTAATCCC | AGCACTTTGG | GAGGCCGAGG | CAGGCGGATC | 2080 |
| ATGAGGTCAG | GAGTTCCAGA | CCAGCCTGGC | CAACATGGTG | AAACCCTGTC | TCTACTAAAG | 2140 |
| ATACAAAAAA | TTAGCCGGGC | GTGTTGGTGT | GCGCCTGTAA | TCCCAGCTAC | TCCGGGAGGC | 2200 |
| TGAGGCAGGA | GAGTCACTTG | AACCGGGGAG | GCGGAGGTTA | CAGTGAGCCG | AGATCATGCC | 2260 |
| ATTGCATTCC | AGCCTTGGCG | ACAGAGCGAG | ACTCCATCTA | AAAAAAAAA | | 2310 |

( 2 ) INFORMATION FOR SEQ ID NO:10:

( i ) SEQUENCE CHARACTERISTICS:
        ( A ) LENGTH: 652 amino acids
        ( B ) TYPE: amino acid
        ( D ) TOPOLOGY: linear ( i i ) MOLECULE TYPE: protein ( x i ) SEQUENCE DESCRIPTION: SEQ ID NO:10:

| | | | | | | | | | | | | | | |
|---|---|---|---|---|---|---|---|---|---|---|---|---|---|---|
| Met | Val | Ser | Trp | Gly | Arg | Phe | Ile | Cys | Leu | Val | Val | Thr | Met | Ala |
| 1 | | | | 5 | | | | | 10 | | | | | 15 |
| Thr | Leu | Ser | Leu | Ala | Arg | Pro | Ser | Phe | Ser | Leu | Val | Glu | Asp | Thr | Thr |
| | | | 20 | | | | | 25 | | | | | 30 | | |
| Leu | Glu | Pro | Glu | Gly | Ala | Pro | Tyr | Trp | Thr | Asn | Thr | Glu | Lys | Met | Glu |
| | | | 35 | | | | 40 | | | | | 45 | | | |
| Lys | Arg | Leu | His | Ala | Val | Pro | Ala | Ala | Asn | Thr | Val | Lys | Phe | Arg | Cys |
| | 50 | | | | | 55 | | | | | 60 | | | | |
| Pro | Ala | Gly | Gly | Asn | Pro | Met | Pro | Thr | Met | Arg | Trp | Leu | Lys | Asn | Gly |
| 65 | | | | | 70 | | | | | 75 | | | | | 80 |
| Lys | Glu | Phe | Lys | Gln | Glu | His | Arg | Ile | Gly | Gly | Tyr | Lys | Val | Arg | Asn |
| | | | | 85 | | | | | 90 | | | | | 95 | |
| Gln | His | Trp | Ser | Leu | Ile | Met | Glu | Ser | Val | Val | Pro | Ser | Asp | Lys | Gly |
| | | | 100 | | | | | 105 | | | | | 110 | | |
| Asn | Tyr | Thr | Cys | Val | Val | Glu | Asn | Glu | Tyr | Gly | Ser | Ile | Asn | His | Thr |

-continued

|     |     |     | 115 |     |     |     |     | 120 |     |     |     |     | 125 |     |
|---|---|---|---|---|---|---|---|---|---|---|---|---|---|---|

Tyr His Leu Asp Val Val Glu Arg Ser Pro His Arg Pro Ile Leu Gln
    130                     135                 140

Ala Gly Leu Pro Ala Asn Ala Ser Thr Val Val Gly Gly Asp Val Glu
145                 150                 155                         160

Phe Val Cys Lys Val Tyr Ser Asp Ala Gln Pro His Ile Gln Trp Ile
                165                 170                 175

Lys His Val Glu Lys Asn Gly Ser Lys Tyr Gly Pro Asp Gly Leu Pro
            180                 185                 190

Tyr Leu Lys Val Leu Lys His Ser Gly Ile Asn Ser Ser Asn Ala Glu
        195                 200                 205

Val Leu Ala Leu Phe Asn Val Thr Glu Ala Asp Ala Gly Glu Tyr Ile
    210                 215                 220

Cys Lys Val Ser Asn Tyr Ile Gly Gln Ala Asn Gln Ser Ala Trp Leu
225                 230                 235                         240

Thr Val Leu Pro Lys Gln Gln Ala Pro Gly Arg Glu Lys Glu Ile Thr
            245                 250                 255

Ala Ser Pro Asp Tyr Leu Glu Ile Ala Ile Tyr Cys Ile Gly Val Phe
            260                 265                 270

Leu Ile Ala Cys Met Val Val Thr Val Ile Leu Cys Arg Met Lys Asn
        275                 280                 285

Thr Thr Lys Lys Pro Asp Phe Ser Ser Gln Pro Ala Val His Lys Leu
    290                 295                 300

Thr Lys Arg Ile Pro Leu Arg Arg Gln Val Ser Ala Glu Ser Ser Ser
305                 310                 315                         320

Ser Met Asn Ser Asn Thr Pro Leu Val Arg Ile Thr Thr Arg Leu Ser
                325                 330                 335

Ser Thr Ala Asp Thr Pro Met Leu Ala Gly Val Ser Glu Tyr Glu Leu
            340                 345                 350

Pro Glu Asp Pro Lys Trp Glu Phe Pro Arg Asp Lys Leu Thr Leu Gly
        355                 360                 365

Lys Pro Leu Gly Glu Gly Cys Phe Gly Gln Val Val Met Ala Glu Ala
    370                 375                 380

Val Gly Ile Asp Lys Asp Lys Pro Lys Glu Ala Val Thr Val Ala Val
385                 390                 395                         400

Lys Met Leu Lys Asp Asp Ala Thr Glu Lys Asp Leu Ser Asp Leu Val
                405                 410                 415

Ser Glu Met Glu Met Met Lys Met Ile Gly Lys His Lys Asn Ile Ile
            420                 425                 430

Asn Leu Leu Gly Ala Cys Thr Gln Asp Gly Pro Leu Tyr Val Ile Val
        435                 440                 445

Glu Tyr Ala Ser Lys Gly Asn Leu Arg Glu Tyr Leu Arg Ala Arg Arg
    450                 455                 460

Pro Pro Gly Met Glu Tyr Ser Tyr Asp Ile Asn Arg Val Pro Glu Glu
465                 470                 475                         480

Gln Met Thr Phe Lys Asp Leu Val Ser Cys Thr Tyr Gln Leu Ala Arg
                485                 490                 495

Gly Met Glu Tyr Leu Ala Ser Gln Lys Cys Ile His Arg Asp Leu Ala
            500                 505                 510

Ala Arg Asn Val Leu Val Thr Glu Asn Asn Val Met Lys Ile Ala Asp
        515                 520                 525

Phe Gly Leu Ala Arg Asp Ile Asn Asn Ile Asp Tyr Tyr Lys Lys Thr
    530                 535                 540

```
Thr  Asn  Gly  Arg  Leu  Pro  Val  Lys  Trp  Met  Ala  Pro  Glu  Ala  Leu  Phe
545                 550                 555                           560

Asp  Arg  Val  Tyr  Thr  His  Gln  Ser  Asp  Val  Trp  Ser  Phe  Gly  Val  Leu
                    565                 570                      575

Met  Trp  Glu  Ile  Phe  Thr  Leu  Gly  Gly  Ser  Pro  Tyr  Pro  Gly  Ile  Pro
               580                      585                           590

Val  Glu  Glu  Leu  Phe  Lys  Leu  Leu  Lys  Glu  Gly  His  Arg  Met  Asp  Lys
          595                      600                      605

Pro  Ala  Asn  Cys  Thr  Asn  Glu  Leu  Tyr  Met  Met  Arg  Asp  Cys  Trp
          610                 615                 620

His  Ala  Val  Pro  Ser  Gln  Arg  Pro  Thr  Phe  Lys  Gln  Leu  Val  Glu  Asp
625                      630                      635                      640

Leu  Asp  Arg  Ile  Leu  Thr  Leu  Thr  Thr  Asn  Glu  Ile
                    645                      650
```

( 2 ) INFORMATION FOR SEQ ID NO:11:

( i ) SEQUENCE CHARACTERISTICS:
        ( A ) LENGTH: 734 base pairs
        ( B ) TYPE: nucleic acid
        ( C ) STRANDEDNESS: double
        ( D ) TOPOLOGY: linear ( i i ) MOLECULE TYPE: cDNA ( i x ) FEATURE:
        ( A ) NAME/KEY: CDS
        ( B ) LOCATION: 4..723

( x i ) SEQUENCE DESCRIPTION: SEQ ID NO:11:

```
CAT  ATG  CGG  CCC  TCC  TTC  AGT  TTA  GTT  GAG  GAT  ACC  ACA  TTA  GAG  CCA      48
     Met  Arg  Pro  Ser  Phe  Ser  Leu  Val  Glu  Asp  Thr  Thr  Leu  Glu  Pro
     1                   5                        10                       15

GAA  GGA  GCA  CCA  TAC  TGG  ACC  AAC  ACA  GAA  AAG  ATG  GAA  AAG  CGG  CTC      96
Glu  Gly  Ala  Pro  Tyr  Trp  Thr  Asn  Thr  Glu  Lys  Met  Glu  Lys  Arg  Leu
                    20                  25                       30

CAT  GCT  GTG  CCT  GCG  GCC  AAC  ACT  GTC  AAG  TTT  CGC  TGC  CCA  GCC  GGG     144
His  Ala  Val  Pro  Ala  Ala  Asn  Thr  Val  Lys  Phe  Arg  Cys  Pro  Ala  Gly
               35                       40                       45

GGG  AAC  CCA  ATG  CCA  ACC  ATG  CGG  TGG  CTG  AAA  AAC  GGG  AAG  GAG  TTT     192
Gly  Asn  Pro  Met  Pro  Thr  Met  Arg  Trp  Leu  Lys  Asn  Gly  Lys  Glu  Phe
          50                       55                       60

AAG  CAG  GAG  CAT  CGC  ATT  GGA  GGC  TAC  AAG  GTA  CGA  AAC  CAG  CAC  TGG     240
Lys  Gln  Glu  His  Arg  Ile  Gly  Gly  Tyr  Lys  Val  Arg  Asn  Gln  His  Trp
     65                       70                       75

AGC  CTC  ATT  ATG  GAA  AGT  GTG  GTC  CCA  TCT  GAC  AAG  GGA  AAT  TAT  ACC     288
Ser  Leu  Ile  Met  Glu  Ser  Val  Val  Pro  Ser  Asp  Lys  Gly  Asn  Tyr  Thr
80                       85                       90                       95

TGT  GTG  GTG  GAG  AAT  GAA  TAC  GGG  TCC  ATC  AAT  CAC  ACG  TAC  CAC  CTG     336
Cys  Val  Val  Glu  Asn  Glu  Tyr  Gly  Ser  Ile  Asn  His  Thr  Tyr  His  Leu
               100                      105                      110

GAT  GTT  GTG  GAG  CGA  TCG  CCT  CAC  CGG  CCC  ATC  CTC  CAA  GCC  GGA  CTG     384
Asp  Val  Val  Glu  Arg  Ser  Pro  His  Arg  Pro  Ile  Leu  Gln  Ala  Gly  Leu
          115                      120                      125

CCG  GCA  AAT  GCC  TCC  ACA  GTG  GTC  GGA  GGA  GAC  GTA  GAG  TTT  GTC  TGC     432
Pro  Ala  Asn  Ala  Ser  Thr  Val  Val  Gly  Gly  Asp  Val  Glu  Phe  Val  Cys
          130                      135                      140

AAG  GTT  TAC  AGT  GAT  GCC  CAG  CCC  CAC  ATC  CAG  TGG  ATC  AAG  CAC  GTG     480
Lys  Val  Tyr  Ser  Asp  Ala  Gln  Pro  His  Ile  Gln  Trp  Ile  Lys  His  Val
     145                      150                      155

GAA  AAG  AAC  GGC  AGT  AAA  TAC  GGG  CCC  GAC  GGG  CTG  CCC  TAC  CTC  AAG     528
Glu  Lys  Asn  Gly  Ser  Lys  Tyr  Gly  Pro  Asp  Gly  Leu  Pro  Tyr  Leu  Lys
```

```
                160                      165                      170                      175
GTT  CTC  AAG  CAC  TCG  GGG  ATA  AAT  AGT  TCC  AAT  GCA  GAA  GTG  CTG  GCT         576
Val  Leu  Lys  His  Ser  Gly  Ile  Asn  Ser  Ser  Asn  Ala  Glu  Val  Leu  Ala
               180                      185                      190

CTG  TTC  AAT  GTG  ACC  GAG  GCG  GAT  GCT  GGG  GAA  TAT  ATA  TGT  AAG  GTC         624
Leu  Phe  Asn  Val  Thr  Glu  Ala  Asp  Ala  Gly  Glu  Tyr  Ile  Cys  Lys  Val
               195                      200                      205

TCC  AAT  TAT  ATA  GGG  CAG  GCC  AAC  CAG  TCT  GCC  TGG  CTC  ACT  GTC  CTG         672
Ser  Asn  Tyr  Ile  Gly  Gln  Ala  Asn  Gln  Ser  Ala  Trp  Leu  Thr  Val  Leu
               210                      215                      220

CCA  AAA  CAG  CAA  GCG  CCT  GGA  AGA  GAA  AAG  GAG  ATT  ACA  GCT  TCC  CCA         720
Pro  Lys  Gln  Gln  Ala  Pro  Gly  Arg  Glu  Lys  Glu  Ile  Thr  Ala  Ser  Pro
     225                      230                      235

GAC  TAACTGGATC  C                                                                      734
Asp
240
```

( 2 ) INFORMATION FOR SEQ ID NO:12:

( i ) SEQUENCE CHARACTERISTICS:
        ( A ) LENGTH: 240 amino acids
        ( B ) TYPE: amino acid
        ( D ) TOPOLOGY: linear ( i i ) MOLECULE TYPE: protein ( x i ) SEQUENCE DESCRIPTION: SEQ ID NO:12:

```
Met  Arg  Pro  Ser  Phe  Ser  Leu  Val  Glu  Asp  Thr  Thr  Leu  Glu  Pro  Glu
  1                 5                      10                      15

Gly  Ala  Pro  Tyr  Trp  Thr  Asn  Thr  Glu  Lys  Met  Glu  Lys  Arg  Leu  His
                    20                      25                      30

Ala  Val  Pro  Ala  Ala  Asn  Thr  Val  Lys  Phe  Arg  Cys  Pro  Ala  Gly  Gly
               35                      40                      45

Asn  Pro  Met  Pro  Thr  Met  Arg  Trp  Leu  Lys  Asn  Gly  Lys  Glu  Phe  Lys
     50                      55                      60

Gln  Glu  His  Arg  Ile  Gly  Gly  Tyr  Lys  Val  Arg  Asn  Gln  His  Trp  Ser
 65                      70                      75                      80

Leu  Ile  Met  Glu  Ser  Val  Val  Pro  Ser  Asp  Lys  Gly  Asn  Tyr  Thr  Cys
                    85                      90                      95

Val  Val  Glu  Asn  Glu  Tyr  Gly  Ser  Ile  Asn  His  Thr  Tyr  His  Leu  Asp
                    100                     105                     110

Val  Val  Glu  Arg  Ser  Pro  His  Arg  Pro  Ile  Leu  Gln  Ala  Gly  Leu  Pro
               115                     120                     125

Ala  Asn  Ala  Ser  Thr  Val  Val  Gly  Gly  Asp  Val  Glu  Phe  Val  Cys  Lys
     130                     135                     140

Val  Tyr  Ser  Asp  Ala  Gln  Pro  His  Ile  Gln  Trp  Ile  Lys  His  Val  Glu
145                      150                     155                     160

Lys  Asn  Gly  Ser  Lys  Tyr  Gly  Pro  Asp  Gly  Leu  Pro  Tyr  Leu  Lys  Val
                    165                     170                     175

Leu  Lys  His  Ser  Gly  Ile  Asn  Ser  Ser  Asn  Ala  Glu  Val  Leu  Ala  Leu
                    180                     185                     190

Phe  Asn  Val  Thr  Glu  Ala  Asp  Ala  Gly  Glu  Tyr  Ile  Cys  Lys  Val  Ser
               195                     200                     205

Asn  Tyr  Ile  Gly  Gln  Ala  Asn  Gln  Ser  Ala  Trp  Leu  Thr  Val  Leu  Pro
     210                     215                     220

Lys  Gln  Gln  Ala  Pro  Gly  Arg  Glu  Lys  Glu  Ile  Thr  Ala  Ser  Pro  Asp
225                      230                     235                     240
```

( 2 ) INFORMATION FOR SEQ ID NO:13:

( i ) SEQUENCE CHARACTERISTICS:
        ( A ) LENGTH: 1079 base pairs
        ( B ) TYPE: nucleic acid
        ( C ) STRANDEDNESS: double
        ( D ) TOPOLOGY: linear ( i i ) MOLECULE TYPE: cDNA ( i x ) FEATURE:
        ( A ) NAME/KEY: CDS
        ( B ) LOCATION: 4..1068

( x i ) SEQUENCE DESCRIPTION: SEQ ID NO:13:

```
CAT ATG CGG CCC TCC TTC AGT TTA GTT GAG GAT ACC ACA TTA GAG CCA        48
    Met Arg Pro Ser Phe Ser Leu Val Glu Asp Thr Thr Leu Glu Pro
    1               5                  10                  15

GAA GAG CCA CCA ACC AAA TAC CAA ATC TCT CAA CCA GAA GTG TAC GTG        96
Glu Glu Pro Pro Thr Lys Tyr Gln Ile Ser Gln Pro Glu Val Tyr Val
                20                  25                  30

GCT GCG CCA GGG GAG TCG CTA GAG GTG CGC TGC CTG TTG AAA GAT GCC       144
Ala Ala Pro Gly Glu Ser Leu Glu Val Arg Cys Leu Leu Lys Asp Ala
            35                  40                  45

GCC GTG ATC AGT TGG ACT AAG GAT GGG GTG CAC TTG GGG CCC AAC AAT       192
Ala Val Ile Ser Trp Thr Lys Asp Gly Val His Leu Gly Pro Asn Asn
        50                  55                  60

AGG ACA GTG CTT ATT GGG GAG TAC TTG CAG ATA AAG GGC GCC ACG CCT       240
Arg Thr Val Leu Ile Gly Glu Tyr Leu Gln Ile Lys Gly Ala Thr Pro
    65                  70                  75

AGA GAC TCC GGC CTC TAT GCT TGT ACT GCC AGT AGG ACT GTA GAC AGT       288
Arg Asp Ser Gly Leu Tyr Ala Cys Thr Ala Ser Arg Thr Val Asp Ser
80                  85                  90                  95

GAA ACT TGG TAC TTC ATG GTG AAT GTC ACA GAT GCC ATC TCA TCC GGA       336
Glu Thr Trp Tyr Phe Met Val Asn Val Thr Asp Ala Ile Ser Ser Gly
                100                 105                 110

GAT GAT GAG GAT GAC ACC GAT GGT GCG GAA GAT TTT GTC AGT GAG AAC       384
Asp Asp Glu Asp Asp Thr Asp Gly Ala Glu Asp Phe Val Ser Glu Asn
            115                 120                 125

AGT AAC AAC AAG AGA GCA CCA TAC TGG ACC AAC ACA GAA AAG ATG GAA       432
Ser Asn Asn Lys Arg Ala Pro Tyr Trp Thr Asn Thr Glu Lys Met Glu
        130                 135                 140

AAG CGG CTC CAT GCT GTG CCT GCG GCC AAC ACT GTC AAG TTT CGC TGC       480
Lys Arg Leu His Ala Val Pro Ala Ala Asn Thr Val Lys Phe Arg Cys
    145                 150                 155

CCA GCC GGG GGG AAC CCA ATG CCA ACC ATG CGG TGG CTG AAA AAC GGG       528
Pro Ala Gly Gly Asn Pro Met Pro Thr Met Arg Trp Leu Lys Asn Gly
160                 165                 170                 175

AAG GAG TTT AAG CAG GAG CAT CGC ATT GGA GGC TAC AAG GTA CGA AAC       576
Lys Glu Phe Lys Gln Glu His Arg Ile Gly Gly Tyr Lys Val Arg Asn
                180                 185                 190

CAG CAC TGG AGC CTC ATT ATG GAA AGT GTG GTC CCA TCT GAC AAG GGA       624
Gln His Trp Ser Leu Ile Met Glu Ser Val Val Pro Ser Asp Lys Gly
            195                 200                 205

AAT TAT ACC TGT GTG GTG GAG AAT GAA TAC GGG TCC ATC AAT CAC ACG       672
Asn Tyr Thr Cys Val Val Glu Asn Glu Tyr Gly Ser Ile Asn His Thr
        210                 215                 220

TAC CAC CTG GAT GTT GTG GAG CGA TCG CCT CAC CGG CCC ATC CTC CAA       720
Tyr His Leu Asp Val Val Glu Arg Ser Pro His Arg Pro Ile Leu Gln
    225                 230                 235

GCC GGA CTG CCG GCA AAT GCC TCC ACA GTG GTC GGA GGA GAC GTA GAG       768
Ala Gly Leu Pro Ala Asn Ala Ser Thr Val Val Gly Gly Asp Val Glu
240                 245                 250                 255
```

| | | | | | | | | | | | | | | | | |
|---|---|---|---|---|---|---|---|---|---|---|---|---|---|---|---|---|
| TTT | GTC | TGC | AAG | GTT | TAC | AGT | GAT | GCC | CAG | CCC | CAC | ATC | CAG | TGG | ATC | 816 |
| Phe | Val | Cys | Lys | Val<br>260 | Tyr | Ser | Asp | Ala | Gln<br>265 | Pro | His | Ile | Gln | Trp<br>270 | Ile | |
| AAG | CAC | GTG | GAA | AAG | AAC | GGC | AGT | AAA | TAC | GGG | CCC | GAC | GGG | CTG | CCC | 864 |
| Lys | His | Val | Glu<br>275 | Lys | Asn | Gly | Ser | Lys<br>280 | Tyr | Gly | Pro | Asp | Gly<br>285 | Leu | Pro | |
| TAC | CTC | AAG | GTT | CTC | AAG | CAC | TCG | GGG | ATA | AAT | AGT | TCC | AAT | GCA | GAA | 912 |
| Tyr | Leu | Lys<br>290 | Val | Leu | Lys | His | Ser<br>295 | Gly | Ile | Asn | Ser | Ser<br>300 | Asn | Ala | Glu | |
| GTG | CTG | GCT | CTG | TTC | AAT | GTG | ACC | GAG | GCG | GAT | GCG | GGG | GAA | TAT | ATA | 960 |
| Val | Leu<br>305 | Ala | Leu | Phe | Asn | Val<br>310 | Thr | Glu | Ala | Asp | Ala<br>315 | Gly | Glu | Tyr | Ile | |
| TGT | AAG | GTC | TCC | AAT | TAT | ATA | GGG | CAG | GCC | AAC | CAG | TCT | GCC | TGG | CTC | 1008 |
| Cys<br>320 | Lys | Val | Ser | Asn | Tyr<br>325 | Ile | Gly | Gln | Ala | Asn<br>330 | Gln | Ser | Ala | Trp | Leu<br>335 | |
| ACT | GTC | CTG | CCA | AAA | CAG | CAA | GCG | CCT | GGA | AGA | GAA | AAG | GAG | ATT | ACA | 1056 |
| Thr | Val | Leu | Pro | Lys<br>340 | Gln | Gln | Ala | Pro | Gly<br>345 | Arg | Glu | Lys | Glu | Ile<br>350 | Thr | |
| GCT | TCC | CCA | GAC | TAACTGGATC | C | | | | | | | | | | | 1079 |
| Ala | Ser | Pro | Asp<br>355 | | | | | | | | | | | | | |

( 2 ) INFORMATION FOR SEQ ID NO:14:

( i ) SEQUENCE CHARACTERISTICS:
        ( A ) LENGTH: 355 amino acids
        ( B ) TYPE: amino acid
        ( D ) TOPOLOGY: linear ( i i ) MOLECULE TYPE: protein ( x i ) SEQUENCE DESCRIPTION: SEQ ID NO:14:

| | | | | | | | | | | | | | | |
|---|---|---|---|---|---|---|---|---|---|---|---|---|---|---|
| Met<br>1 | Arg | Pro | Ser | Phe<br>5 | Ser | Leu | Val | Glu | Thr<br>10 | Thr | Leu | Glu | Pro<br>15 | Glu |
| Glu | Pro | Pro | Thr<br>20 | Lys | Tyr | Gln | Ile | Ser<br>25 | Gln | Pro | Glu | Val | Tyr<br>30 | Val | Ala |
| Ala | Pro | Gly | Glu<br>35 | Ser | Leu | Glu | Val<br>40 | Arg | Cys | Leu | Leu | Lys<br>45 | Asp | Ala | Ala |
| Val | Ile<br>50 | Ser | Trp | Thr | Lys | Asp<br>55 | Gly | Val | His | Leu | Gly<br>60 | Pro | Asn | Asn | Arg |
| Thr<br>65 | Val | Leu | Ile | Gly | Glu<br>70 | Tyr | Leu | Gln | Ile | Lys<br>75 | Gly | Ala | Thr | Pro | Arg<br>80 |
| Asp | Ser | Gly | Leu | Tyr<br>85 | Ala | Cys | Thr | Ala | Ser<br>90 | Arg | Thr | Val | Asp | Ser<br>95 | Glu |
| Thr | Trp | Tyr | Phe | Met<br>100 | Val | Asn | Val | Thr | Asp<br>105 | Ala | Ile | Ser | Ser | Gly<br>110 | Asp |
| Asp | Glu | Asp | Asp<br>115 | Thr | Asp | Gly | Ala<br>120 | Glu | Asp | Phe | Val | Ser<br>125 | Glu | Asn | Ser |
| Asn | Asn<br>130 | Lys | Arg | Ala | Pro | Tyr<br>135 | Trp | Thr | Asn | Thr | Glu<br>140 | Lys | Met | Glu | Lys |
| Arg<br>145 | Leu | His | Ala | Val | Pro<br>150 | Ala | Ala | Asn | Thr | Val<br>155 | Lys | Phe | Arg | Cys | Pro<br>160 |
| Ala | Gly | Gly | Asn | Pro<br>165 | Met | Pro | Thr | Met | Arg<br>170 | Trp | Leu | Lys | Asn | Gly<br>175 | Lys |
| Glu | Phe | Lys | Gln<br>180 | Glu | His | Arg | Ile | Gly<br>185 | Gly | Tyr | Lys | Val | Arg<br>190 | Asn | Gln |
| His | Trp | Ser<br>195 | Leu | Ile | Met | Glu | Ser<br>200 | Val | Val | Pro | Ser | Asp<br>205 | Lys | Gly | Asn |
| Tyr | Thr | Cys | Val | Val | Glu | Asn | Glu | Tyr | Gly | Ser | Ile | Asn | His | Thr | Tyr |

```
                    210                      215                     220
His Leu Asp Val Val Glu Arg Ser Pro His Arg Pro Ile Leu Gln Ala
225                     230                     235                     240
Gly Leu Pro Ala Asn Ala Ser Thr Val Val Gly Gly Asp Val Glu Phe
                245                     250                     255
Val Cys Lys Val Tyr Ser Asp Ala Gln Pro His Ile Gln Trp Ile Lys
                260                     265                     270
His Val Glu Lys Asn Gly Ser Lys Tyr Gly Pro Asp Gly Leu Pro Tyr
            275                     280                     285
Leu Lys Val Leu Lys His Ser Gly Ile Asn Ser Ser Asn Ala Glu Val
        290                     295                     300
Leu Ala Leu Phe Asn Val Thr Glu Ala Asp Ala Gly Glu Tyr Ile Cys
305                     310                     315                     320
Lys Val Ser Asn Tyr Ile Gly Gln Ala Asn Gln Ser Ala Trp Leu Thr
                325                     330                     335
Val Leu Pro Lys Gln Gln Ala Pro Gly Arg Glu Lys Glu Ile Thr Ala
            340                     345                     350
Ser Pro Asp
        355
```

( 2 ) INFORMATION FOR SEQ ID NO:15:

( i ) SEQUENCE CHARACTERISTICS:
        ( A ) LENGTH: 39 base pairs
        ( B ) TYPE: nucleic acid
        ( C ) STRANDEDNESS: single
        ( D ) TOPOLOGY: linear ( i i ) MOLECULE TYPE: other nucleic acid, synthetic DNA ( x i ) SEQUENCE DESCRIPTION: SEQ ID NO:15:

ATTCTTATGC TTCCCGATCA T YTTCAT-
CAT YTCCAT YTC                                  39

( 2 ) INFORMATION FOR SEQ ID NO:16:

( i ) SEQUENCE CHARACTERISTICS:
        ( A ) LENGTH: 21 base pairs
        ( B ) TYPE: nucleic acid
        ( C ) STRANDEDNESS: single
        ( D ) TOPOLOGY: linear ( i i ) MOLECULE TYPE: other nucleic acid, synthetic DNA ( x i ) SEQUENCE DESCRIPTION: SEQ ID NO:16:

TCAGAGATGG AGATGATGAA G                        21

( 2 ) INFORMATION FOR SEQ ID NO:17:

( i ) SEQUENCE CHARACTERISTICS:
        ( A ) LENGTH: 26 base pairs
        ( B ) TYPE: nucleic acid
        ( C ) STRANDEDNESS: single
        ( D ) TOPOLOGY: linear ( i i ) MOLECULE TYPE: other nucleic acid, synthetic DNA ( x i ) SEQUENCE DESCRIPTION: SEQ ID NO:17:

AATGGCTGGA TCCAGTTAGT CTGGGG                26

( 2 ) INFORMATION FOR SEQ ID NO:18:

( i ) SEQUENCE CHARACTERISTICS:
        ( A ) LENGTH: 30 base pairs

-continued

```
( B ) TYPE: nucleic acid
( C ) STRANDEDNESS: single
( D ) TOPOLOGY: linear ( i i ) MOLECULE TYPE: other nucleic acid, synthetic DNA ( x i ) SEQUENCE DESCRIPTION: SEQ ID NO:18:

GAAGGAGGGC CGCATATGGG ACAAGGTTGC                                       30
```

WATER-SOLUBLE MUTEIN OF FGF RECEPTOR, DNA AND PRODUCTION THEREOF

This is a continuation of application Ser. No. 08/149,664 now abandoned filed on Nov. 9, 1993 which is a continuation of Ser. No. 07/743,369 now abandoned, filed as PCT/JP91/00557 Apr. 25, 1991.

FIELD OF THE INVENTION

The present invention relates to a water-soluble mutein of an animal protein which acts as a receptor for a fibroblast growth factor (hereinafter also referred to as FGF) protein, a recombinant DNA coding for the mutein and a technique for producing the mutein.

BACKGROUND OF THE INVENTION

FGFs include acidic fibroblast growth factors (hereinafter also referred to as aFGFs) having a molecular weight of about 16,000 and an isoelectric point of 5 to 7 which are localized in hypothalami, brains and retinas, and basic fibroblast growth factors (hereinafter also referred to as bFGFs) having a molecular weight of about 17,000 and an isoelectric point of 8 to 10 which widely occur in various tissues and organs. They both are characterized by strong heparin-binding ability, and at first were isolated as factors exhibiting strong growth promoting action on fibroblasts. It has thereafter become clear that they exhibit growth promoting action on almost all mesoderm-derived cells. In particular, they are generally known as growth promoting factors or angiogenic factors for endothelial cells. Most cancer cells are said to produce bFGFs, which promote growth of cancer cells themselves.

It is considered that the mutual interaction between FGFs and FGF receptors existing on the surfaces of cells is essential to the action of FGFs on various cells. Further, it is suggested that the aFGF and the bFGF possibly bind to a common receptor. However, this is not clear in all cases.

As described above, although FGF receptors play an important role in various cells, the facts are not clear as to the properties of FGF receptors as proteins and their genes. There is no known report that an FGF receptor has been produced by recombinant DNA technology. If the FGF receptors can be produced in large amounts by using recombinant DNA technology, they can be used as pharmaceuticals, such as antitumor agents. In particular, one goal has been to establish a mass production method for the proteins which act as a receptor for human FGF.

In general, proteins of closely related animals have high homology in their amino acid sequences, and most of the different amino acid portions are derived by one point mutation of codons of their genes. The present inventors deduced that a portion of the DNA sequence of a chicken FGF receptor gene would be very similar to the DNA sequence of a gene coding for a protein acting as a receptor for human FGF. Based on this idea, the present inventors synthesized a DNA having the same nucleotide sequence with a portion of the chicken FGF receptor gene as a probe, and cloned a gene coding for a protein which acts as a receptor for human FGF from a human cell by using this DNA. Then, the present inventors constructed a recombinant DNA containing the above gene and cultivated a transformant transformed with the above recombinant DNA. As a result, the present inventors discovered that a protein acting as a receptor for human FGF was produced.

Further, the present inventors discovered that a water-soluble mutein of the animal protein having this activity for the FGF protein advantageously received the FGF protein.

The present inventors further investigated based on this information, and consequently completed the present invention.

SUMMARY OF THE INVENTION

The present invention provides:

(1) a water-soluble mutein of an animal protein having activity as a receptor for a fibroblast growth factor (FGF) protein, (2) a recombinant DNA having a nucleotide sequence coding for the water-soluble mutein of the above item (1), (3) a vector containing the recombinant DNA of the above item (2), (4) a transformant transformed with the vector of the above item (3), and (5) a process for producing the water-soluble mutein of the above item (1) which comprises cultivating the transformant of the above item (4) in a culture medium.

BRIEF DESCRIPTION OF THE DRAWINGS

FIGS. 1-1 and 1-2 show a portion of a nucleotide sequence (SEQ ID NO:1) of a cDNA coding for a protein having activity as a receptor for human FGF, the protein being produced in Example 1, and an amino acid sequence (SEQ ID NO:2) deduced therefrom;

FIG. 2 shows restriction enzyme maps of the cDNA of an FGF receptor obtained in Example 2;

FIGS. 3-1 through 3-4 show a nucleotide sequence (SEQ ID NO:3) of the cDNA of plasmid pTB1228 obtained in Example 2, and an amino acid sequence (SEQ ID NO:4) to be encoded, in the lower row;

FIGS. 4-1 through 4-4 show the nucleotide sequence (SEQ ID NO:5) of the cDNA of plasmid pTB1229 obtained in Example 2, and the amino acid sequence (SEQ ID NO:6) to be encoded, in the lower row;

FIGS. 7-1 through 7-6 show a nucleotide sequence (SEQ ID NO:7) of the cDNA of plasmid pTB1284 obtained in Example 3, and the amino acid sequence (SEQ ID NO:8) to be encoded, in the lower row;

FIGS. 8-1 through 8-5 shows a nucleotide sequence (SEQ ID NO:9) of the cDNA of plasmid pTB1283 obtained in Example 3, and the amino acid sequence (SEQ ID NO:10) to be encoded, in the lower row;

FIGS. 9-1 through 9-2 are a schematic representation showing the construction of plasmid pTB1289 obtained in Example 4;

FIGS. 10-1 and 10-2 are a schematic representation showing the construction of plasmid pTB1290 obtained in Example 4;

FIGS. 11-1 and 11-2 show a nucleotide sequence (SEQ ID NO:11) of the cDNA of plasmid pTB1289 obtained in Example 4, and an amino acid sequence (SEQ ID NO:12) of an extracellular domain of an FGF receptor produced thereby;

FIGS. 12-1 through 12-3 shows a nucleotide sequence (SEQ ID NO:13) of the cDNA of plasmid pTB1290 obtained in Example 4, and an amino acid sequence (SEQ ID NO:14) of an extracellular domain of an FGF receptor produced thereby;

DESCRIPTION OF THE PREFERRED EMBODIMENTS

Figure 2:
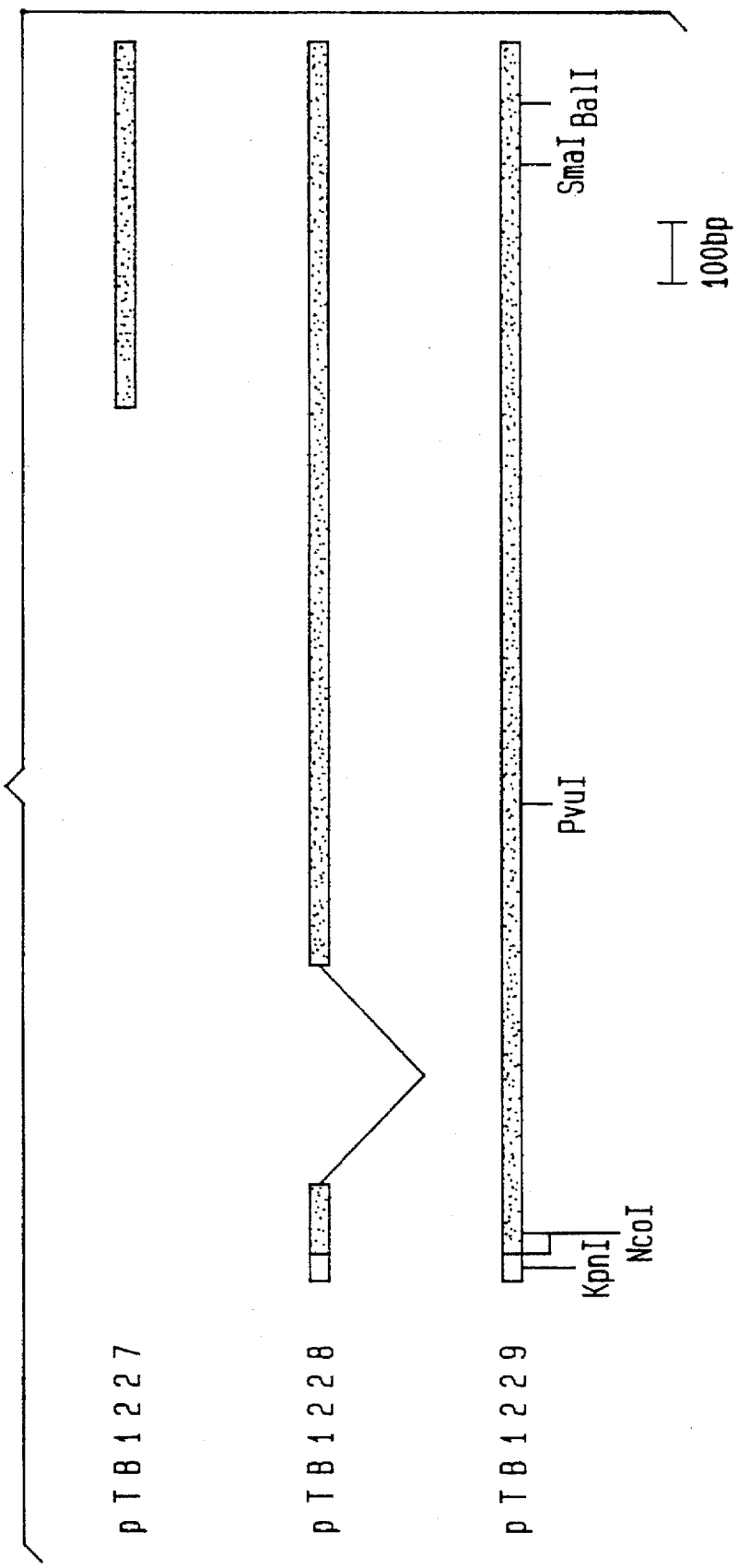

In the present invention, the FGF proteins include acidic FGFs, basic FGFs and muteins thereof. In particular, the basic FGFs and the muteins thereof are preferably used.

As the FGFs, mammal-derived FGFs are preferably used. Examples of the mammals include humans, monkeys, pigs, cattle, sheep and horses.

The muteins of the FGFs include a mutein in which at least one FGF-constituent amino acid is deleted from the FGF, a mutein in which at least one FGF-constituent amino acid is substituted for another amino acid, and a mutein in which at least one amino acid is added to the FGF, each mutein having FGF activity.

Specific examples of the FGF proteins include, for example, proteins disclosed in European Patent Publication Nos. 237,966, 281,822, 326,907 and 394,951.

The activity as a receptor for the FGF proteins includes the property of binding to the extracellular domains of the FGF proteins, and refers to activation of portions corresponding to tyrosine-phosphorylation enzymes in the intracellular domains by structural change due to binding to the FGF proteins. It is generally considered that such action of tyrosine phosphorylation is closely related to cell differentiation and cell proliferation.

As proteins which specifically bind to FGF protein molecules, anti-FGF antibodies are considered. However, antibody molecules have no enzyme activity and are independent of cell differentiation and cell proliferation. Accordingly, the claimed proteins which act as receptors for the FGF proteins are essentially different from any anti-FGF antibodies.

The animal proteins which act as receptors for the FGF proteins, which are basic materials of the water-soluble muteins of the present invention, include human, chicken, mouse, frog and fish proteins. The animal proteins are hereinafter also referred to as mature FGF receptors.

The human mature FGF receptors include a protein having an amino acid sequence formed by continuously connecting the amino acid sequence shown in FIG. 7, a protein having an amino acid sequence formed by continuously connecting the amino acid sequence shown in FIG. 8, a protein having an amino acid sequence described in *Nucleic Acids Research* 18, 1906 (1990), a protein having an amino acid sequence described as "flg" in *The EMBO Journal* 9, 2685 (1990), a protein having an amino acid sequence described as "bek" in *Molecular and Cellular Biology* 8, 5541–5544 (1988) and *The EMBO Journal* 9, 2685 (1990), and a protein having an amino acid sequence described as a protein expressing K-sam gene in *Proc. Natl. Acad. Sci. USA* 87, 4378–4382 (1990).

The chicken mature FGF receptors include a protein having an amino acid sequence described in *Science* 245, 57–60 (1989).

The mouse mature FGF receptors include a protein having an amino acid sequence described in *Proc. Natl. Acad. Sci. USA* 87, 4378–4382 (1990).

The water-soluble muteins of the present invention include muteins lacking at least one amino acid from the C-terminal side of the mature FGF receptor, and muteins lacking amino acid sequences corresponding to transmembrane domains of the mature FGF receptor.

The muteins lacking at least one amino acid from the C-terminal side of the mature FGF receptor include muteins lacking amino acid residues from the C-terminus to the transmembrane domains, namely portions corresponding to extracellular domains.

The extracellular domains may further lack 1 to 38 amino acid residues from the C-terminus of the extracellular domain. Furthermore, the extracellular domains may lack up to 123 amino acid residues from the C-terminus of the extracellular domain.

The muteins lacking amino acid sequences corresponding to transmembrane domains of the mature FGF receptors may further lack 1 to 11 amino acid residues from the C-terminus of the mutein which lacks the amino acid sequence corresponding to the transmembrane portion of a mature FGF receptor.

The above-mentioned deleted muteins may further lack at least one amino acid from the N-terminus simultaneously.

The deletion from the N-terminus include deletion of 1 to 257 amino acid residues, and preferably 1 to 131 amino acid residues from the N-terminus. The number of the amino acid is understood to be counted from an amino acid next to a signal sequence of the N-terminus.

In order to produce the water-soluble muteins of the present invention, site-directed mutagenesis is employed in addition to the conventional genetic engineering technique. This mutagenesis, which is well known, is described in R. F. Lather and J. P. Lecoq, *Genetic Engineering*, Academic Press, p.31–50 (1983). Mutagenesis directed to oligonucleotide is described in M. Smith and S. Gillam, *Genetic Engineering: Principles and Methods*, Plenum Press, vol. 3, p.1–32 (1981). A structural gene coding for the mutein of the present invention is produced, for example, by the steps of:

(a) hybridizing a single stranded DNA comprising one strand of a structural gene of the mature FGF receptor with a mutagenic oligonucleotide primer, (b) elongating the primer with DNA polymerase to form a mutational heteroduplex, and (c) replicating this mutational heteroduplex.

The size of the oligonucleotide primer depends on conditions required for stable hybridization of the primer to a gene region to which mutation is to be introduced, and on limitations in currently available methods of oligonucleotide synthesis. The factors (for example, the whole size and the size of a mismatching portion for a mutation site) to be considered in designing the oligonucleotide used for mutagenesis directed by the oligonucleotide are described by M. Smith and S. Gillam in the above literature. In general, the whole length of the oligonucleotide is such a length that stable, unique hybridization at the mutation site is optimized, and the extensions from the mutation site to the 5'- and the 3'-termini are adjusted in size so as to be sufficient to prevent mutation editing due to the exonuclease of DNA polymerase.

The expression vector having the DNA containing the nucleotide sequence coding for the above-mentioned mature FGF receptor can be prepared, for example, by the steps of:

(i) isolating RNA coding for the mature FGF receptor, (ii) synthesizing single stranded complementary DNA (cDNA) from the mRNA, followed by synthesis of double stranded DNA, (iii) introducing the complementary DNA into a plasmid,
(iv) transforming a host with the recombinant plasmid thus obtained,
(v) cultivating the transformant thus obtained, and then isolating the plasmid containing the desired DNA from the transformant by an appropriate method such as colony hybridization using a DNA probe,
(vi) cutting out the desired cloned DNA from the plasmid, and
(vii) ligating the cloned DNA downstream from a promoter in the vehicle.

The above-mentioned cDNA can also be produced by chemical synthesis.

The RNA coding for the mature FGF receptors can be obtained from various FGF receptor-producing cells such as human endothelium-derived cells and human fibroblasts. The human fibroblasts include WI38 (ATCC No. CCL-75) and IMR90 (ATCC No. CCL-186). The above cells WI38 and IMR90 appear in Catalogue of Cell Lines & Hybridomas, 5th edition (1985), published by The American Type Culture Collection.

Methods for preparing the RNA from the mature FGF receptor-producing cells include the guanidine thiocyanate method [J. M. Chirgwin et al., Biochemistry 18, 5294 (1979)].

Using the RNA thus obtained as a template, cDNA is synthesized by use of reverse transcriptase, for example, in accordance with the method of H. Okayama et al. [Molecular and Cellular Biology 2, 161 (1982); ibid. 3, 280 (1983)]. The cDNA thus obtained is introduced into the plasmid.

The plasmids into which the cDNA is introduced include, for example, pBR322 [Gene 2, 95 (1977)], pBR325 [Gene 4, 121 (1978)], pUC12 [Gene 19, 259 (1982)], pUC13 [Gene 19, 259 (1982)], pUC118 and pUC119 [Methods in Enzymology 153, 3–11 (1987)], each derived from Escherichia coli, and pUB110 derived from Bacillus subtilis [Biochemical and Biophysical Research Communication 112, 678 (1983)]. However, any other plasmid can be used as long as it is replicable and maintained in the host.

Methods for introducing the cDNA into the plasmid include, for example, the method described in T. Maniatis et al., Molecular Cloning, Cold Spring Laboratory, p.239 (1982).

As the plasmid into which the above cDNA is introduced, a plasmid may be used which is obtained by using the cDNA library in which E. coli. x1776 prepared by introducing cDNA synthesized from human normal diploid cell mRNA into the pCD vector [H. Okayama et al., Molecular Cell Biology 3, 280 (1983)] is used as a host. The above cDNA library is available from Dr. Okayama, Research Institute for Microbial Diseases, Osaka University.

The plasmid thus obtained is introduced into the appropriate host cells such as Escherichia and Bacillus.

Examples of Escherichia described above include E. coli K12DH1 [Proc. Natl. Acad. Sci. USA 60, 160 (1968)], M103 [Nucleic Acids Research 9, 309 (1981)], JA221 [Journal of Molecular Biology 120, 517, (1978)], HB101 [Journal of Molecular Biology 41, 459 (1969)] and C600 [Genetics 39, 440 (1954)].

Examples of Bacillus described above include Bacillus subtilis MI114 [Gene 24, 255 (1983)] and 207-21 [Journal of Biochemistry 95, 87 (1984)].

The methods of transformation include, for example, the calcium chloride method and the calcium chloride/rubidium chloride method described in T. Maniatis et al., Molecular Cloning, Cold Spring Harbor Laboratory, p.249 (1982).

The desired clones are selected from the thus-obtained transformants by using known methods such as the colony hybridization method [Gene 10, 63 (1980)] and the DNA nucleotide sequence determination method [Proc. Natl. Acad. Sci. USA 74, 560 (1977)].

Thus, the microorganisms are obtained each of which carries the vector having the DNA containing the nucleotide sequence coding for the cloned mature FGF receptor.

Then, the plasmids are isolated from the microorganisms. Isolation methods include the alkali methods [H. C. Birnboim et al., Nucleic Acids Research 1, 1513 (1979)].

The plasmid having the DNA containing the nucleotide sequence coding for the cloned mature FGF receptor can be used as it is, or cut out by digestion with a restriction enzyme if desired.

The cloned gene is ligated downstream from the promoter in a vehicle (vector) suitable for expression, whereby the expression vector can be obtained.

The vectors include the above plasmids derived from E. coli (such as pBR322, pBR325, pUC12, pUC13, pUC118 and pUC119), plasmids derived from B. subtilis (such as pUB110, pTP5 and pC194), plasmids derived from yeast (such as pSH19 and pSH15), bacteriophages such as λphage, and animal viruses such as retroviruses and vaccinia viruses.

The gene has ATG as a translation initiating codon at the 5'-terminus thereof and may have TAA, TGA or TAG as a translation terminating codon at the 3'-terminus. Further, in order to express the gene, the promoter is ligated upstream therefrom. As the promoter used in the present invention, any promoter is available as long as it is suitable for expression corresponding to the host used for the gene expression.

When the host used for transformation is Escherichia, it is preferable to use a T7 promoter, a trp promoter, a lac promoter, a recA promoter, a λpL promoter, a lpp promoter or the like. When the host is Bacillus, it is preferable to use a SPO1 promoter, a SPO2 promoter, a penP promoter or the like. When the host is yeast, it is preferable to use a PHO5 promoter, a PGK promoter, a GAP promoter, an ADH promoter or the like. In particular, it is preferable that the host is Escherichia and the promoter is the trp promoter or the T7 promoter.

When the host is an animal cell, an SV40-derived promoter, a retrovirus promoter or the like can be used.

By using a vector containing the DNA thus constructed, the transformant is prepared.

Examples of the host cells include Escherichia, Bacillus, yeast and animal cells.

Specific examples of Escherichia and Bacillus described above include the strains described above.

Examples of the yeast described above include Saccharomyces cerevisiae AH22R, NA87-11A and DKD-5D.

Examples of the animal cells include monkey cell COS7, Vero, Chinese hamster ovary cell (CHO), mouse L cell and human FL cell.

The Escherichia described above is transformed, for example, according to the methods described in Proc. Natl. Acad. Sci. USA, 69, 2110 (1972), Gene, 17, 107 (1982) and the like.

The Bacillus is transformed, for example, according to the methods described in Molecular & General Genetics, 168, 111 (1979) and the like.

The yeast is transformed, for example, according to the method described in Proc. Natl. Acad. Sci. USA, 75, 1929 (1978).

The animal cells are transformed, for example, according to the method described in Viroloqy, 52, 456 (1973).

Thus, the transformant transformed with the vector containing the DNA is obtained.

When the Escherichia or Bacillus transformant is cultivated, a liquid medium is particularly suitable as a medium for cultivation. Carbon sources, nitrogen sources, inorganic compounds and others necessary for growth of the transformants are contained therein. The carbon sources include, for example, glucose, dextrin, soluble starch and sucrose. The nitrogen sources include inorganic or organic materials such as ammonium salts, nitrates, corn steep liquor, peptone, casein, meat extracts, soybean meal and potato extract solution. The inorganic compounds include, for example, calcium chloride, sodium dihydrogenphosphate and magnesium chloride. Further, yeast, vitamins, growth promoting factors and so on may be added thereto.

The pH of the medium is preferably from about 6 to 8.

As the medium used for cultivation of Escherichia, it is preferable to use, for example, M9 medium containing glucose and Casamino Acids (Miller, *Journal of Experiments in Molecular Genetics*, 431–433, Cold Spring Harbor Laboratory, New York, 1972). In order to make the promoter act efficiently, a drug such as 3β-indolylacrylic acid may be added thereto, if necessary.

When the host is Escherichia, the cultivation is usually carried out at about 15° to 43° C. for about 3 to 24 hours, with aeration or agitation if necessary.

When the host is Bacillus, the cultivation is usually carried out at about 30° to 40° C. for about 6 to 24 hours, with aeration or agitation if necessary.

When the yeast transformant is cultivated, there is used, for example, Burkholder minimum medium [K. L. Bostian et al., *Proc. Natl. Acad. Sci. USA*, 77, 4505 (1980)] as the culture medium. The pH of the medium is preferably adjusted to from about 5 to 8. The cultivation is usually carried out at about 20° to 35° C. for about 24 to 72 hours, with aeration or agitation if necessary.

When the animal cell transformant is cultivated, preferred examples of the culture media include MEM medium containing about 5 to 20% fetal calf serum [*Science*, 122, 501 (1952)], DMEM medium [*Virology*, 8, 396 (1959)], RPMI1640 medium [*Journal of the American Medical Association*, 199, 519 (1967)] and 199 medium [*Proceeding of the Society for the Biological Medicine*, 73, 1 (1950)]. The pH is preferably from about 6 to 8. The cultivation is usually carried out at about 30° to 40° C. for about 15 to 60 hours, with aeration or agitation if necessary.

The mutein of the present invention can be isolated and purified from the cultures described above, for example, by the following method.

When the mutein of the present invention is extracted from the cultivated cells, the cells are collected by methods known in the art after cultivation. Then, the collected cells are suspended in an appropriate buffer solution containing a protein denaturant such as guanidine hydrochloride to extract the desired mutein out of the cells. There is also suitably used the method that the cells are disrupted by ultrasonic treatment, lysozyme and/or freezing-thawing, followed by centrifugation to obtain the mutein of the present invention. In particular, the method using lysozyme in combination with ultrasonic treatment is preferred.

In order to purify the mutein of the present invention from a supernatant of the culture, suitable combinations of known separating and purifying methods per se can be used. These known separating and purifying methods include methods utilizing a solubility such as salt precipitation and solvent precipitation, methods mainly utilizing a difference in molecular weight such as dialysis, ultrafiltration, gel filtration chromatography and SDS-polyacrylamide gel electrophoresis, methods utilizing a difference in electric charge such as ion-exchange column chromatography, methods utilizing specific affinity such as affinity chromatography, methods utilizing a difference in hydrophobicity such as reverse-phase high performance liquid chromatography and methods utilizing a difference in isoelectric point such as isoelectro focusing electrophoresis.

The muteins of the present invention thus obtained can also be dialyzed and lyophilized to form dried powders. When serum albumin is added to the muteins of the present invention for storage, the muteins are preferably prevented from being adsorbed by containers.

Thus, the substantially pure water-soluble muteins of the present invention are obtained. The substantially pure water-soluble muteins of the present invention include muteins having a protein content of 95% (w/w) or more, and preferably muteins having a protein content of 98% (w/w) or more.

Examples of the muteins of the present invention obtained by recombinant DNA technology include a protein containing a polypeptide represented by an amino acid sequence shown in FIG. 11, and a protein containing a polypeptide represented by an amino acid sequence shown in FIG. 12. The above protein may have Met at the N-terminus thereof. To the C-termini of the water-soluble muteins of the present invention, amino acid sequences corresponding to the transmembrane domains or the intracellular domains may be added (the resulting polypeptide is hereinafter also referred to as amino acid adducts). Examples of such adducts include a polypeptide containing an amino acid sequence shown in FIG. 7, and a polypeptide containing an amino acid sequence shown in FIG. 8. The above polypeptides can be produced, for example, by preparing cDNAs by the methods described above, introducing the cDNAs into plasmids to prepare transformants, cultivating the transformants and purifying the products.

The activity of the thus-obtained water-soluble muteins or amino acid adducts of the present invention can be assayed based on the binding effect of FGFs to cells.

The cells transfected or transformed with the recombinant DNA of the present invention can produce a large amount of the muteins of the present invention, even in various cells which essentially produce only a small amount of the FGF receptors or do not produce them at all.

The expression plasmids containing the genes coding for the water-soluble muteins of the present invention can allow various cells to produce the muteins of the present invention by introducing the plasmids into the cells, so that the water-soluble muteins of the present invention can be produced in large amounts.

To the water-soluble muteins of the present invention, sugar chains may be added. The sugar chains may be any one found in known glycosylated proteins. Examples thereof include N-acetyl glycosamine, N-acetyl galactosamine, mannose, galactose, fucose and cyalic acid. The number of the sugar chains added to the muteins is at least one, and preferably 10 to 20.

Using the thus-obtained water-soluble muteins of the present invention or the amino acid adducts thereof, the FGF molecules can be prevented from binding to the FGF receptors naturally existing on the cell surfaces. The cell proliferation depending on FGF is inhibited by such prevention. For this reason, they can be used as therapeutic agents for multiple endocrine neoplasia, prostatic hypertrophy, diabetic retinitis or cancer. Their toxicity is low.

The muteins of the present invention or the amino acid adducts thereof can be produced by transfecting or transforming various animal cells (such as lymphocytic cells) originally free from the FGF receptors with the DNAs of the present invention. These cells can therefore be proliferated, subcultured, cell lines established or cloned in vitro for a long period of time by cultivation in FGF-containing culture media.

The above-mentioned animal cells of which proliferation becomes possible by using the DNAs of the present invention are cultivated in large amounts, whereby various useful substances essentially produced by these cells can be obtained in large amounts.

In addition, using antibodies prepared against the protein coded by the DNAs of the present invention and the water-soluble muteins of the present invention or the amino acid adducts thereof, cancer or prostatic hypertrophy can be diagnosed by detecting the amount of the FGF receptors expressed in the cells.

When the water-soluble muteins of the present invention or the amino acid adducts thereof are used as pharmaceutical preparations, they can be safely given to warm-blooded mammals (such as humans, mice, rats, hamsters, rabbits, dogs and cats) parenterally or orally, in a powder form as they are, or as pharmaceutical compositions (such as injections, tablets, capsules, solutions and ointments) with pharmaceutically acceptable carriers, excipients and diluents.

The injections are prepared by conventional methods using, for example, physiological saline or aqueous solutions containing glucose or other auxiliary agents. The pharmaceutical compositions such as tablets and capsules can also be prepared in accordance with conventional methods.

When the water-soluble muteins of the present invention or the amino acid adducts thereof are given to mammals as the above-mentioned pharmaceutical compositions, the dosage is, for example, about 0.2 μg/kg to 0.2 mg/kg a day, and more preferably about 2 μg/kg to 0.2 mg/kg.

Further, when the cell cultivation of the cells into which the genes coding for the water-soluble muteins of the present invention or the amino acid adducts thereof are introduced should be accelerated, the FGF is preferably added to a culture medium so as to be contained in an amount of about 0.01 to 10 μg, and more preferably in an amount of about 0.1 to 10 μg per liter of medium.

When nucleotides, amino acids and so on are indicated by the abbreviations in this specification and drawings, the abbreviations adopted by IUPAC-IUB Commission on Biochemical Nomenclature or commonly used in the art are employed. For example, the following abbreviations are used. When the optical isomer is capable of existing with respect to the amino acids, the L-form is represented unless otherwise specified.

DNA : Deoxyribonucleic acid
cDNA : Complementary deoxyribonucleic acid
A : Adenine
T : Thymine
G : Guanine
C : Cytosine
RNA : Ribonucleic acid
dATP : Deoxyadenosine triphosphate
dTTP : Deoxythymidine triphosphate
dGTP : Deoxyguanosine triphosphate
dCTP : Deoxycytidine triphosphate
ATP : Adenosine triphosphate
EDTA : Ethylenediaminetetraacetic acid
SDS : Sodium dodecyl sulfate
G or Gly : Glycine
A or Ala : Alanine
V or Val : Valine
L or Leu : Leucine
I or Ile : Isoleucine
S or Ser : Serine
T or Thr : Threonine
C or Cys : Cysteine
M or Met : Methionine
E or Glu : Glutamic acid
D or Asp : Aspartic acid
K or Lys : Lysine
R or Arg : Arginine
H or His : Histidine
F or Phe : Phenylalanine
Y or Tyr : Tyrosine
W or Trp : Tryptophan
P or Pro : Proline
N or Asn : Asparagine
Q or Gln : Glutamine The accession numbers and deposit dates of the transformants obtained in Examples described below are shown in Table 1. In Table 1, the IFO numbers indicate the deposition in the Institute for Fermentation, Osaka, Japan (IFO) and the FERM BP numbers indicate the deposition in the Fermentation Research Institute, the Agency of Industrial Science and Technology, the Ministry of International Trade and Industry, Japan (FRI) under the Budapest treaty.

TABLE 1

| Microorganism | IFO | FRI |
| --- | --- | --- |
| E. coli MV1184/ pTB1228 | IFO 15071 (July 24, 1990) | FERM BP-3041 (August 6, 1990) |
| E. coli MV1184 pTB1229 | IFO 15072 (July 24, 1990) | FERM BP-3042 (August 6, 1990) |
| E. coli MV1184 pTB1283 | IFO 15089 (September 13, 1990) | FERM BP-3214 (December 26, 1990) |
| E. coli MV1184 pTB1284 | IFO 15090 (September 13, 1990) | FERM BP-3215 (December 26, 1990) |
| E. coli MM294 (DE3)/ pLysS, pTB1289 | IFO 15091 (September 13, 1990) | FERM BP-3216 (December 26, 1990) |
| E. coli MM294 (DE3)/ pLysS, pTB1290 | IFO 15092 (September 13, 1990) | FERM BP-3217 (December 26, 1990) |
| CHO 1315-1023 | IFO 50326 (April 3, 1991) | FERM BP-3362 (April 16, 1991) |
| CHO 1316-172 | IFO 50327 (April 3, 1991) | FERM BP-3363 (April 16, 1991) |

The present invention will be described in more detail with the following Examples. It is understood of course that these Examples are not intended to limit the scope of the invention.

EXAMPLE 1

(1) Preparation of Human Cancer Cell Line Kato III mRNA-Derived cDNA Library mRNA was extracted from human cancer cell Line Kato III by using an mRNA separating kit (Fast Track, Invitrogen, USA). Using this mRNA as a template, a cDNA library was prepared by use of λphage vector λgt10 [T. V. Huynh et al., DNA Cloning, A Practical Approach, p.49, IRL Press, Oxford (1985)] according to the method of Watson and Jackson (C. J. Watson and J. F. Jackson, DNA Cloning, A Practical Approach, p.79, IRL Press, Oxford (1985)]. Starting from 10 μg of poly(A) RNA, the cDNA library whose host is E. coli. C600, HflA (T. V. Huynh et al., the same as above) comprising about $1.5 \times 10^6$ clones could be obtained.

(2) Isolation of Phage Containing cDNA of Protein Having Human bFGF Receiving Action and Determination of DNA Nucleotide Sequence Thereof Each of 10 agar plates was inoculated to about $1 \times 10^5$ clones with the above phage cDNA library using *E. coli* C600, HflA as a host, and then the cDNA of each plate was transferred to 2 nitrocellulose filters (Millipore, HATF filter). Then, phage DNA was exposed for denaturation by lysing with 0.5N NaOH solution and dried for fixation on the filters [T. Maniatis et al., *Molecular Cloning*, p.320, Cold Spring Harbor Laboratory (1982)].

On the other hand, an oligonucleotide having the following formula was chemically synthesized which was deduced from a portion (amino acid Nos. 529 to 541) of the amino acid sequence of the chicken bFGF receptor reported by P. Lee et al. [P. Lee et al., *Science* 7, 57 (1989)].
5'-ATTCTTATGCTTCCCGATCATQTTCATCATQTCCA-TQTC-3' Q: T/C (SEQ ID NO:15)

This oligonucleotide was reacted with T4 polynucleotide kinase (Takara Shuzo) in 50 µl of a reaction solution [oligonucleotide: 0.1 µg, 50 mM Tris-HCl (pH 8.0), 10 mM $MgCl_2$,10 mM mercaptoethanol, 50 µCi [$\gamma$-$^{32}$P]-ATP (>5000 Ci/mmole), 3 units of T4 polynucleotide kinase] at 37° C. for 1 hour to label the 5'-terminus of the oligonucleotide with $^{32}$p.

The oligonucleotide labeled by the method described above was hybridized as a probe with each of the replica filters on which the DNA was fixed. The hybridization reaction was carried out at 35° C. for 16 hours in 10 ml of a solution of 5×SSPE [180 mM NaCl, 10 mM $NaH_2PO_4$, 1 mM EDTA (pH 7.4)], 5×Denhardt's, 0.1% SDS and 100 µg/ml denatured salmon sperm DNA. After completion of the reaction, the filters were washed with a solution of 5×SSC (0.15M NaCl, 0.015M sodium citrate) and 0.1% SDS at room temperature for 30 minutes 3 times and further at 45° C. for 30 minutes twice [T. Maniatis et al., *Molecular Cloning*, p.309, Cold Spring Harbor Laboratory (1982)].

Radioautograms were taken from the washed filters and the radioautograms of the replica filters in sets of two filters were put together in layers to search the cell strains reactive to the probe.

Consequently, 3 cDNA clones reactive to the probe were obtained, and named λFRK1, λlFRK2 and λFRK3, respectively. A portion of the nucleotide sequence of each cDNA portion was determined by the dideoxynucleotide synthetic chain termination method [J. Messing et al., *Nucleic Acids Res.* 9, 309 (1981)].

As a result, the amino acid sequence of a portion of the protein having human FGF receiving action could be determined. The nucleotide sequence and the amino acid sequence deduced therefrom are indicated by the sequences shown in FIG. 1. The amino acid sequence is very similar to that of the reported chicken bFGF receptor, which shows that this cDNA is one coding for the protein having action of receiving the human FGF proteins.

The protein obtained here is considered to lack the portion corresponding to about 190 amino acid residues from the C-terminus of the chicken FGF receptor [*Science* 7, 57 (1989)]. However, the protein is considered to contain at least the amino acid sequence corresponding to the central transmembrane sequence to the N-terminus.

EXAMPLE 2

Each of the cDNA portions of 3 cDNA clones λFRK2 and λFRK3 obtained in Example 1 was inserted into the multi-cloning sites of plasmids pUC118 and pUC119 (Takara Shuzo) to transform *E. coli* MV1184, thereby obtaining each of transformants *E. coli* MV1184/pTB1227, *E. coli* MV1184/pTB1228 (IFO 15071, FERM BP-3041) and *E. coli* MV1184/pTB1229 (IFO 15072, FERM BP-3042).

FIG. 2 shows restriction enzyme maps of the cDNA portions of plasmids pTB1227, pTB1228 and pTB1229 obtained from these transformants.

The cleavage maps obtained by digesting the cDNA portions of pTB1227, pTB1228 and pTB1229 with restriction enzymes are shown. The restriction enzymes used are KpnI, NcoI, PvuI, SmaI and BalI.

Referring to FIG. 2, open squares show non-coding regions, closed squares show coding regions, and V shows a deleted portion.

Further, the determination of the nucleotide sequences of these cDNAs proved that the nucleotide sequence of cDNA clone pTB1229 which was longest consisted of 1954 nucleotides. The nucleotide sequence thereof and the amino acid sequence for which it codes are indicated by the amino acid sequence shown in FIG. 4. The cDNA of pTB1228 is indicated by the nucleotide sequence shown in FIG. 3. This lacks the 134th to 478th nucleotides and 1309th and 1314th nucleotides of the nucleotide sequence shown in FIG. 4. Consequently, the amino acid sequence encoded lacks $E^{37}$ to $K^{151}$, $V^{429}$ and $T^{430}$, and $R^{152}$ is changed to G. Furthermore, n pTB1228, the 1029th G of the nucleotide sequence (FIG. 4) of the cDNA of pTB1229 is changed to T. In addition, the cDNA of pTB1227 was found to correspond to the 1395th to 1954th. Even when the nucleotide sequences of these cDNAs are translated to amino acids, no translation termination codons appear. For this reason, it is believed that the carboxyl terminus of the human FGF receptor cannot be obtained without further cloning the 3'-terminal side. When the translated amino acids are compared to those of the chicken FGF receptor, they have about 66% homology. From this comparison, the signal peptide is presumed to consist of 21 amino acids of $M^1$ to $A^{21}$ in both of FIG. 3 and FIG. 4. Similarly, the transmembrane sequence is presumed to consist of $I^{379}$ to $C^{391}$ in FIG. 4 which corresponds to $I^{264}$ to $C^{276}$ in FIG. 3.

EXAMPLE 3

(1) cDNA was synthesized by using the mRNA obtained in Example 1 described above and a cDNA synthesis kit (cDNA synthesis system, Plus, Amersham, U. K. ).

Primer 5'-TCAGAGATGGAGATGATGAAG-3' (21-mer) (SEQ ID NO:16) was synthesized based on the cDNA nucleotide sequence (1618–1638) obtained Example 2 described above, and the portion coding for the C-terminus of the FGF receptor was amplified to the cDNA obtained above together with oligo(dT)$_{12-18}$ (Amersham, U.K.) by the PCR (polymerase chain reaction) method. The amplified DNA fragment was cloned to the SmaI site of plasmid vector pUC118 (Takara Shuzo) to transform *E. coli* MV1184, thereby obtaining transformant *E. coli* MV1184/pTB1281.

The DNA sequence of plasmid pTB1281 obtained from this transformant was digested with restriction enzyme BamHI and KpnI. The length of the resulting cDNA was about 1 kbp.

Further, the nucleotide sequence of this cDNA was analyzed. As a result, this sequence was confirmed to contain a portion coding for $V^{533}$ to the carboxyl terminus in FIG. 4 of the FGF receptor and a non-translation region on the 3'-terminal side.

Figure 5:
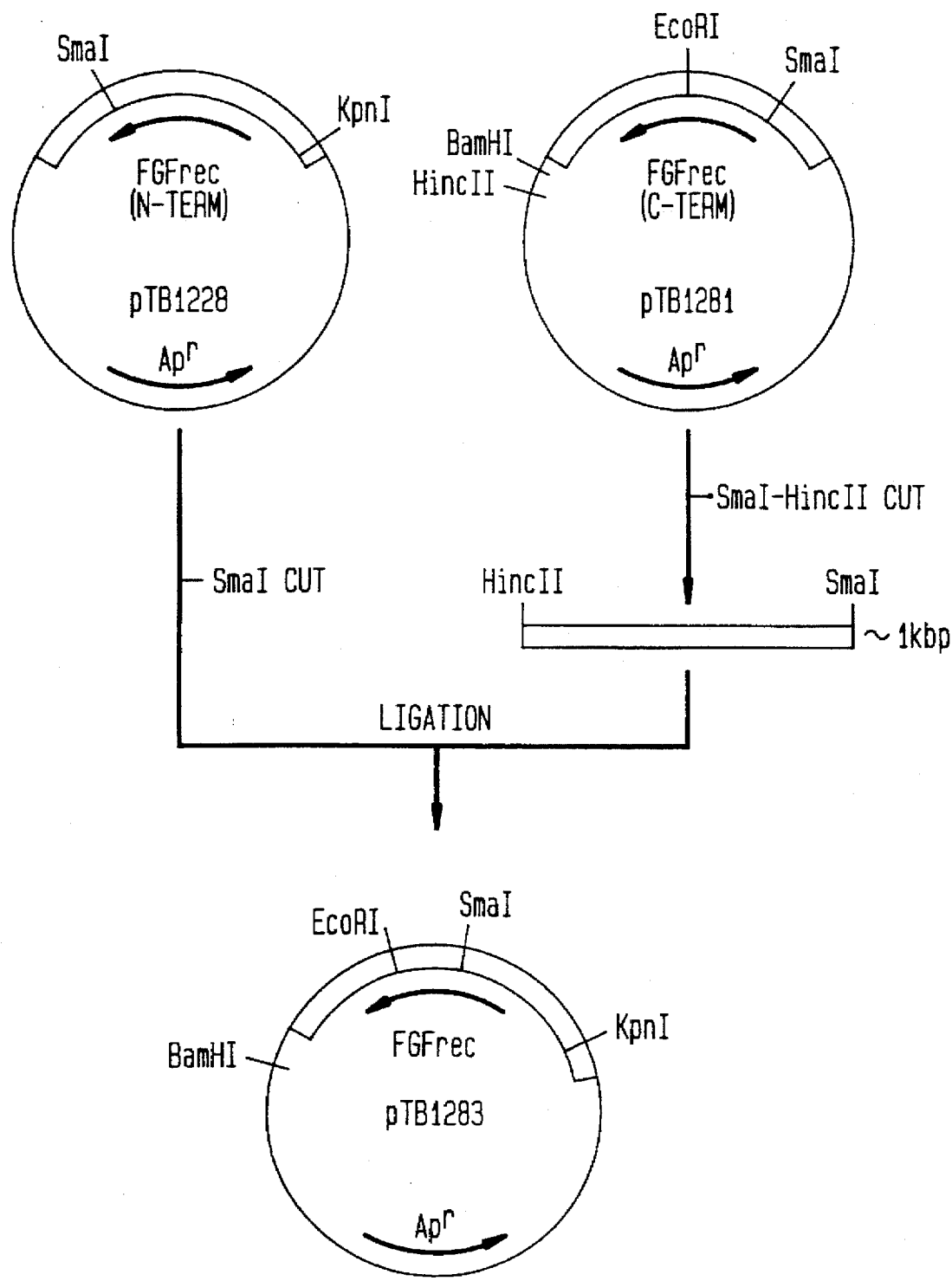
FIG. 5 is a schematic representation showing the construction of plasmid pTB1283 obtained in Example 3.
Figure 6:
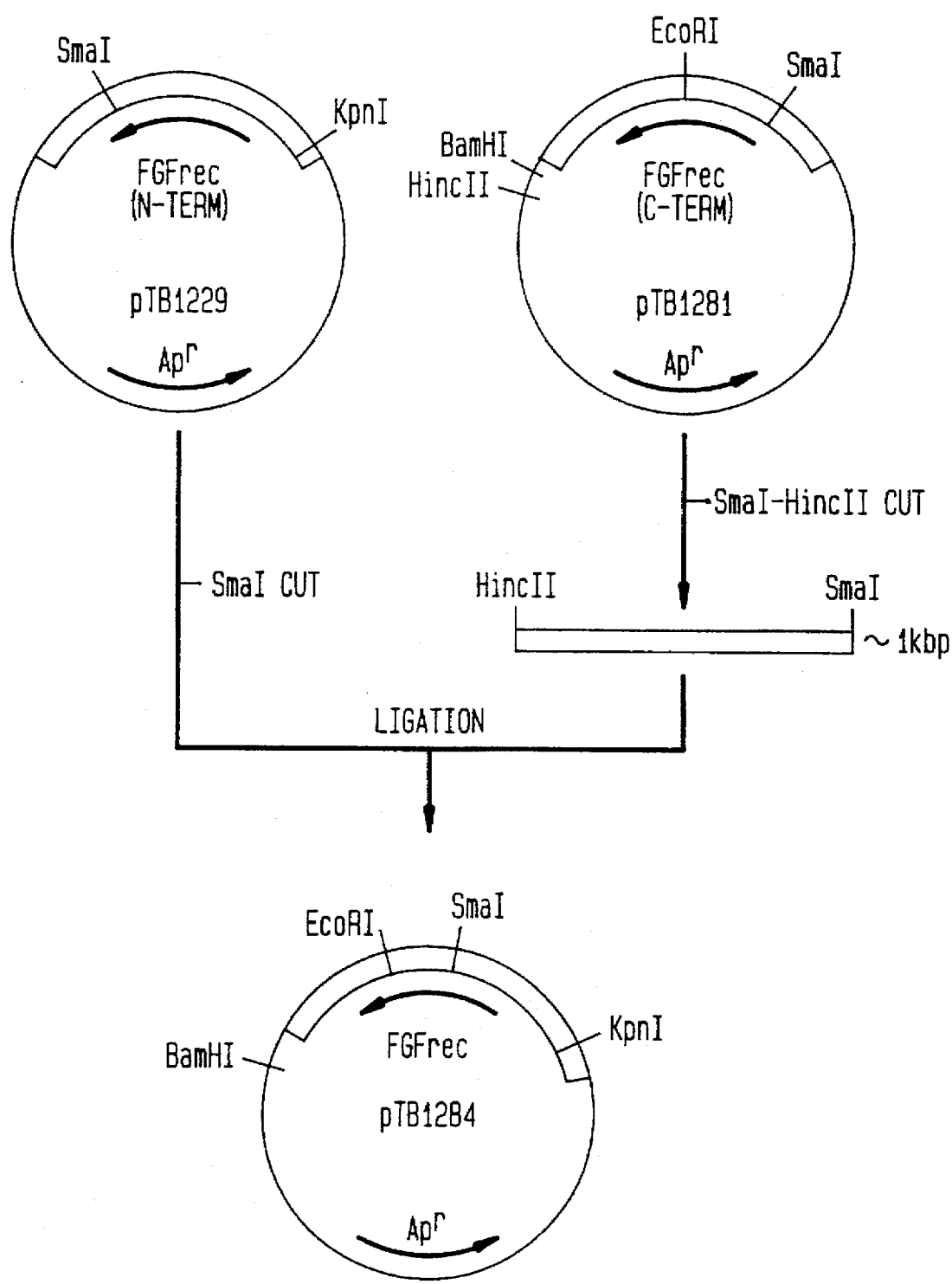
FIG. 6 is a schematic representation showing the construction of plasmid pTB1284 obtained in Example 3.

This cDNA nucleotide sequence overlaps with nucleotide No. 1618 and the succeeding nucleotides of the sequence shown in FIG. 3. Utilizing the recognition site of restriction enzyme SmaI existing in this portion, plasmid pTB1283 (FIG. 5) and plasmid pTB1284 (FIG. 6) having cDNA coding for the complete FGF receptor were constructed. Using these plasmid DNA, *E. coli* MV1184 was transformed to obtain two kinds of transformants E. coli MV1184/pTB1283 (IFO 15089, FERM BP-3214) and E. coli MV1184/pTB1284 (IFO 15090, FERM BP-3215).

The cDNA nucleotide sequence of plasmid pTB1284 is indicated by the nucleotide sequence shown in FIG. 7. The cDNA nucleotide sequence of plasmid pTB1283 is indicated by the nucleotide sequence shown in FIG. 8. This lacks the 134th to 478th nucleotides and 1309th to 1314th nucleotides of the nucleotide sequence shown in FIG. 7. Consequently, the amino acid sequence encoded lacks $E^{37}$ to $K^{151}$, $V^{429}$ and $T^{430}$ in FIG. 7; and $R^{152}$ in FIG. 7 is changed to G as the 37th amino acid residue in FIG. 8. Furthermore, the 1029th G of the nucleotide sequence (FIG. 7) of the cDNA of pTBa1284 is changed to T as the 684th nucleotide in FIG. 8.

(2) Expression of FGF Receptors in Animal Cells
(a) Construction of Plasmids pTB1313 and pTB1314 for Expression of FGF Receptors Two kinds of plasmids pTB1284 and pTB1283 obtained in the above item (1), each of which contains the whole structure region of the FGF receptor, were cleaved with restriction enzyme KpnI-BsmI. After reaction with T4 polymerase, BamHI linkers [CGGATCCG] were ligated to both terminal thereof, and a 2.6-kb or 2.2-kb DNA fragment was isolated.

Figure 13:
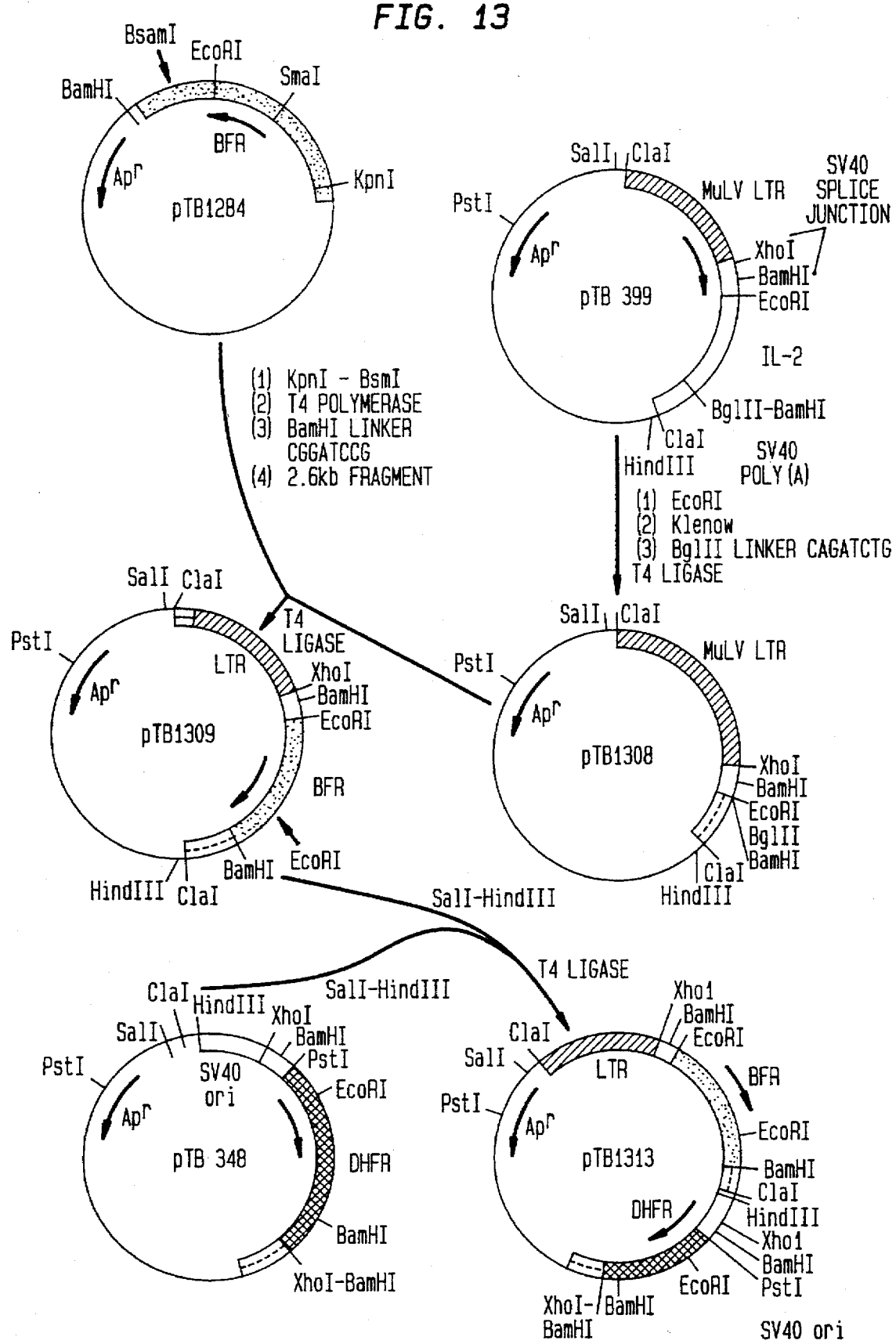
FIG. 13 is a schematic representation showing the construction of plasmid pTB1313 obtained in Example 3 (2)

On the other hand, animal cell vector pTB1308 was obtained by cleaving plasmid pTB399 (Cell Struct. Funct. 12, 205–217 (1987)) with EcoRI to remove the IL-2 cDNA region thereof, ligating a BglII linker [CAGATCTG] thereto after Klenow fragment reaction, followed by cleavage with BglII, and cyclizing the resulting DNA fragment of about 3.8 kb by using T4 ligase. The above 2.6-kb or 2.2-kb fragment of the FGF receptor cDNA was inserted into the BglII cleavage site of pTB1308, and expression plasmid pTB1309 or pTB1310 which can express the FGF receptor cDNA in an animal cell under the control of Abelson mouse leukemia virus (MuLV) LTR was constructed. Each of these plasmids was further cleaved with SalI-HindIII, and an expression unit portion (promoter gene-poly(A) signal) was inserted into the SalI-HindIII site upstream from the SV40 promoter of plasmid pTB348 for expression of hamster-dihydrofolate reductase (DHFR) [Cell Struct. Funct. 12, 205 (1987)] to construct each of plasmids pTB1313 and pTB1314. FIG. 13 shows the construction of plasmid pTB1313.

(b) Expression in Animal Cells

Monkey COS7 cells were inoculated in DMEM medium containing 10% fetal calf serum in a dish for tissue cultivation having a diameter of 6 cm, and the next day, the medium was exchanged for the same medium. After 4 hours, the cells were transfected with 10 µg of the DNA of plasmid pTB1313 or pTB1314 by the calcium phosphate method [Graham et al., Virology 52, 456 (1973)]. The next day, the transfected cells were added to DMEM medium containing 0.5% fetal calf serum, and cultivation was continued. After 48 hours, the culture solution and the cells were collected. The cells were washed twice with PBS, and then suspended in PBS. The suspension was treated with ultrasonication for a short time, followed by centrifugation at 15,000 rpm for 15 minutes to separate a supernatant from a cell residue. These culture solutions (0.5 ml, 5% trichloroacetic acid precipitation), cell extracts and the cell residues were analyzed by the Western blotting method after SDS-PAGE. As a primary antibody, rabbit polyclonal antibody was used which was obtained using a synthetic peptide (LVEDTTLEPE) as an antigen, the peptide corresponding to 27th to 36th of the amino acid sequence of the FGF receptor deduced from the FGF receptor cDNA.

As a result of the Western blotting, a product of about 140 to 150 kd was detected from the residue of the TB1313-infected COS7 cells, and a product of about 100 kd as detected from the residue of the pTB1314-infected COS7 cells.

EXAMPLE 4
(1) Construction of Expression System of Soluble Receptor in E. coli

Each of transformants E. coli MV1184/pTB1228 and E. coli MV1184/pTB1229 obtained in Example 2 described above was infected with helper phage KQ7, and a single stranded DNA was prepared from a culture medium. Using this single stranded DNA as a template, site-directed mutagenesis was carried out by use of two synthetic primers, (1)5'-AATGGCTGGATCCAGTTAGTCTGGGG-3' (26-mer) (SEQ ID NO:17) and (2)5'-GAAGGAGGGCCGCATATGGGACAAGGTTGC-3' (30-mer) (SEQ ID NO:18). This mutagenesis was conducted by using an in vitro mutagenesis system (Amersham, U.K.). As a result, plasmids pTB1285 and pTB1286 were obtained in each of which the 1152nd nucleotide of the nucleotide sequence of FIG. 7 was mutagenized to A by primer (1), a translation termination codon was introduced instead of $Y^{376}$ in FIG. 7, and further, the recognition site of restriction enzyme NdeI was introduced into the 1155th to 1160th nucleotides. Then, plasmids pTB1287 and pTB1288 were obtained in each of which the 83rd to 87th nucleotides were substituted for ATATG, the codon of $A_{21}$ in FIG. 7 was changed to the codon of M, and further, the recognition site of restriction enzyme BamHI was introduced into this portion.

Figure 9A:
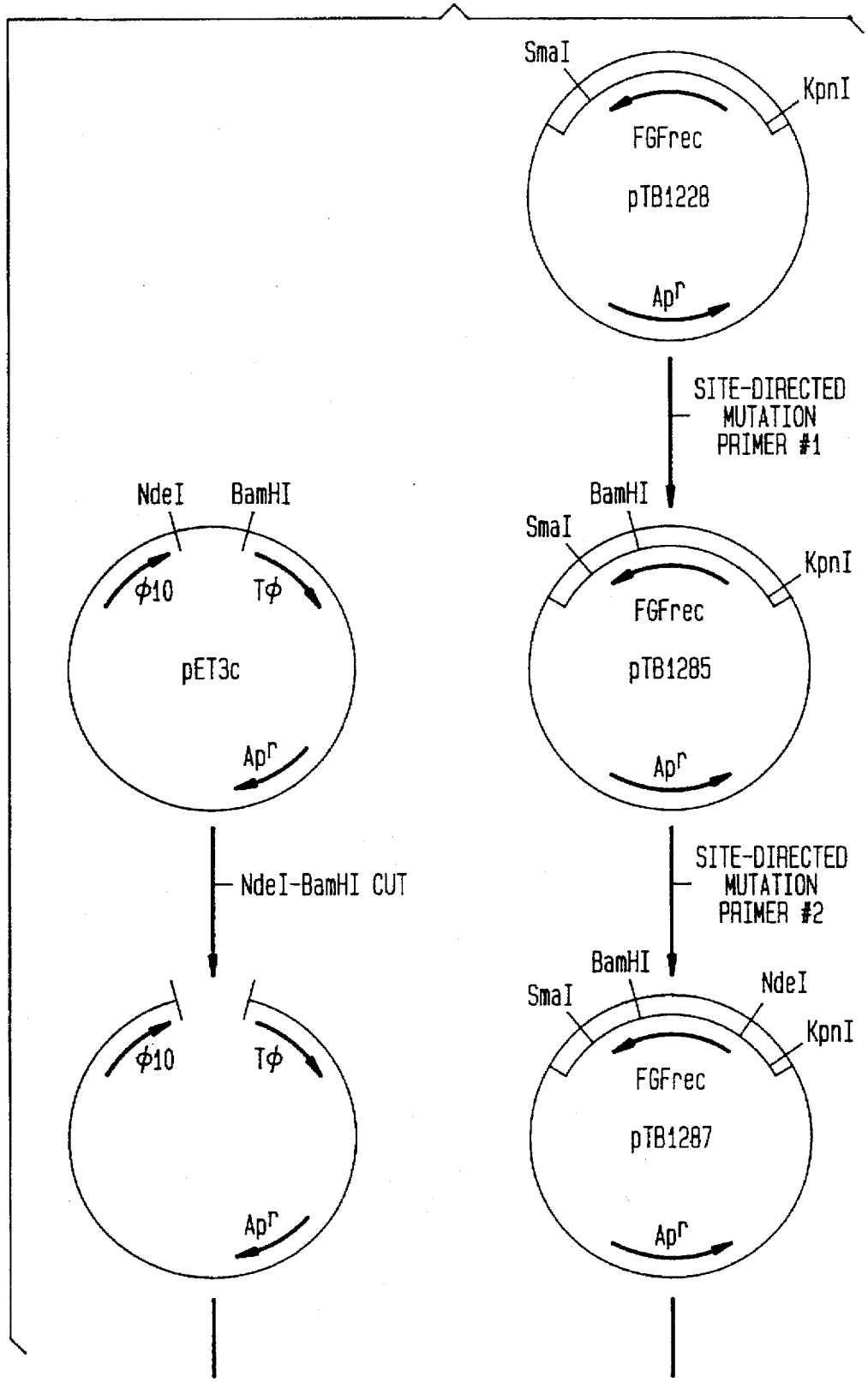
Figure 9B:
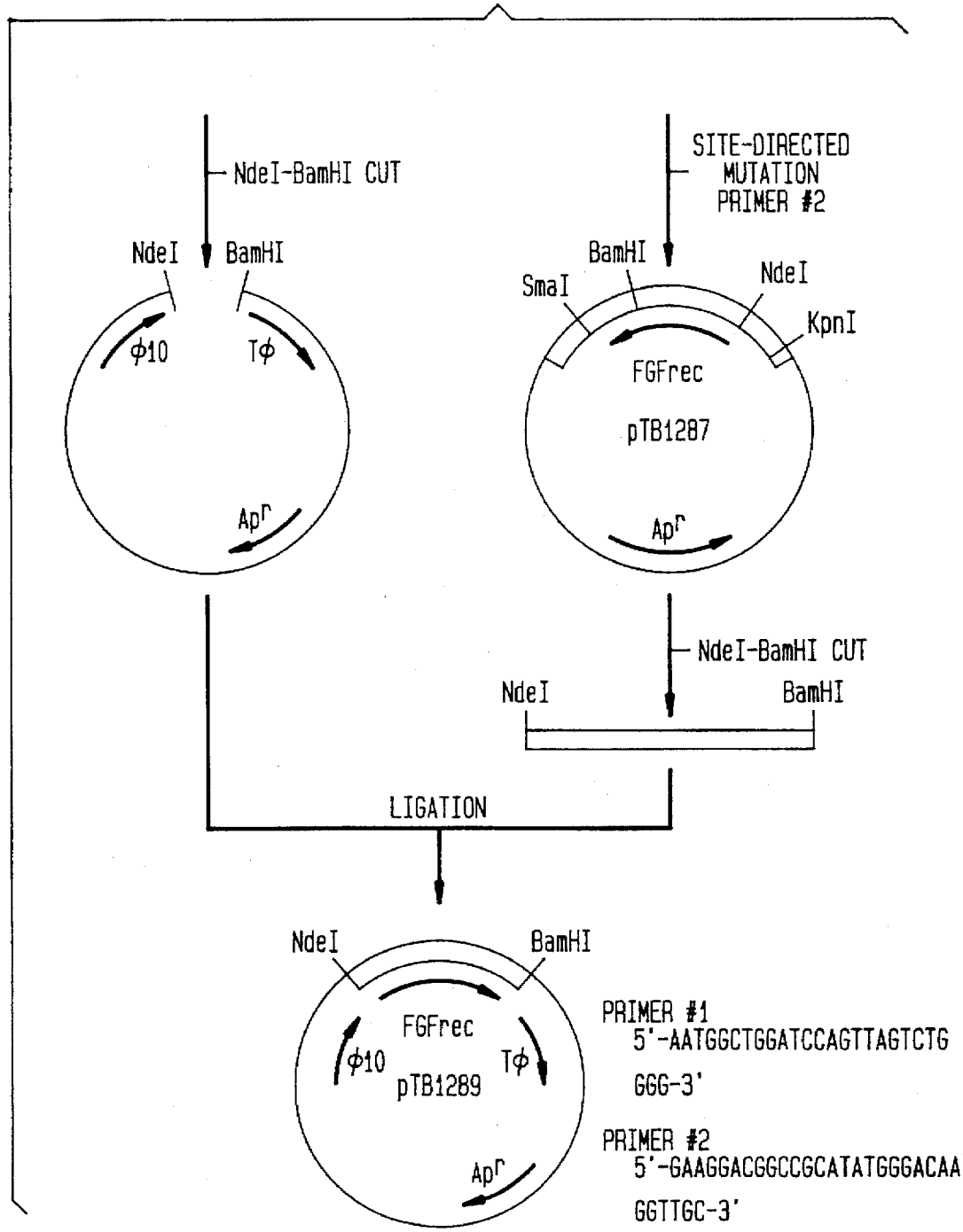
Figure 10A:
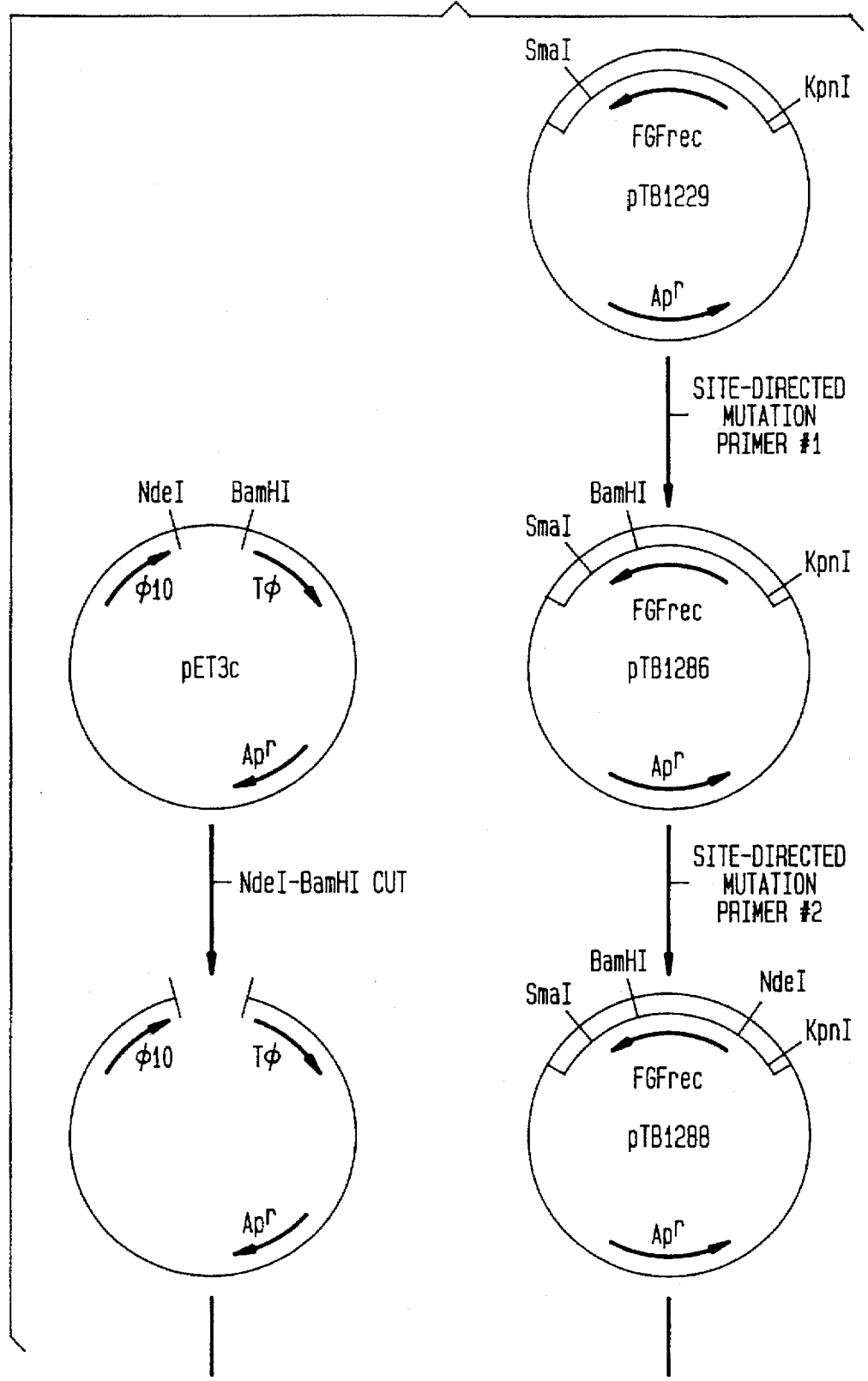
Figure 10B:
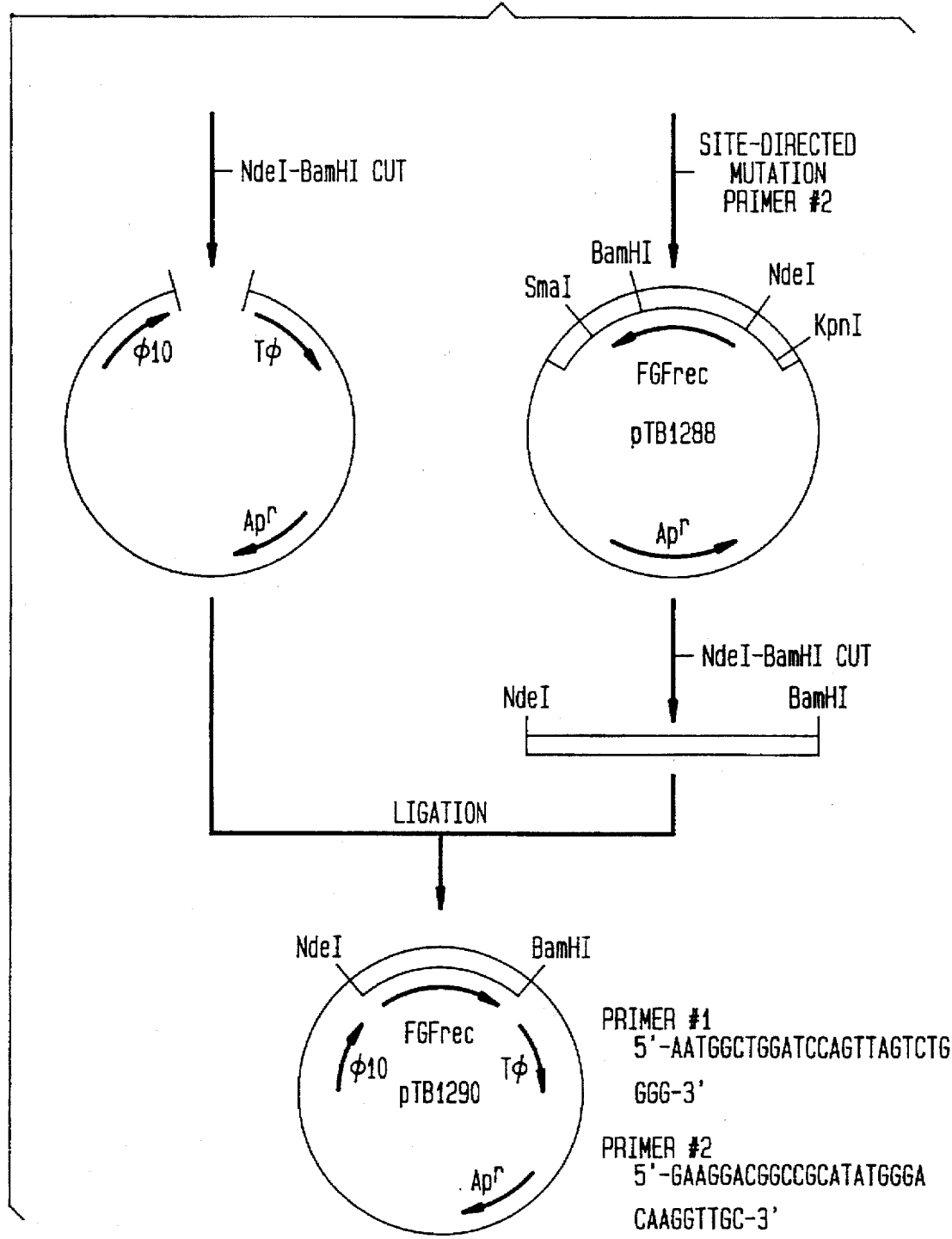

A fragment of 0.7 kbp or 1 kbp which was cut out from the DNA of each mutant with NdeI or BamHI was introduced downstream from the T7 promoter of plasmid pET3c to obtain plasmid pTB1289 or pTB1290. FIG. 9 shows the construction of plasmid pTB1289, and FIG. 10 shows the construction of plasmid pTB1290. E. coli MM294 (DE3)/pLysS was transformed using these plasmids, whereby transformants E. coli MM4294 (DE3)/pLysS, pTB1289 (IFO 15091, FERM BP-3216) and E. coli MM294 (DE3)/pLysS, pTB1290 (IFO 15092, FERM BP-3217) expressing an extracellular domain of the FGF receptor were obtained.
(2) Expression of Extracellular Domains of FGF Receptors in E. coli Each of E. coli MM294 (DE3)/pLysS, pTB1289 and E. coli MM294 (DE3)/pLysS, pTB1290 was cultivated in LB medium and expression was induced with isopropyl-β-D-thiogalactoside. Then, all proteins of the cells were examined by SDS-PAGE. As a result, bands specific for the respective transformants were confirmed by Coomassie Blue staining. From the relative positional relations to molecular weight markers, these bands were considered to agree with the estimated molecular weight of the proteins encoded in the cDNAs, and the production of the extracellular domains of the FGF receptors in E. coli was confirmed. As to the amino acid sequences of the extracellular domains of the resulting FGF receptors, the amino acid sequence of the protein expressed by E. coli MM294 (DE3)/pLysS, pTB1289 is indicated by the sequence shown in FIG. 11, and the amino acid sequence of the protein expressed by E. coli MM294 (DE3)/pLysS, pTB1290 is indicated by the sequence shown in FIG. 12.

(3) Expression of Extracellular Domains of FGF Receptors in Animal Cells
(a) Construction of Expression Plasmids pTB1315 and pTB1316

Two kinds of plasmids pTB1286 and pTB1285 obtained in the above (1), each of which has cDNA coding for the extracellular domain of the FGF receptors, were cleaved with restriction enzymes BstEII-BamHI to obtain 1.1-kb and 0.75-kb DNA fragments. On the other hand, plasmid pTS1309 for expression of the FGF receptors constructed in Example 3 (2) described above was cleaved with the same restriction enzymes, and replaced with each of the above-mentioned 1.1-kb and 0.75-kb fragments to construct expression plasmids pTB1311 and pTB1312.

pTB1311 and pTB1312 are plasmids which can express the cell domains of two kinds of FGF receptors under the control of MuLV LTR.

Figure 14:
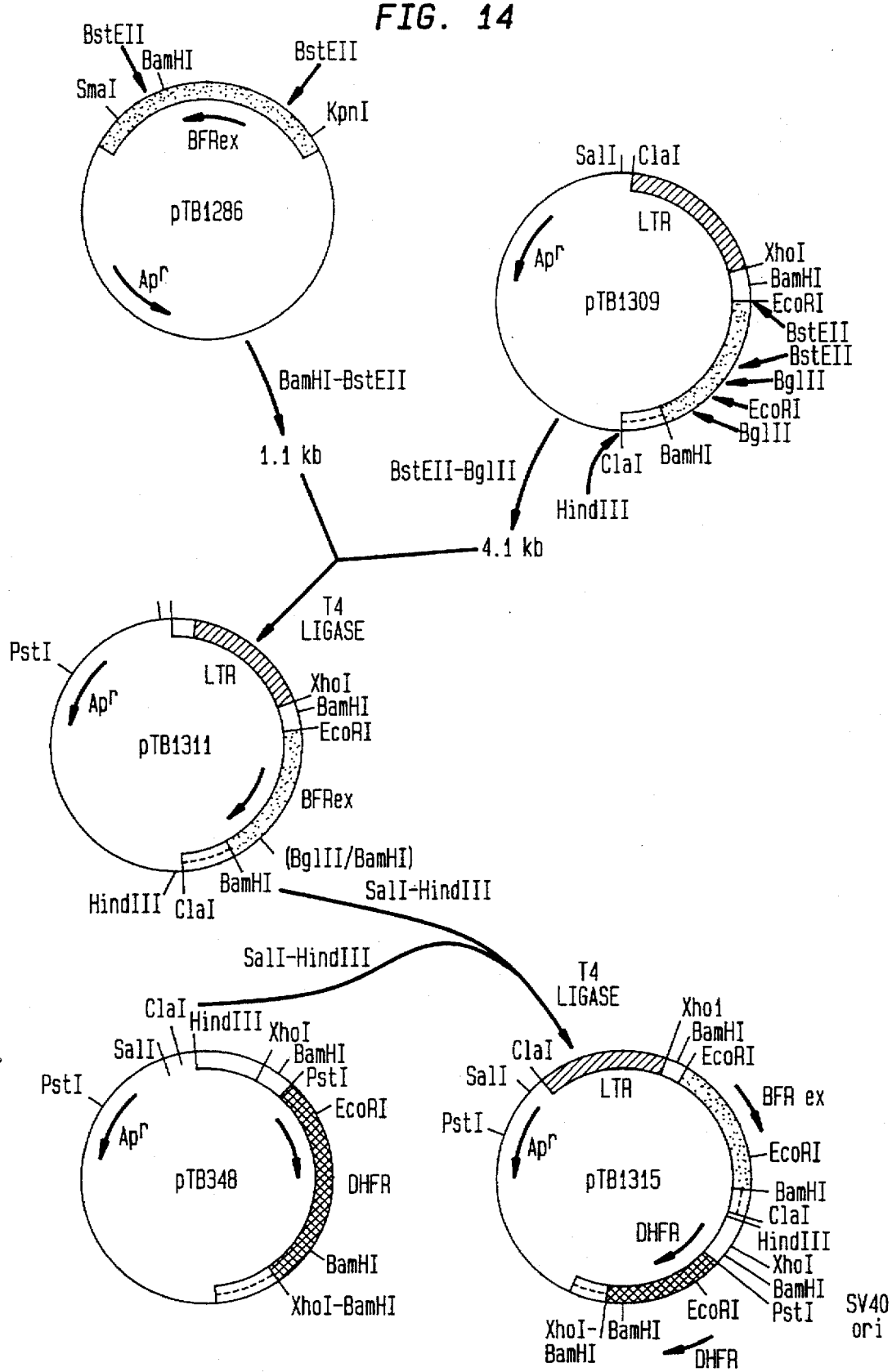
FIG. 14 is a schematic representation showing the construction of plasmid pTB1315 obtained in Example 4 (2)

Further, each of these plasmids was cleaved with SalI-HindIII to obtain an expression unit portion, which was inserted into plasmid pTB348 for expression of DHFR, using the SalI-HindIII fragment similarly with Example 3 (2) described above, thereby constructing plasmids pTB1315 and pTB1316. FIG. 14 shows the construction of plasmid pTB1315.

(b) Expression in Animal Cells

Monkey COS7 cells were transfected with plasmid pTB1313 or pTB1314 similarly with Example 3 (2) described above. For culture supernatants, cell extracts and cell residues, the infected cells were analyzed by western blotting. As a result, products of about 50 to 60 kd and about 35 to 50 kd were detected in the pTB1315-infected and pTB1316-infected COS7 cell culture solutions, respectively.

The water-soluble muteins of the animal proteins having action of receiving FGF proteins are useful as therapeutic agents.

EXAMPLE 5

Purification of Extracellular Domain of FGF Receptor Produced in *E. coli*

*E. coli* MM294 (DE3)/pLysS, pTB1289 was cultivated in a medium containing 35 µg/ml ampicillin and 10 µg/ml chloramphenicol at 37° C. When the turbidity reached Klett 120, isopropyl-β-D-thiogalactoside was added thereto to a final concentration of 0.5 mM, and cultivation was further continued for 2 hours. The cells were collected by centrifugation, and washed with phosphate buffered saline (PBS) cooled with ice. Then, the cells were collected again and stored at −20° C. until they were used.

The *E. coli* cells collected from 1 liter of the culture were suspended in 25 ml of an ice-cooled solution [7M urea, 0.1M Tris-HCl (pH 8) and 10 mM dithiothreitol (DTT)], and allowed to stand in ice for 1 hour.

Figure 15:
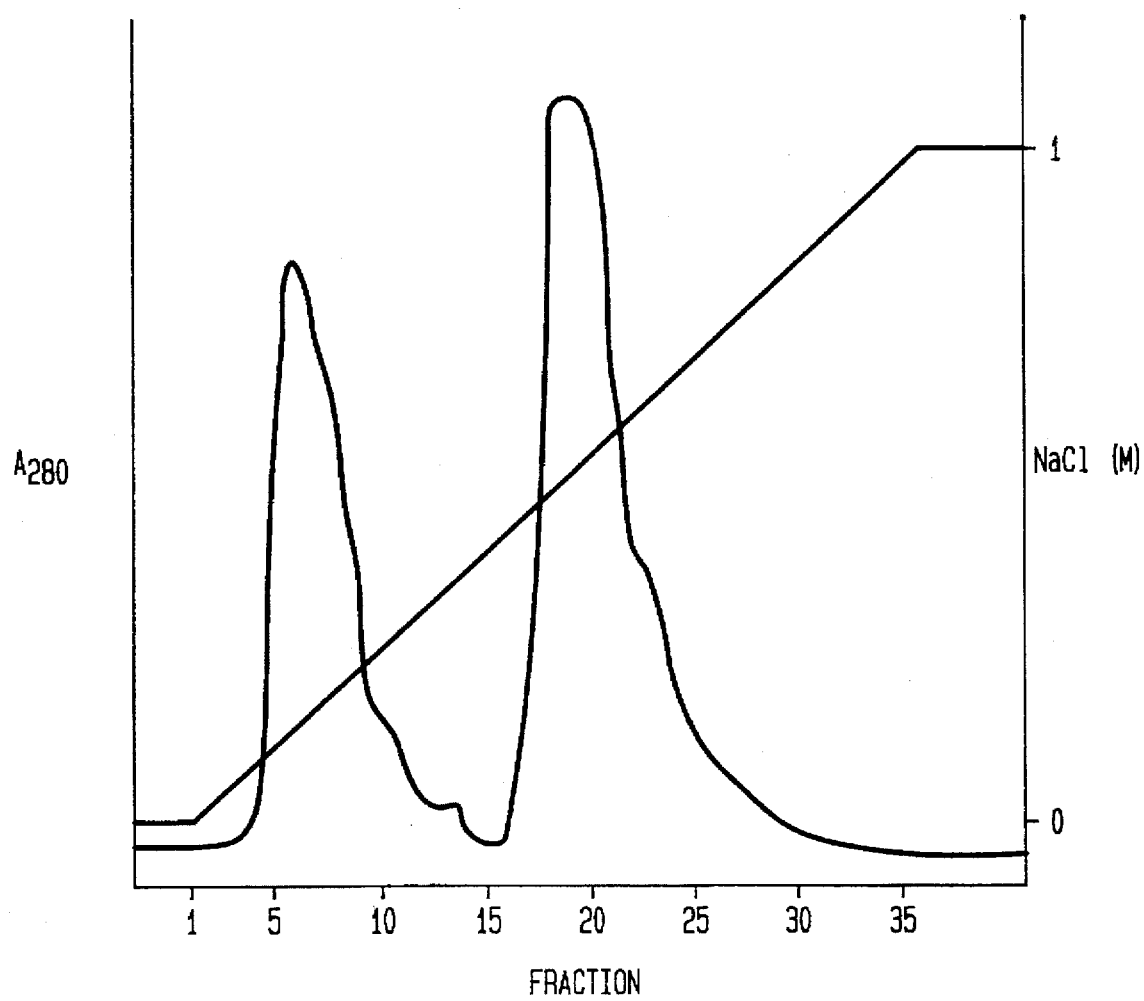
FIG. 15 is a graph which shows purification by a Q-Sepharose column of FGF receptor extracellular domain produced in *E. coli*.

After this solution was centrifuged at 17,000 rpm for 1 hour, the resulting supernatant was subjected to a Q-Sepharose column (2.5 cm in diameter by 5 cm) equilibrated with a buffer (7M urea, 0.1M Tris-HCl (pH 8) and 1 mM DTT). After washing with the buffer used to equilibrate the column, the column was eluted with a linear gradient of 0 to 1M NaCl at a flow rate of 1 ml/minute for 300 minutes, and fractionation was carried out every 8 minutes (FIG. 15). Each fraction was analyzed by the Western blotting method. As a result, it was observed that FGF receptor extracellular domain BFR-2ex was eluted in fraction Nos. 10 and 11 (the amino acid sequence thereof is shown in FIG. 11).

These eluted fractions of the Q-Sepharose column were further subjected to a Sephacryl S-200 column (2.5 cm in diameter by 100 cm) equilibrated with a buffer (7M urea, 0.1M Tris-HCl (pH 8), 0.3M NaCl and 2 mM DTT) to conduct gel filtration at a flow rate of 40 ml/hour. The results thus obtained revealed that FGF receptor extracellular domain BFR-2ex was eluted at the position corresponding to a molecular weight of about 32,000. The resulting fraction exhibited a single band by SDS-polyacrylamide gel electrophoresis and Coomassie Blue staining.

EXAMPLE 6

Establishment of CHO Cell Strains Producing Extracellular Domains of FGF Receptors Expression plasmids pTB1315 and pTB1316 described in Example 4, (3), (a) were each introduced into CHO dhfr⁻ cells [Urlanb et al., *Proc. Natl. Acad. Sci. USA* 77, 4216 (1980)] by the calcium phosphate method [Graham et al., *Virology* 52, 456 (1973)].

After two days, the medium was exchanged for a selection medium (DMEM containing 10% dialyzed fetal calf serum and 35 µg/ml proline), and cultivation was continued to obtain transformants which proliferated as dhfr⁺.

These CHO dhfr⁺ cells were cleaned by the limiting dilution method, and 24 clones were established for the respective CHO cells obtained by transfecting the respective plasmids.

Then, each CHO dhfr⁺ clone was first cultivated in DMEM (containing 5% fetal calf serum and 35 µg/ml proline) containing 0.1 µM methotrexate (MTX), and cells which acquired MTX resistance by gene amplification were selected. Thereafter, 1 µM MTX-resistant cells and 10 µM MTX-resistant cells were selected in turn.

For the respective CHO dhfr⁺ cell clones thus obtained and the MTX-resistant cell strains thereof, FGF receptor extracellular domains secreted in the culture solutions were detected by using the Western blotting method, thereby screening the produced cell strains. Namely, each cell strain proliferated to a confluent of 80% on a 24-well plate was cultivated in DMEM/Ham's medium (1:1) containing 0.5% fetal calf serum and 10 µg/ml insulin for 3 days. After SDS-PAGE, 0.5 ml of that culture solution [5% trichloroacetic acid (TCA) precipitation] was submitted to the Western blotting method by using the rabbit polyclonal antibody described in Example 3, (b) as a primary antibody.

The results revealed that CHO 1315-115, CHO 1315-123 and CHO 1315-1023 (IFO 50326, FERM BP-3362) cells obtained as 1 µM or 10 µM MTX-resistant cells by transfecting pTB1315 produced and secreted FGF receptor cell domains (BFR-1ex) of 60 to 70 kDa (the amino acid sequence thereof is shown in FIG. 12). Further, the results revealed that CHO 1316-161, CHO 1316-172 (IFO 50327, FERM BP-3363) and CHO 1316-1053 cells obtained as 1 µM or 10 µM MTX-resistant cells by transfecting pTB1316 produced and secreted FGF receptor extracellular domains (BFR-2ex) of 40 to 50 kDa.

The BFR-1ex- or BFR-2ex-producing CHO cell line was cultivated, adding ³⁵S-methionine (1000 Ci/mmole, 50 µCi/ml) thereto, in the presence or absence of tunicamycin (5 µg/ml), and the ³⁵S-methionine-labeled protein in the culture solution was subjected to immune precipitation by using the above-mentioned rabbit polyclonal antibody, followed by analysis by SDS-PAGE. As a result, it was suggested that the 46-kDa protein was glycosylated to a 70-kDa protein for BFR-1ex produced by these transformant CHO cells, and that the 35-kDa protein was glycosylated to a 45-kDa protein for BFR-2ex.

The following references, which are referred to for their disclosures at various points in this application, are incorporated herein by reference.

European Patent Publication No. 237,966
European Patent Publication No. 281,822
European Patent Publication No. 326,907

European Patent Publication No. 394,951.
Nucleic Acids Research 18, 1906 (1990)
The EMBO Journal 9, 2685 (1990)
Molecular and Cellular Biology 8, 5541–5544 (1988)
Proc. Natl. Acad. Sci. USA 87, 4378–4382 (1990)
Science 245, 57–60 (1989)
Genetic Engineering, Academic Press, p.31–50 (1983)
Genetic Engineering: Principles and Methods, Plenum Press, vol. 3, p.1–32 (1981)
Catalogue of Cell Lines & Hybridomas, 5th edition (1985), published by ATCC
Biochemistry 18, 5294 (1979)
Molecular and Cellular Biology 2, 161 (1982)
Molecular and Cellular Biology 3, 280 (1983)
Gene 2, 95 (1977)
Gene 4, 121 (1978)
Gene 19, 259 (1982)
Methods in Enzymology 153, 3–11 (1987)
Biochemical and Biophysical Research Communication 112, 678 (1983)
Molecular Cloning, Cold Spring Laboratory, p.239 (1982)
Proc. Natl. Acad. Sci. USA 60, 160 (1968)
Nucleic Acids Research 9, 309 (1981)
Journal of Molecular Biology 120, 517, (1978)
Journal of Molecular Biology 41, 459 (1969)
Genetics 39, 440 (1954)
Gene 24, 255 (1983)
Journal of Biochemistry 95, 87 (1984)
Molecular Cloning, Cold Spring Harbor Laboratory, p.249 (1982).
Proc. Natl. Acad. Sci. USA 74, 560 (1977)
Nucleic Acids Research 1, 1513 (1979)
Proc. Natl. Acad. Sci. USA, 69, 2110 (1972)
Gene, 17, 107 (1982)
Molecular & General Genetics, 168, 111 (1979)
Proc. Natl. Acad. Sci. USA, 75, 1929 (1978)
Virology, 52, 456 (1973)
Journal of Experiments in Molecular Genetics, 431–433, Cold Spring Harbor Laboratory, New York, 1972
Proc. Natl. Acad. Sci. USA, 77, 4505 (1980)
Science, 122, 501 (1952)
Virology, 8, 396 (1959)
Journal of the American Medical Association, 199, 519 (1967)
Proceeding of the Society for the Biological Medicine, 73, 1 (1950)
DNA Cloning, A Practical Approach, p.49, IRL Press, Oxford (1985)
DNA Cloning, A Practical Approach, p.79, IRL Press, Oxford (1985)
Molecular Cloning, p.320, Cold Spring Harbor Laboratory (1982)
Science 7, 57 (1989)
Molecular Cloning, p.309, Cold Spring Harbor Laboratory (1982)
Cell Struct. Funct. 12, 205–217 (1987)

What is claimed is:

1. A water soluble mutein of fibroblast growth factor (FGF) receptor which consists of the amino acid sequence shown in SEQ ID No. 12 or SEQ ID No. 14.

2. A recombinant DNA having a nucleotide sequence coding for the water soluble mutein of fibroblast growth factor (FGF) receptor according to claim 1.

3. A vector containing the recombinant DNA according to claim 2.

4. A transformant transformed with the vector according to claim 3.

5. The transformant according to claim 4 which is *E. coli* MM294 (DE3)/pLysS, pTB1289.

6. The transformant according to claim 4 which is *E. Coli* MM294 (DE3)/pLysS, pTB1290.

7. A process for producing a water soluble mutein of FGF receptor which consists of the amino acid sequence shown in SEQ ID NO:12 or SEQ ID NO:14, which process comprises cultivating the transformant of claim 4 in a culture medium under conditions suitable for expression of said mutein and recovering the water soluble mutein from said culture medium.

* * * * *

UNITED STATES PATENT AND TRADEMARK OFFICE
CERTIFICATE OF CORRECTION

PATENT NO. : 5,750,371
DATED: May 12, 1998
INVENTOR(S): Senoo, et al.

It is certified that error appears in the above-identified patent and that said Letters Patent is hereby corrected as shown below:

Assignee: please insert --"Takeda Chemical Industries, Ltd., Osaka, JAPAN"--.

Signed and Sealed this

Twenty-second Day of May, 2001

Attest:

NICHOLAS P. GODICI

Attesting Officer　　Acting Director of the United States Patent and Trademark Office